United States Patent
Cai et al.

(10) Patent No.: US 9,115,126 B2
(45) Date of Patent: Aug. 25, 2015

(54) 1H-[1,2,3]TRIAZOLO[4,5-C]PYRIDINE-4-CARBONITRILE DERIVATIVES

(75) Inventors: Jiaqiang Cai, Newhouse (GB); David Jonathan Bennett, West Point, PA (US); Philip Stephen Jones, Newhouse (GB)

(73) Assignee: Merck Sharp & Dohme B.V., Haarlem (NL)

( * ) Notice: Subject to any disclaimer, the term of this patent is extended or adjusted under 35 U.S.C. 154(b) by 492 days.

(21) Appl. No.: 13/519,924

(22) PCT Filed: Jan. 13, 2011

(86) PCT No.: PCT/EP2011/050393
§ 371 (c)(1),
(2), (4) Date: Jun. 29, 2012

(87) PCT Pub. No.: WO2011/086125
PCT Pub. Date: Jul. 21, 2011

(65) Prior Publication Data
US 2012/0283239 A1    Nov. 8, 2012

Related U.S. Application Data

(60) Provisional application No. 61/295,377, filed on Jan. 15, 2010.

(30) Foreign Application Priority Data

Jan. 15, 2010 (EP) .................................... 10150828

(51) Int. Cl.
| | |
|---|---|
| C07D 471/04 | (2006.01) |
| A61K 31/5377 | (2006.01) |
| A61K 31/496 | (2006.01) |
| A61K 31/54 | (2006.01) |
| A61K 31/437 | (2006.01) |
| A61K 31/551 | (2006.01) |

(52) U.S. Cl.
CPC .................................... C07D 471/04 (2013.01)

(58) Field of Classification Search
CPC ............. C07D 471/04; A61K 31/5377; A61K 31/496; A61K 31/54
USPC ............ 514/210.21; 546/117; 544/362, 58, 2, 544/228, 5
See application file for complete search history.

(56) References Cited

U.S. PATENT DOCUMENTS

2007/0117785 A1   5/2007   Butler et al.

FOREIGN PATENT DOCUMENTS

| EP | 1 724 264 A1 | 11/2006 |
|---|---|---|
| WO | 03/020278 A1 | 3/2003 |
| WO | 03/020721 A1 | 3/2003 |
| WO | 2004/000819 A1 | 12/2003 |
| WO | 2004/000843 A1 | 12/2003 |
| WO | 2005/085210 A | 9/2005 |
| WO | 2009/010491 A1 | 1/2009 |
| WO | WO2010081859 A1 | 7/2010 |

OTHER PUBLICATIONS

EP 09150709.5, Jan. 16, 2009 EP Applicant: N.V. Organon (Equivalent WO 2010/081859).
Zheng, T. et al., Inducible targeting of IL-13 to the adult lung causes matrix metalloproteinase- and cathepsin-dependent emphysema, The Journal of Clinical Investigation, 2000, p. 1081-1093, vol. 106, No. 9.
Asagiri, M. et al., "Cathepsin K-Dependent Roll-Like Recptor 9 Signaling Revealed in Experimental Arthritis", Science. 2008. p. 624-, vol. 319.
Bossardi, M. J. et al., "Proteolytic Activity of Human Osteoclas Chathepsin K", The Journal of Biological Chemistry 1996, p. 12517-12524, vol. 271, No. 21.
Bromme, D. et al., "Human Cathepsin O2, a Matrix Protein-degrading Cysteine Protease Expressed in Osteoclasts", The Journal of Biological Chemistry. 1996, p. 2126-2132. vol. 271 No. 4.
Bromme, D. et al., "Human Cthepsin O2 a Novel Cysteine Protease Highly Expressed in Osteociastomas and Ovary Molecular Cloning, Sequencing and Tissue Distribution", Biol. Chem. Hoppe-Seyler, 1995, p. 379-384, vol. 376.

(Continued)

*Primary Examiner* — Jennifer M Kim
(74) *Attorney, Agent, or Firm* — Baerbel R. Brown; Catherine D. Fitch

(57) ABSTRACT

The invention relates to 1H-[1,2,3]triazolo[4,5-c]pyridine-4-carbonitrile derived Cathepsin S inhibitors of Formula (I), wherein $R_1$ is H or $(C_{1-3})$alkyl; $R_2$ is halogen or $(C_{1-4})$alkyl, optionally substituted with one or more halogens; n is 1-3; X is O or $CH_2$; U, V and W are CH; or one of U, V and W is N; Y is a group capable of interacting with the $S_n \ldots S_2$ substites of the active site of Cathepsin S; or a pharmaceutically acceptable salt thereof, to pharmaceutical compositions comprising the same as well as to the use of these derivatives for the preparation of a medicament for the treatment of cathepsin S related diseases such as atherosclerosis, obesity, inflammation and immune disorders, such as rheumatoid arthritis, psoriasis, cancer, and chronic pain, such as neuropathic pain.

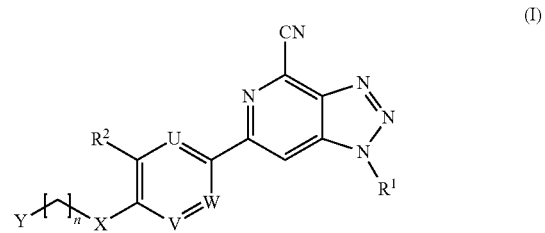

(I)

7 Claims, 1 Drawing Sheet

(56) References Cited

OTHER PUBLICATIONS

Chang, W.S.W. et al., "Lysomal Cysteine Proteinase Cathepsin S as a Potential Target for Anti-Cancer Therapy", Journal of Cancer Molecules, 2007. p. 5-14, vol. 3, No. 1.

Clark, A. K. et al., "Inhibition of spinal microglial cathepsin S for the reversal of neuropathic pain", PNAS, 2007 p. 10655-10660. vol. 104, No. 25.

Fissolo, N. et al., "Dual inhibition of proteasomal and lysosomal proteolysis amellorates autoimmune central nervous system inflammation", Eur. J. Immunol, 2008. p. 2401-2411. vol. 38.

Flannery. T. et al., "The Clinical Significance of Cathepsin S Expression in Human Astrocytomes", American Journal of Pathology, 2003, p. 175-, vol. 163 No. 1

Kafienah, W. et al., "Human cathepsin K cleaves native type I and II collagens at the N-terminal end of the triple helix", Biochem J., 1998, p. 727-732, vol. 331.

Kos. J. et al., "Cathepsin S in tumours, regional lymph nodes and sera of patients with lung cancer: relation of prognosis", British Journal of Cancer, 2001, p. 1193-1200. vol. 85 No. 8.

Liu, J. et al., "increased serum cathepsin S in patients with atherosclerosis and diabetes", Atherosclerosis. 2006. p. 411-419, vol. 186.

Marki. P. et al., "Discovery of Novel Cathepsin S Inhibitors by Pharmacophore-Based Vitual High-Throughput Screening", J. Chem. Int. Model, 2008. p. 1693-1705, vol. 48.

Nakagawa. T. Y. et al., "Impaired Invariant Chain Degradation and Antigen Presentation and Diminished Collagen-Induced Arthritis in Cathepsin S Null Mice", Immunity, 1999, p. 207-217, vol. 10.

Broome, D. et al., "High level expression and crystaliization of recombinant human cathepsin S". Protein Science. 1996. p. 789-791 vol. 5.

Riese, R. J. et al., "Cathepsin S Activity Reulates Antigen Prosentation and Immunity", J. Clin. Invest, 1998, p. 2351-. vol. 101.

Riese R. J. et al., "Essential Role for Cathepsin S in MHC Class II-Associated Invariant Chain Processing and Peptide Loading", Immunity, 1996, p. 357-366, vol. 4.

Schechter, I. et al., "On the Size of the active site in Proteases", Biochemical and Biophysical Research Communication, 1967, p. 157-, vol. 27, No. 2.

Shi, G. P. et al., "Cathepsin S Required for Normal MHC Class II Peptide Loading and Germinal Center Development", Immunity, 1999, p. 197-206. vol. 10.

Sukhova, G. K. et al., "Deficiency of cathepsin S reduces atheroscierosis in LDL receptor-deficient mice", The Journal of Clinical Investigation, 2003, p. 897-, vol. 111, No. 6.

Taleb, S. et al., "Emerging role of cathepsin S in obesity and its associated diseases", Clin Chem Lab Med. 2007 p. 328-332 vol. 45, No. 3.

Wiederanders, B. et al., "Primary structure of bovine cathepsin S Comparison to cathepsin L, H. B and papain", FEBS. 1991, p. 189-192, vol. 286, No. 1, 2.

Yang, H. et al., "Cathepsin S is Required for Murine Autoimmune Myasthenia Gravis Pathogenesis", The Journal of Immunology, 2005, p. 1729-, vol. 174.

Roberts, R. "Lysosomal Cysteine Proteases: Structure, Function and Inhibition of Cathepsins", Drug News Perspect, 2005, p. 605-614, vol. 18, No. 10.

Sukhova, G. K. et al., "Expression of the Elastolytic Cathepsins S and K in Human Atheroma and Reulation of their Production in smooth Muscle Cells", J. Clin. Invest, 1998, p. 576-583, vol. 102. No. 3.

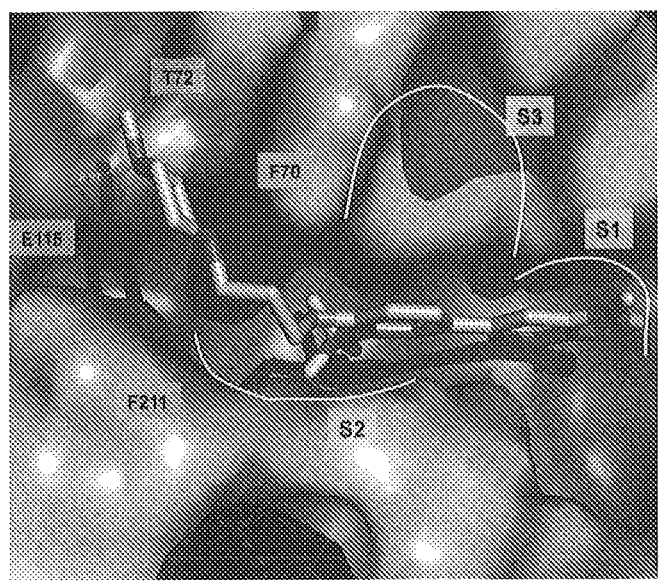

1H-[1,2,3]TRIAZOLO[4,5-C]PYRIDINE-4-CARBONITRILE DERIVATIVES

CROSS-REFERENCE TO RELATED APPLICATIONS

This application is a U.S. National Phase application under 35 U.S.C. §371 of PCT Application No. PCT/EP2011/050393, filed Jan. 13, 2011, which claims priority from and the benefit of U.S. Provisional Application No. 61/295,377 filed on Jan. 15, 2010, and EP Provisional Application No. 10150828.1 filed on Jan. 15, 2010.

The invention relates to 1H-[1,2,3]triazolo[4,5-c]pyridine-4-carbonitrile derivatives, to pharmaceutical compositions comprising the same, as well as to the use of these derivatives for the preparation of a medicament for the treatment of cathepsin S related diseases such as atherosclerosis, obesity, inflammation and immune disorders, such as rheumatoid arthritis, psoriasis, lupus, asthma and chronic pain, such as neuropathic pain.

Cysteine proteases represent a class of peptidases characterised by the presence of a cysteine residue in the catalytic site of the enzyme, and these proteases are associated with the normal degradation and processing of proteins. Many pathological disorders or diseases are the results of abnormal activity of cysteine proteases such as over expression or enhanced activation. The cysteine cathepsins, e.g. cathepsin B, K, L, S, V, F, are a class of lysosomal enzymes which are implicated in various disorders including inflammation, autoimmune diseases, e.g. rheumatoid arthritis, psoriasis, asthma, osteoarthritis, osteoporosis, tumors, coronary disease, atherosclerosis, and infectious diseases.

Cathepsin S is highly expressed in antigen presenting cells of lymphatic tissues, primarily in lysosomes (Bromme et al., Science, 5, 789, 1996; Riese, et al., Immunity, 4, 357, 1996). In the antigen presenting cells cathepsin S plays a major role in antigen presentation by degradation of invariant chain that is associated with the major histocompatibility class II complex. Cathepsin S is also believed to be involved in the antigen processing as well. Cathepsin S deficient mice are healthy and normal in most respects but exhibit defects in immune functions and showed marked resistance to the development of collagen-induced arthritis (Nakagawa et al., Immunity, 10, 207, 1999; Shi et al, Immunity, 10, 197, 1999; Yang et al., 174, 1729, 2005). Cathepsin S inhibitors are effective in an asthma model (Riese et al., J. Clin. Invest. 101, 2351, 1998). Blocking invariant chain degradation should decrease antigen presentation to CD4 cells specifically and as such reduces unwanted side effects of other immunosuppressive drugs such as steroids. A recent patent publication (Johnson & Johnson, US 2007/0117785) has revealed that inhibitors of cathepsin S block the presentation of several crude allergen extracts in a human ex vivo assay, thereby supporting the use of cathpsin S inhibitors for the treatment of certain allergic conditions, such as rheumatoid arthritis, psoriasis. Different from most other lysosomal proteases that are only active under acidic conditions, the activity of cathepsin S exhibits a broad pH optimum that extents to alkaline pH. This feature enables that cathepsin S to function both inside and outside lysosomes (Broemme et al., Febs Lett., 286, 189, 1991). The broad pH feature and the high elastase activity of extracellular cathepsin S could also contribute to extensive remodeling of extracellular matrix architecture. As a result, cathepsin S has been shown to degrade all of the major components of the extracellular matrix and has been implicated in the pathogenic response that leads to atherosclerosis, obesity, emphysema and chronic obstructive pulmonary disease and cancer (Shi, et al., Atherosclerosis, 186, 411, 2006; Clement et al., Clin Chem Lab Med., 45(3), 328, 2007; Chang et al., J Cancer Mol., 3(1), 5, 2007; Shi et al., Immunity, 10, 197, 1999; Zheng et al., J. Clin. Invest., 106, 1081, 2000; Libby et al., J Clin Invest 102, 576, 1998; Sukhova et al, ibid, 111, 897, 2003). It was reported that serum cathepsin S level is significantly increased in both atherosclerosis and diabetes patients and modulating cathepsin S activity may have therapeutic application in the treatment of patients with these common illnesses (Shi, et al., Atherosclerosis, 186, 411, 2006; Clement et al., Clin Chem Lab Med., 45(3), 328, 2007). Cathepsin S has been indicated for pain (WO 2003020278; Clark et al., PNAS, 104, 10655, 2007), cancer process, e.g. angiogenesis, metastasis, growth and cell proliferation (Johnston et al., Am J Path., 163, 175, 2003; Kos et al., Brit J Cancer, 85, 1193, 2001). Recent publication has also indicated that cathepsin S inhibitor alone or in combination with proteasome inhibition can have therapeutic usage against inflammation-induced neurodegenerative disease, such as multiple sclerosis (Weissert, et al., Eur. J. Immunol., 38, 2401, 2008).

Other cysteine cathepsins, e.g cathepsin K has strong collagenolytic, elastase and gelatinase activities (Bromme et al., J. Biol, Chem, 271, 2126-2132, 1996) and is predominantly expressed in osteoclasts (Bromme and Okamoto, Biol. Chem. Hopp-Seyler, 376, 379-384, 1995). It cleaves key bone matrix proteins, including type I and II collagen (Kaffienah et al., Biochem. J. 331, 727-732, 1998), gelatine, osteopontin and osteonectin, and as such is involved in extracellular matrix metabolism necessary for normal bone growth and remodelling (Bossard et al., J. Biol. Chem. 271, 12517-12524, 1996). Inhibition of cathepsin K should result in the diminuation of osteoclast mediated bone resorption. Cathepsin K inhibitors may therefore represent new therapeutic agents for the treatment of disease states in man such as osteoporosis, cancer, osteoarthritis. A recent publication also suggest that cathepsin K plays a critical role in the immune system and may serve as a valid therapeutic target in autoimmune diseases (Takayanagi, et al., Science, 319, 624, 2008). Sukhova et al (J. Clin. Invest. 102, 576-583, 1998) have demonstrated that cells (macrophages) that migrate into and accumulate within developing human atherosclerotic plaques also synthesize the potent elastases Cathepsin K and S. Matrix degradation, particularly in the fibrous cap of such plaques, is a crucial process in atherosclerotic lesion destabilization. Thus, the metabolism of the extracellular matrix components collagen and elastin, which confer structural integrity upon the lesion's fibrous cap, can critically influence the clinical manifestations of atherosclerosis, such as coronary artery thrombosis as a result of rupture of an atherosclerotic plaque. Inhibition of cathepsins K and S at sites of plaques prone to rupture may thus represent an effective way of preventing such events.

The cysteine cathepsins are a class of proteolytic enzymes that catalyze the hydrolysis of specific peptide bonds in proteinaceous substrates.

Schechter and Berger (Biochem. Biophys. Res. Commun. 27, 157-162, 1967) have proposed a now often used nomenclature for the identification of amino acid residues in the substrates of proteinases:

~=scissile bond
Substrate: . . . Pn . . . P5-P4-P3-P2-P1~P1'-P2'-P3' . . . Pn' . . . .
Enzyme: . . . Sn . . . S5-S4-S3-S2-S1-S1'-S2'-S3' . . . Sn' . . . .

The amino acid residues of the subsites of the substrate at the N-terminus of the scissile P1-P1' bond are designated P1, P2 etc and as P1', P2' etc at the C-terminus. These subsites of the substrate correspond to the possible subsites (S1, S2, etc) on the enzyme with which the binding interactions take place.

Cysteine proteases are characterized by having a cysteine residue at the active site which serves as a nucleophile. The active site also contains a histidine residue. The imidazole ring on the histidine serves as a base to generate a thiolate anion on the active stie cysteine, increasing its nucleophilicity. When a protein substrate is recognized by the protease, the P1~P1' amide bond to be cleaved is directed to the active site, where the thiolate attacks the carbonyl carbon forming a an acyl-enzym intermediate and cleaving the amide bond, liberating an amine. Subsequently, water cleaves the acyl-enzyme species regenerating the enzyme and liberating the other cleavage product of the substrate, the carboxylic acid (Roberts, R. "Lysosomal cysteine Proteases: Structure, Function and Inhibition of cathepsins" Drug News Perspect 18 (10), 605-614, 2005)

Cathepsin S is a monomeric protein consisting of 217 amino acids, whose crystallographic structure is well known (Rebecca Roberts, Drug News Perspect 2005, 18 (10) 605-614). The catalytic triad of human Cathepsin S is represented by Cys-25, H is 164 and Asn-184. These residues are positioned near the S1 and S1' subsites on the surface of the enzyme (Markt et al. J. Chem. Inf. Model. 2008, 48, 1693-1705).

4-Amino-pyrimidine-2-carbonitrile derivatives have been disclosed as inhibitors of cathepsins K and/or S in the International Patent Application WO 03/020278 (Novartis Pharma GMBH), while structurally related 4-amino-pyrimidine-2 carbonitrile derivatives were recently disclosed in WO04/000819 (ASTRAZENECA AB) as cathepsin S inhibitors. Pyrrolo-pyrimidines have likewise been disclosed as cathepsin K and/or S inhibitors in WO 03/020721 (Novartis Pharma GMBH) and WO 04/000843 (ASTRAZENECA AB). Recently, carbonitrile substituted bicyclic nitrogen containing aromatic systems were disclosed in the International Patent Application WO 05/085210 (Ono Pharmaceutical Co.) as cysteine protease inhibitors useful in the treatment of osteoporosis.

All of these aromatic-carbonitrile containing inhibitors of Cathepsin S and/or Cathepsin K are characterized by an electrophilic nitrile warhead which on interaction with the enzyme is attacked by the nucleophilic sulfhydryl group of the active site residue Cys-25, thereby forming a reversible covalent bond.

Recently, a series of 1H-imidazo[4,5-c]pyridine-4-carbonitrile derivatives was disclosed in WO 2009/010491 (N.V. Organon) as inhibitors of cathepsin S and cathepsin K, useful in the treatment of osteoporosis, atherosclerosis, inflammation and immune disorders, such as rheumatoid arthritis, psoriasis, asthma, and chronic pain, such as neuropathic pain.

BRIEF DESCRIPTION OF THE FIGURE

FIG. 1 is an illustration of the surface representation of the Cathepsin S active site cleft.

1-Methyl-6-{4-[3-(4-methylpiperazin-1-yl)-propoxy]-3-(trifluoromethyl)-phenyl}-1H-imidazo[4,5-c]pyridine-4-carbonitrile (the compound disclosed in Example 4e of WO 2009/010491) was crystallized in a covalent complex with Cathepsin S.

FIG. 1 is a surface representation of the Cathepsin S active site cleft showing the position of the imidazopyridine derived inhibitor in relation to the specific subsites S1, S2 and S3 (unoccupied) on the enzyme, whereby the "electrophilic warhead" containing imidazo[4,5-c]pyridine-4-carbonitrile part of the molecule is covalently linked in the S1 site on the enzyme, the trifluorophenyl moiety being bound in the hydrophopbic S2 site on the enzyme, while the piperazine containing side chain protrudes into a tunnel region flanked by Phe-70 and Phe-211 on the enzyme, the phenyl groups of which are approximately at a distance of 8-9 Å. After the tunnel there is a deep hydrophobic pocket that is flanked at the end by the polar side chains of Glu-115 and Thr-72.

It has been surprisingly found that on replacement of the imidazo[4,5-c]pyridine-4-carbonitrile moiety of the cathepsin inhibitors of the prior art with a 1H-[1,2,3]triazolo[4,5-c]pyridine-4-carbonitrile moiety, which amounts to the substitution of a single carbon atom by a nitrogen atom, the cathepsin S inhibitory activity of the compounds is much improved. In most cases, compounds of the present invention are 5-10 fold more active than the corresponding imidazopyridine derivatives disclosed in WO 2009/010491. The 1H-[1,2,3]triazolo[4,5-c]pyridine-4-carbonitrile derived cathepsin inhibitors also exhibit, in comparison with the corresponding imidazo[4,5-c]pyridine-4-carbonitrile derived cathepsin inhibitors, a 5-10 fold increase in cell based cathepsin S inhibitory activity on cleavage of invariant chain, as measured by lip10 accumulation.

Another advantage for many of the 1H-[1,2,3]triazolo[4,5-c]pyridine-4-carbonitrile derived compounds of the present invention was founding a much better rat oral bioavailablity as compared to the corresponding imidazo[4,5-c]pyridine-4-carbonitrile derived cathepsin inhibitors such as those disclosed in WO 2009/010491.

In one aspect the present invention provides 1H-[1,2,3] triazolo[4,5-c]pyridine-4-carbonitrile derived cathepsin inhibitors having the general Formula I

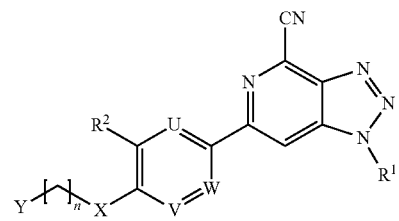

Formula I wherein
$R_1$ is H or $(C_{1-3})$alkyl;
$R_2$ is halogen or $(C_{1-4})$alkyl, optionally substituted with one or more halogens;
n is 1-3;
X is O or $CH_2$;
U, V and W are CH; or one of U, V and W is N;
Y is a group capable of interacting with the $S_n \ldots S_2$ substites of the active site of Cathepsin S;
or a pharmaceutically acceptable salt thereof.

In another aspect the invention provides 1H-[1,2,3]triazolo[4,5-c]pyridine-4-carbonitrile derivatives of general formula I
wherein
$R_1$ is H or $(C_{1-3})$alkyl;
$R_2$ is halogen or $(C_{1-4})$alkyl, optionally substituted with one or more halogens;
n is 1-3;
X is O or $CH_2$;
U, V and W are CH; or one of U, V and W is N;
and
wherein Y is selected from
—OH
—$(C_{1-4})$alkyloxy
—$(C_{1-4})$alkyloxy$(C_{1-4})$alkyloxy —NR$_3$R$_4$
—NR$_4$SO$_2$R$_5$,
-pyridyl or N-oxy-pyridyl;
-Het;

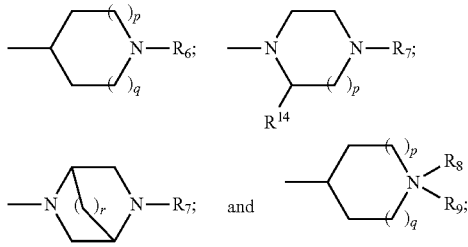

R$_3$ is H, (C$_{1-3}$)alkyl, (C$_{1-6}$)alkylcarbonyl, NR$_{10}$R$_{11}$CR$_{12}$R$_{13}$CO or NR$_{10}$R$_{11}$CO(CH$_2$)$_m$;
R$_4$ is H, (C$_{1-3}$)alkyl or (C$_{3-5}$)cycloalkyl; or
R$_3$ and R$_4$ together with the nitrogen to which they are bonded form a saturated 6-membered heterocyclic ring containing a further heteroatom selected from O, S and SO$_2$;
R$_5$ is (C$_{1-6}$)alkyl;
R$_6$ is selected from
  H,
  (C$_{1-4}$)alkyl, optionally substituted with 1 or 2 substituents selected from OH, halogen, CF$_3$ or (C$_{1-4}$)alkylsulfonyl;
  (C$_{1-4}$alkylsulfonyl,
  (C$_{1-6}$)alkylcarbonyl,
  Het,
  Het-CH$_2$,
  pyridyl, optionally fused to a benzo ring and optionally substituted with
  (C$_{1-4}$)alkyl, halogen or cyano;
  NR$_{10}$R$_{11}$CO(CH$_2$)$_m$; and
  NR$_{10}$R$_{11}$CR$_{12}$R$_{13}$CO,
R$_7$ is selected from
  H,
  (C$_{1-4}$)alkyl, optionally substituted with 1 or 2 substituents selected from OH, halogen, CF$_3$ or (C$_{1-4}$)alkylsulfonyl;
  (C$_{1-6}$)alkylcarbonyl;
  (C$_{1-4}$)alkylsulfonyl; pyridyl, optionally substituted with (C$_{1-3}$)alkyl, halogen or CF$_3$; and
  NR$_{10}$R$_{11}$CO(CH$_2$)$_m$;
R$_8$ is H, (C$_{1-4}$)alkyl or OH;
R$_9$ is H, (C$_{1-4}$)alkyl or NR$_{10}$R$_{11}$CO(CH$_2$)$_m$;
R$_{10}$ and R$_{11}$ are independently H or (C$_{1-6}$)alkyl; or
R$_{10}$ and R$_{11}$ form together with the N to which they are bonded a 5-7 membered saturated heterocyclic ring, optionally comprising a further heteroatom selected form O and S;
R$_{12}$ and R$_{13}$ are independently H or (C$_{1-4}$)alkyl; or
R$_{12}$ and R$_{13}$ form together with the carbon atom to which they are bonded a (C$_{3-5}$)cycloalkyl ring;
R$_{14}$ is H, CF$_3$ or oxo;
Het is a 5-membered heteroaryl ring comprising 1-3 heteroatoms selected from O, S and N, optionally substituted with (C$_{1-4}$)alkyl, halogen or cyano;
p and q are independently 0, 1 or 2;
r is 1 or 2;
m is 0, 1 or 2;
or a pharmaceutically acceptable salt thereof.

The 1H-[1,2,3]triazolo[4,5-c]pyridine-4-carbonitrile derivatives of the invention are inhibitors of cathepsin S and cathepsin K and can therefor be used for the preparation of a medicament for the treatment of osteoporosis, atherosclerosis, inflammation and immune disorders, such as rheumatoid arthritis, psoriasis, asthma, and chronic pain, such as neuropathic pain.

The term (C$_{1-6}$)alkyl, as used in the definition of Formula I, means a branched or unbranched alkyl group having 1-6 carbon atoms, like hexyl, pentyl, 3-methyl-butyl, butyl, isobutyl, tertiary butyl, propyl, isopropyl, ethyl and methyl.

The term (C$_{1-4}$)alkyl means a branched or unbranched alkyl group having 1-4 carbon atoms, like butyl, isobutyl, tertiary butyl, propyl, isopropyl, ethyl and methyl.

The term (C$_{1-3}$)alkyl means a branched or unbranched alkyl group having 1-3 carbon atoms, like propyl, isopropyl, ethyl and methyl.

In the terms (C$_{1-4}$)alkyloxy, (C$_{1-4}$)alkylsulfonyl and (C$_{1-4}$)alkyloxy(C$_{1-4}$)alkyoxyl each occurrence of (C$_{1-4}$)alkyl has the meaning as previously given.

In the terms (C$_{1-6}$)alkylcarbonyl and (C$_{1-6}$)alkylsulfonyl each occurrence of (C$_{1-6}$)alkyl has the meaning as previously given.

The term (C$_{3-5}$)cycloalkyl means a cycloalkyl group having 3-5 carbon atoms, such as cyclopentyl, cyclobutyl and cyclopropyl.

In the definition of formula I Het means a 5-membered heteroaryl ring comprising 1-3 heteroatoms selected from O, S and N. Examples of such heteroaryl rings, which are attached through a carbon atom, and which may be substituted by 1 or 2 (C$_{1-3}$)alkyl groups, are imidazolyl, pyrazolyl, thiazolyl, isothiazolyl, oxazolyl, isoxazolyl, thienyl, oxadiazolyl, and the like. Preferred rings are 1,3-thiazol-2-yl, 1,3-oxazol-2-yl, 1,2-oxazol-3-yl, 1,2-oxazol-4-yl, 1,2,4-oxadiazol-3-yl, 5-methyl-1,2,4-oxadiazol-3-yl, 1,2,4-oxadiazol-5-yl, 5-methyl-isoxazol-3-yl, 3-methyl-isoxazol-5-yl, and 1,3,4-oxadiazol-2-yl.

The term halogen means F, Cl, Br, or I. When halogen is a substituent at an alkyl group, F is preferred. A preferred halogen substituted alkyl group is trifluoromethyl.

Preferred in the invention are those compounds according to Formula I wherein X is O and U, V and W are CH.

Further preferred in the invention are those compounds according to Formula I wherein R$_1$ is methyl and R$_2$ is CF$_3$.

Specifically preferred 1H-[1,2,3]triazolo[4,5-c]pyridine-4-carbonitrile derivatives of the invention are:
1-methyl-6-(4-(2-(piperidin-4-yl)ethoxy)-3-(trifluoromethyl)phenyl)-1H-[1,2,3]triazolo[4,5-c]pyridine-4-carbonitrile;
6-(4-(2-(1-(2-dimethylamino-2-oxoethyl)piperidin-4-yl)ethoxy)-3-(trifluoromethyl)-phenyl)-1-methyl-1H-[1,2,3]triazolo[4,5-c]pyridine-4-carbonitrile;
1-methyl-6-(4-(2-(1-(2-methylamino-2-oxoethyl)piperidin-4-yl)ethoxy)-3-(trifluoromethyl)phenyl)-1H-[1,2,3]triazolo[4,5-c]pyridine-4-carbonitrile;
6-(4-(2-(1-(2-amino-2-oxoethyl)piperidin-4-yl)ethoxy)-3-(trifluoromethyl)phenyl)-1-methyl-1H-[1,2,3]triazolo[4,5-c]pyridine-4-carbonitrile;
6-(4-(2-(1-(2-hydroxy-2-methylpropyl)piperidin-4-yl)ethoxy)-3-(trifluoromethyl)phenyl)-1-methyl-1H-[1,2,3]triazolo[4,5-c]pyridine-4-carbonitrile;
1-methyl-6-(4-(2-(1-(pyridin-2-yl)piperidin-4-yl)ethoxy)-3-(trifluoromethyl)phenyl)-1H-[1,2,3]triazolo[4,5-c]pyridine-4-carbonitrile;
1-methyl-6-(4-(2-(1-(6-methylpyridin-2-yl)piperidin-4-yl)ethoxy)-3-(trifluoromethyl)-phenyl)-1H-[1,2,3]triazolo[4,5-c]pyridine-4-carbonitrile;
6-(4-(2-(1-(3-cyanopyridin-2-yl)piperidin-4-yl)ethoxy)-3-(trifluoromethyl)phenyl)-1-methyl-1H-[1,2,3]triazolo[4,5-c]pyridine-4-carbonitrile;

1-methyl-6-(4-(2-(1-(methylsulfonyl)piperidin-4-yl)ethoxy)-3-(trifluoromethyl)-phenyl)-1H-[1,2,3]triazolo[4,5-c]pyridine-4-carbonitrile;

6-(4-(2-(1-acetylpiperidin-4-yl)ethoxy)-3-(trifluoromethyl)phenyl)-1-methyl-1H-[1,2,3]triazolo[4,5-c]pyridine-4-carbonitrile;

4-(2-(4-(4-cyano-1-methyl-1H-[1,2,3]triazolo[4,5-c]pyridin-6-yl)-2-(trifluoromethyl)-phenoxy)ethyl)-N-methylpiperidine-1-carboxamide;

1-methyl-6-(4-(2-(1-(2-(methylsulfonyl)ethyl)piperidin-4-yl)ethoxy)-3-(trifluoro-methyl)phenyl)-1H-[1,2,3]triazolo[4,5-c]pyridine-4-carbonitrile;

1-methyl-6-(4-(pyridin-2-ylmethoxy)-3-(trifluoromethyl)phenyl)-1H-[1,2,3]triazolo-[4,5-c]pyridine-4-carbonitrile;

1-methyl-6-(4-(1-N-oxy-pyridin-2-ylmethoxy)-3-(trifluoromethyl)phenyl)-1H-[1,2,3]triazolo[4,5-c]pyridine-4-carbonitrile;

1-Methyl-6-(6-(2-(piperidin-4-yl)ethoxy)-5-(trifluoromethyl)pyridin-3-yl)-1H-[1,2,3]triazolo[4,5-c]pyridine-4-carbonitrile;

6-(6-(2-(1-(2-Dimethylamino-2-oxo-ethyl)piperidin-4-yl)ethoxy)-5-(trifluoromethyl)-pyridin-3-yl)-1-methyl-1H-[1,2,3]triazolo[4,5-c]pyridine-4-carbonitrile;

1-Methyl-6-(6-(2-(1-(2-methylamino-2-oxo-ethyl)piperidin-4-yl)ethoxy)-5-(trifluoromethyl)pyridin-3-yl)-1H-[1,2,3]triazolo[4,5-c]pyridine-4-carbonitrile;

6-(6-(2-(1-(2-Amino-2-oxo-ethyl)piperidin-4-yl)ethoxy)-5-(trifluoromethyl)pyridin-3-yl)-1-methyl-1H-[1,2,3]triazolo[4,5-c]pyridine-4-carbonitrile;

1-Methyl-6-(6-(2-(1-(2-oxo-2-(pyrrolidin-1-yl)ethyl)piperidin-4-yl)ethoxy)-5-(trifluoromethyl)pyridin-3-yl)-1H-[1,2,3]triazolo[4,5-c]pyridine-4-carbonitrile;

1-Methyl-6-(6-(2-(1-(2-morpholino-2-oxoethyl)piperidin-4-yl)ethoxy)-5-(trifluoro-methyl)pyridin-3-yl)-1H-[1,2,3]triazolo[4,5-c]pyridine-4-carbonitrile;

6-(4-(2-(1-(1-aminocyclopropanecarbonyl)piperidin-4-yl)ethoxy)-3-(trifluoro-methyl)phenyl)-1-methyl-1H-[1,2,3]triazolo[4,5-c]pyridine-4-carbonitrile;

6-(4-(2-(azetidin-3-yl)ethoxy)-3-(trifluoromethyl)phenyl)-1-methyl-1H-[1,2,3]-triazolo[4,5-c]pyridine-4-carbonitrile;

6-(4-(2-(1-(2-dimethylamino-2-oxoethyl)azetidin-3-yl)ethoxy)-3-(trifluoromethyl)-phenyl)-1-methyl-1H-[1,2,3]triazolo[4,5-c]pyridine-4-carbonitrile;

6-(4-((2-methoxyethoxy)methoxy)-3-(trifluoromethyl)phenyl)-1-methyl-1H-[1,2,3]-triazolo[4,5-c]pyridine-4-carbonitrile;

6-(4-(3-hydroxypropoxy)-3-(trifluoromethyl)phenyl)-1-methyl-1H-[1,2,3]triazolo-[4,5-c]pyridine-4-carbonitrile;

N-(3-(4-(4-cyano-1-methyl-1H-[1,2,3]triazolo[4,5-c]pyridin-6-yl)-2-(trifluoromethyl)-phenoxy)propyl)acetamide;

6-(4-(3-(dimethylamino)propoxy)-3-(trifluoromethyl)phenyl)-1-methyl-1H-[1,2,3]-triazolo[4,5-c]pyridine-4-carbonitrile;

6-(4-(3-(4-hydroxy-4-methylpiperidin-1-yl)propoxy)-3-(trifluoromethyl)phenyl)-1-methyl-1H-[1,2,3]triazolo[4,5-c]pyridine-4-carbonitrile;

1-(3-(4-(4-cyano-1-methyl-1H-[1,2,3]triazolo[4,5-c]pyridin-6-yl)-2-(trifluoromethyl)-phenoxy)propyl)piperidine-4-carboxamide;

1-methyl-6-(3-(trifluoromethyl)-4-(3-(4-(4-(trifluoromethyl)pyridin-2-yl)piperazin-1-yl)propoxy)phenyl)-1H-[1,2,3]triazolo[4,5-c]pyridine-4-carbonitrile;

1-methyl-6-(4-(3-(4-(3-methylpyridin-2-yl)piperazin-1-yl)propoxy)-3-(trifluoro-methyl)phenyl)-1H-[1,2,3]triazolo[4,5-c]pyridine-4-carbonitrile;

6-(4-(3-(4-(5-chloropyridin-2-yl)piperazin-1-yl)propoxy)-3-(trifluoromethyl)phenyl)-1-methyl-1H-[1,2,3]triazolo[4,5-c]pyridine-4-carbonitrile;

6-(4-(3-(4-(3-chloropyridin-2-yl)piperazin-1-yl)propoxy)-3-(trifluoromethyl)phenyl)-1-methyl-1H-[1,2,3]triazolo[4,5-c]pyridine-4-carbonitrile;

6-(4-(2-(1-((1,2,4-oxadiazol-5-yl)methyl)piperidin-4-yl)ethoxy)-3-(trifluoromethyl)-phenyl)-1-methyl-1H-[1,2,3]triazolo[4,5-c]pyridine-4-carbonitrile;

6-(4-(2-(1-((1,2,4-oxadiazol-3-yl)methyl)piperidin-4-yl)ethoxy)-3-(trifluoromethyl)-phenyl)-1-methyl-1H-[1,2,3]triazolo[4,5-c]pyridine-4-carbonitrile;

1-methyl-6-(4-(2-(1-(oxazol-2-ylmethyl)piperidin-4-yl)ethoxy)-3-(trifluoromethyl)-phenyl)-1H-[1,2,3]triazolo[4,5-c]pyridine-4-carbonitrile;

1-methyl-6-(4-(pyridin-3-ylmethoxy)-3-(trifluoromethyl)phenyl)-1H-[1,2,3]triazolo-[4,5-c]pyridine-4-carbonitrile;

1-methyl-6-(4-(2-(1-(6-methylpyridin-2-yl)azetidin-3-yl)ethoxy)-3-(trifluoromethyl)-phenyl)-1H-[1,2,3]triazolo[4,5-c]pyridine-4-carbonitrile;

1-methyl-6-(4-(2-(1-(pyridin-2-yl)azetidin-3-yl)ethoxy)-3-(trifluoromethyl)phenyl)-1H-[1,2,3]triazolo[4,5-c]pyridine-4-carbonitrile hydrochloride;

methyl-6-(4-(1-N-oxy-pyridin-3-ylmethoxy)-3-(trifluoromethyl)phenyl)-1H-[1,2,3]-triazolo[4,5-c]pyridine-4-carbonitrile;

1-methyl-6-(4-(pyridin-4-ylmethoxy)-3-(trifluoromethyl)phenyl)-1H-[1,2,3]triazolo-[4,5-c]pyridine-4-carbonitrile;

methyl-6-(4-(1-N-oxy-pyridin-4-ylmethoxy)-3-(trifluoromethyl)phenyl)-1H-[1,2,3]-triazolo[4,5-c]pyridine-4-carbonitrile;

6-(6-(2-(1-(2-Hydroxy-2-methylpropyl)piperidin-4-yl)ethoxy)-5-(trifluoromethyl)-pyridin-3-yl)-1-methyl-1H-[1,2,3]triazolo[4,5-c]pyridine-4-carbonitrile;

6-(6-(2-(1-(2-Hydroxyethyl)piperidin-4-yl)ethoxy)-5-(trifluoromethyl)pyridin-3-yl)-1-methyl-1H-[1,2,3]triazolo[4,5-c]pyridine-4-carbonitrile;

6-(4-(2-(1-(2-dimethylamino-2-oxoethyl)azetidin-3-yl)ethoxy)-3-(trifluoromethyl)-phenyl)-1-methyl-1H-[1,2,3]triazolo[4,5-c]pyridine-4-carbonitrile hydrochloride;

6-(4-(3-(dimethylamino)propoxy)-3-(trifluoromethyl)phenyl)-1-methyl-1H-[1,2,3]-triazolo[4,5-c]pyridine-4-carbonitrile;

2-(4-(3-(4-(4-cyano-1-methyl-1H-[1,2,3]triazolo[4,5-c]pyridin-6-yl)-2-(trifluoro-methyl)phenoxy)propyl)piperazin-1-yl)-N,N-dimethylacetamide;

6-(4-(3-(4-(2-hydroxyethyl)piperazin-1-yl)propoxy)-3-(trifluoromethyl)phenyl)-1-methyl-1H-[1,2,3]triazolo[4,5-c]pyridine-4-carbonitrile dihydrochloride;

2-(4-(2-(4-(4-cyano-1-methyl-1H-[1,2,3]triazolo[4,5-c]pyridin-6-yl)-2-(trifluoro-methyl)phenoxy)ethyl)piperazin-1-yl)-N,N-dimethylacetamide; dihydrochloride;

6-(4-(2-(4-(2-hydroxy-2-methylpropyl)piperazin-1-yl)ethoxy)-3-(trifluoromethyl)-phenyl)-1-methyl-1H-[1,2,3]triazolo[4,5-c]pyridine-4-carbonitrile dihydrochloride;

2-((1S,4S)-5-(2-(4-(4-cyano-1-methyl-1H-[1,2,3]triazolo[4,5-c]pyridin-6-yl)-2-(trifluoromethyl)phenoxy)ethyl)-2,5-diazabicyclo[2.2.1]heptan-2-yl)-N,N-dimethylacetamide;

N-(3-(4-(4-cyano-1-methyl-1H-[1,2,3]triazolo[4,5-c]pyridin-6-yl)-2-(trifluoro-methyl)phenyl)propyl)-2-(dimethylamino)-N-methylacetamide;

methyl-6-(4-(3-((1S,4S)-5-methyl-2,5-diazabicyclo[2.2.1]heptan-2-yl)propyl)-3-(trifluoromethyl)phenyl)-1H-[1,2,3]triazolo[4,5-c]pyridine-4-carbonitrile hydrochloride;

or a pharmaceutically acceptable salt thereof.

The invention provides in a further aspect pharmaceutical compositions comprising a 1H-[1,2,3]triazolo[4,5-c]pyridine-4-carbonitrile derivative having general Formula I, or a pharmaceutically acceptable salt thereof, in admixture with pharmaceutically acceptable auxiliaries.

The 1H-[1,2,3]triazolo[4,5-c]pyridine-4-carbonitrile derivatives of general Formula I may be prepared by the methods as depicted in Schemes 1 and 2. N-alkylation of 4-amino-6-chloro-2-cyano-3-nitropyridine (II) produces 4-N-alkylamino-6-chloro-2-cyano-3-nitropyridine (III), from which 4-alkylamino-3-amino-6-chloro-pyridine-2-carbonitrile (IV) is generated following reduction of the nitro group by either hydrogenation (using Pd/C—$H_2$) or by the use of $SnCl_2$ or Fe based reducing agents. Palladium catalysed coupling between boronic ester or acid (V) and 2-chloropyridine derivative (IV) provides (VI) as product. Diazotisation and in situ cyclisation gives desired product (I).

Scheme 1

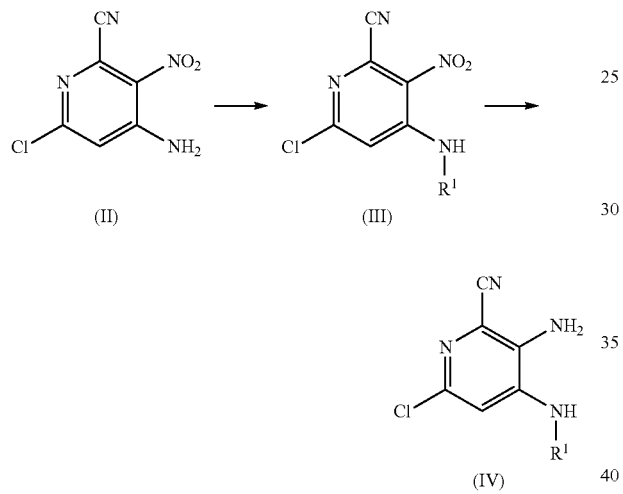

Scheme 2

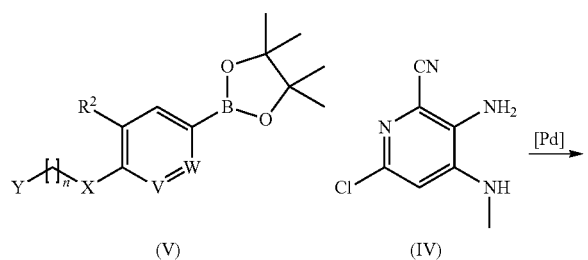

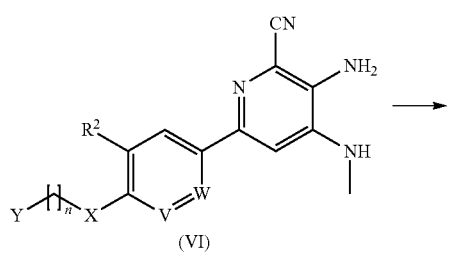

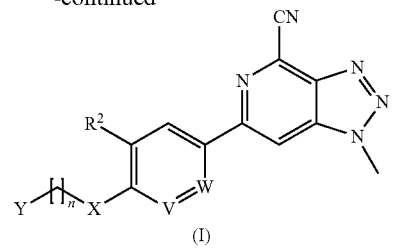

(I)

The boronic ester derivative of formula (V), can be synthesised as depicted in Scheme 3. Bromination of the 2-substituted phenol or hydroxypyridine derivative where V and/or W are N, of formula (VII), wherein $R_2$ has the meaning as defined before, with bromine or another bromination agent gives 4-bromophenol derivatives or bromopyridine derivatives (VIII) as product. Alkylation of the phenol OH by means of Mitsunobu type reaction or base-promoted alkylation with alkylbromide/iodide gives product of generic formula (IX). This arylbromide was then converted to desired boronic ester using the known palladium chemistry.

Scheme 3

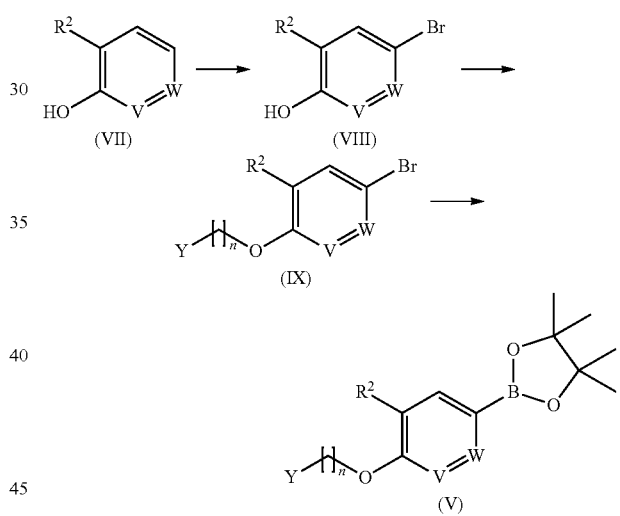

For the 1H-[1,2,3]triazolo[4,5-c]pyridine-4-carbonitrile derivatives of general Formula I where Y is amino or amido or sulfonamido group, these compounds may be prepared from the corresponding alcohol as shown in Scheme 4. The alcohol was initially converted to methanesulfonate (X) from which amines (XI), urea or amides (XII) or sulphonamides (XIII) can then be prepared.

Scheme 4

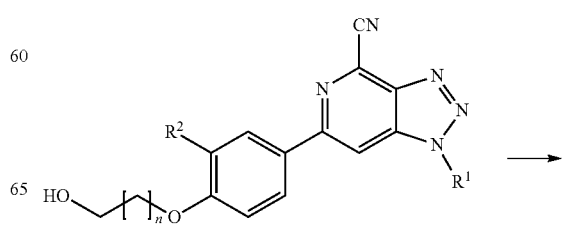

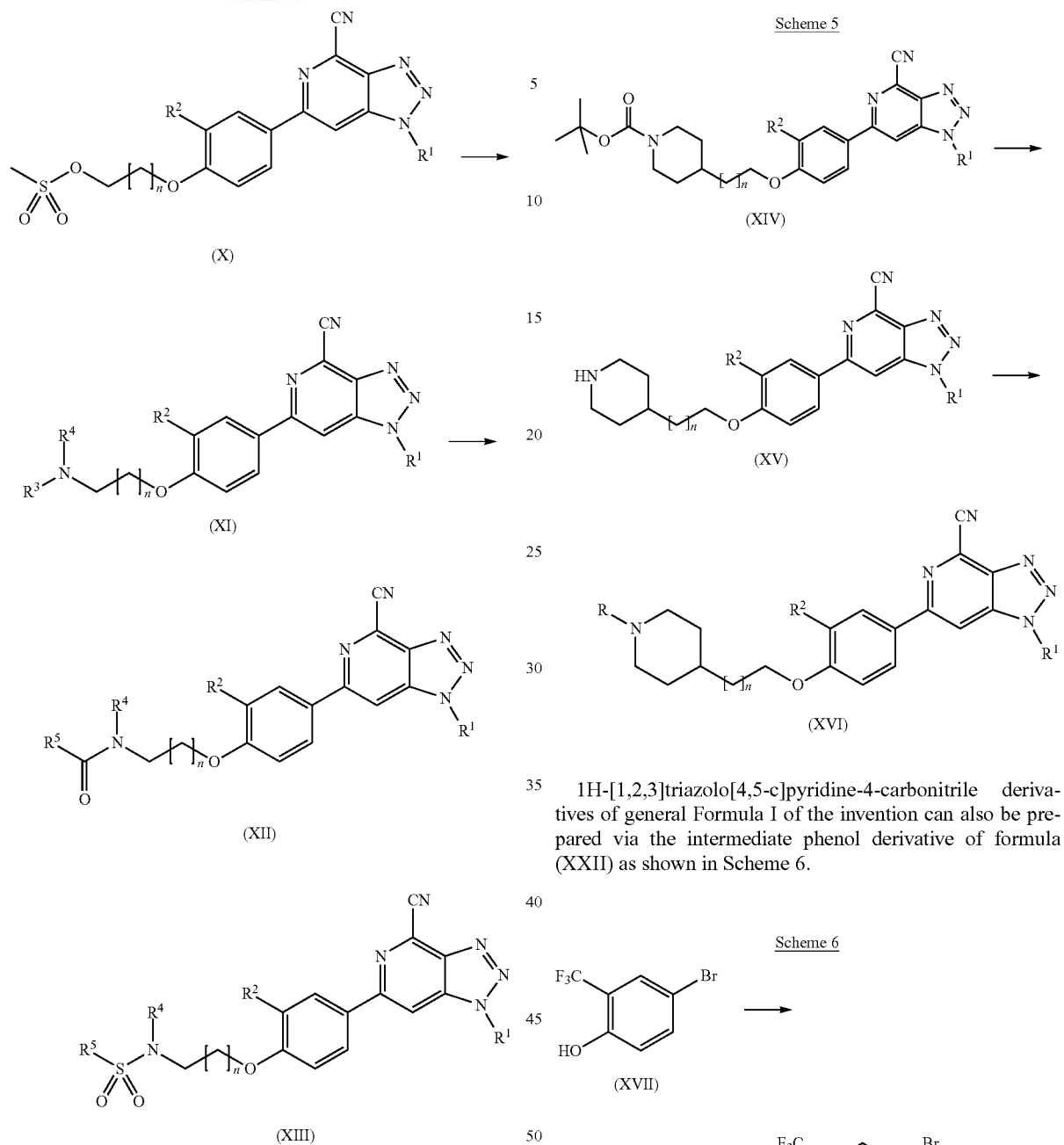

1H-[1,2,3]triazolo[4,5-c]pyridine-4-carbonitrile derivatives of general Formula I of the invention can also be prepared via the intermediate phenol derivative of formula (XXII) as shown in Scheme 6.

For compound of formula (I), wherein Y contains a primary or secondary amine, an alcohol or a carboxylic acid, these functionalities may need to be temporarily protected, such as for example by the acid labile t-butyloxycarbonyl (Boc) protecting group. Suitable other protecting groups for functional groups which are to be temporarily protected during syntheses are known in the art, for example from Wuts, P. G. M. and Greene, T. W.: *Protective Groups in Organic Synthesis*, Third Edition, Wiley, New York, 1999.

The resulting primary or secondary amine, alcohol or carboxylic acid can be then used for further derivatisation as shown by Scheme 5, such as alkylation or reductive alkylation, acylation or sulphonation.

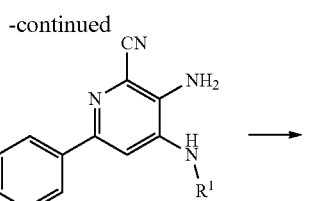

(XX)

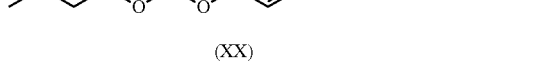

(XXI)

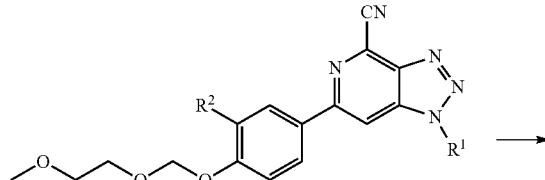

(XXII)

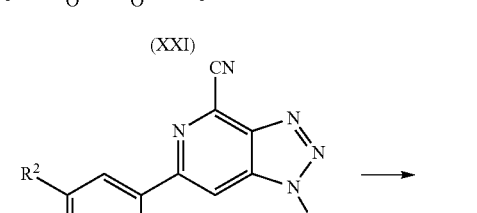

(I)

This intermediate is prepared starting from 4-bromo-2-trifluoromethylphenol (XVII): following protection of the phenolic hydroxy group as a methoxyethoxymethoxy (MEMO) ether (XVIII), the compound is converted to the boronic acid derivative (formula (XIX)) by standard methodology. Subsequent Suzuki coupling with the compound of formula (IV) gives the compound of formula (XX), Diazotisation-cyclisation provides triazolopyridine (XXI) from which the MEMO group is then removed using dilute aqueous hydrochloric acid. The resulting intermediate compound of formula (XXII) can be derivatised by either alkylation, a Mitsunobu reaction or using further methods known in the art, to prepare additional compounds of formula (I).

The 1H-[1,2,3]triazolo[4,5-c]pyridine-4-carbonitrile derivatives of the invention, which can be in the form of a free base, may be isolated from the reaction mixture in the form of a pharmaceutically acceptable salt. The pharmaceutically acceptable salts, such as acid addition salts, may further be obtained by treating the free base of Formula I with an organic or inorganic acid such as, but not limited to, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid and ascorbic acid.

Suitable salts of 1H-[1,2,3]triazolo[4,5-c]pyridine-4-carbonitrile derivatives of Formula I in which a carboxylate group is present can be an alkali metal salts, such as sodium, potassium or lithium salt, or may be a salt obtained from the combination with an organic base, such as trimethylamine, triethylamine and the like.

Compounds of the invention may exist in solvated as well as in unsolvated forms, including hydrated forms. In general, the solvated forms are equivalent to unsolvated forms and are intended to be encompassed within the scope of the present invention. Compounds of the present invention may exist as amorphous forms, but also multiple crystalline forms may be possible. In general, all physical forms are equivalent for the uses contemplated by the present invention and are intended to be within the scope of this invention.

The 1H-[1,2,3]triazolo[4,5-c]pyridine-4-carbonitrile derivatives of the invention and their salts may contain a centre of chirality in one or more of the side chains and may therefore be obtained as a pure enantiomer, or as a mixture of enantiomers, or as a mixture containing diastereomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The compounds of the invention were found to be inhibitors of human Cathepsin S and can therefore in a further aspect of the invention be used in therapy, and especially for the preparation of a medicament for the treatment of autoimmune disease, chronic obstructive pulmonary disease, pain, cancer, obesity, osteoporosis, atherosclerosis and related Cathepsin S dependent disorders, such as rheumatoid arthritis, psoriasis, asthma and IBD.

The compounds of the invention may be administered enterally or parenterally, and for humans preferably in a daily dosage of 0.001-100 mg per kg body weight, preferably 0.01-10 mg per kg body weight. Mixed with pharmaceutically suitable auxiliaries, e.g. as described in the standard reference, Gennaro et al., Remington's Pharmaceutical Sciences, (20th ed., Lippincott Williams & Wilkins, 2000, see especially Part 5: Pharmaceutical Manufacturing) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

Methods

General Chemical Procedures.

All reagents were either purchased from common commercial sources or synthesised according to literature procedures using commercial sources. Proton NMR ($^1$H NMR) were obtained on a Bruker DPX 400 spectrometer and are referenced to internal tetramethylsilane (TMS). Mass spectra were recorded on a Shimadzu LC-8A (HPLC) PE Sciex API 150EX LCMS. Analytical reversed-phase LCMS analysis was carried out on LUNA C18 column (5 μm; 30×4.6 mm) under gradient conditions (90% water/0.1% formic acid to 90% acetonitrile/0.1% formic acid) at a flow rate of 4 ml/min.

ABBREVIATIONS

Dimethylformamide (DMF), N-methylpyrrolidinone (NMP), dichloromethane (DCM), dimethylsulfoxide (DMSO), tetrahydrofuran (THF), 1,2-dimethoxyethane (DME), high pressure liquid chromatography (HPLC), diisopropylethylamine (DIPEA), triethylamine (TEA), broad (br), singlet (s), doublet (d), triplet (t), trifluoroacetic acid (TFA), tert-butyloxycarbonyl (Boc), methanesulphonate (MsO), trifluoromethane-sulphonate (TfO), methoxyethoxymethoxy (MEMO), tetrahydropyran (THP), N-chlorosuccinimide (NCS), strong cation exchange resin (SCX), strong anion exchange resin (SAX), deuteriated DMSO (DMSO), deuteriated methanol (CD3OD), deuteriated chloroform (CDCl3), methyl (Me), ethyl (Et), isopropyl (iPr), diisopropyl azodicarboxylate (DIAD).

EXAMPLE 1

1-methyl-6-(4-(2-(piperidin-4-yl)ethoxy)-3-(trifluoromethyl)phenyl)-1H-[1,2,3]triazolo[4,5-c]pyridine-4-carbonitrile

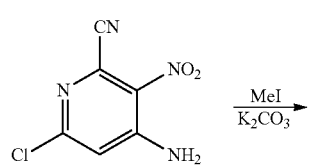

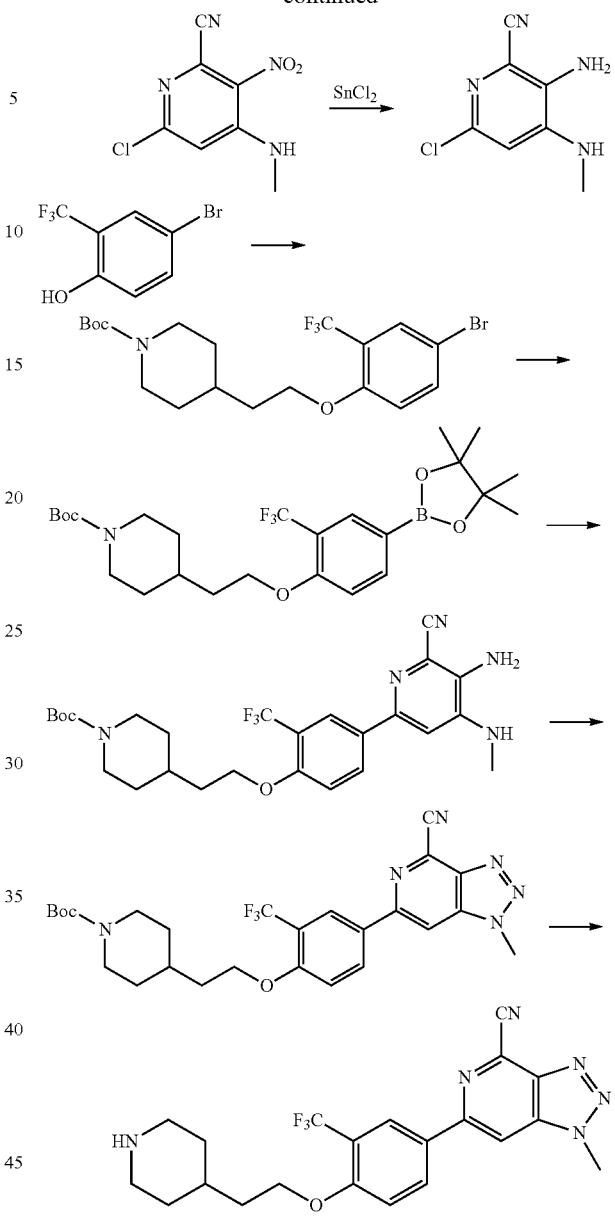

A: 6-Chloro-4-methylamino-3-nitro-pyridine-2-carbonitrile

A stirred mixture of 4-amino-6-chloro-3-nitro-pyridine-2-carbonitrile (12.5 g), potassium carbonate (17.4 g) and iodomethane (22.5 g) in acetonitrile (150 ml) was heated at 80° C. for 3 hours. At this point, another portion of iodomethane (22.5 g) was added; the mixture was heated with stirring for another 2 hours. The mixture was then diluted with ethyl acetate (500 ml) and washed with water (150 ml). The organic layer was then dried over sodium sulphate, solvent removed under reduced pressure to give expected product 4-methylamino-6-chloro-3-nitro-pyridine-2-carbonitrile (13 g).

$^1$H NMR (CD3OD) δ: 7.2 (s, 1H), 3.02 (s, 3H). MS m/z 213 (M+H).

B: 3-Amino-6-chloro-4-methylamino-pyridine-2-carbonitrile

Tin(II) chloride dihydrate (21 g) was added to a suspension of 6-chloro-4-methylamino-3-nitro-pyridine-2-carbonitrile (6.6 g) in ethanol (150 ml). The mixture was stirred at room temperature for 3 hours. To above red-brown coloured solution was then added ethyl actetate (1000 ml) and followed by 10% aqueous ammonium hydroxide (200 ml). The organic layer were separated, the sticky solid pad was washed with ethyl acetate (5×200 ml). Combined organic layer was then washed with saturated sodium chloride aqueous solution (2×200 ml), dried over sodium sulphate, solvent removed to give a brown solid as expected product (5.7 g). $^1$H NMR (CD3OD) δ: 6.45 (s, 1H), 2.89 (s, 3H).

C: tert-butyl 4-(2-(4-bromo-2-(trifluoromethyl)phenoxy)ethyl)piperidine-1-carboxylate DIAD (33.5 g) was added dropwise to the solution of triphenylphosphine (43.5 g), 4-bromo-2-trifluoromethylphenol (40 g) and tert-butyl 4-(2-hydroxyethyl)-piperidine-1-carboxylate (31.7 g) in DCM (200 ml) at 0° C. during 15 minutes. The mixture was then stirred at room temperature for 20 hours. After removal of DCM under reduced pressure, to the residue was added ether (100 ml) and heptane (300 ml), solid was then filtered off. Filtrate was then washed with 1M sodium hydroxide (100 ml×3). Organic layer dried over sodium sulphate, solvent removed under vacuum, residue was then columned on silica gel using heptane:EtOAc (5:1) as eluant to give tert-butyl 4-(2-(4-bromo-2-(trifluoromethyl)phenoxy)ethyl)piperidine-1-carboxylate as a colorless oil as product (61.3 g).
$^1$H NMR (CDCl3) δ: 7.70 (s, 1H), 7.55 (d, 1H), 6.86 (d, 1H), 4.0-4.2 (m, 4H), 2.7 (m, 2H), 1.65-1.8 (m, 5H), 1.45 (s, 9H), 1.15 (m, 2H).

D: tert-butyl 4-(2-(4-(4,4,5,5-tetramethyl-1,3,2-dioxaborolan-2-yl)-2-(trifluoromethyl)-phenoxy)ethyl)piperidine-1-carboxylate The mixture of tert-butyl 4-(2-(4-bromo-2-(trifluoromethyl)phenoxy)ethyl)-piperidine-1-carboxylate (61.3 g), 4,4,4',4',5,5,5',5'-octamethyl-2,2'-bi(1,3,2-dioxaborolane) (41.3 g), 1,1'-bis(diphenylphosphino)ferrocene-palladium dichloride (4.9 g) and potassium acetate (26.6 g) in DMSO (dry, 300 ml) was heated at 80° C. under nitrogen for 3 hours. After cooling, the mixture was diluted with ethyl acetate (1 L) and washed with water (500 ml+200 ml×4). Organic layer was dried over sodium sulphate, solvent removed and residue columned on silica gel using heptane:EtOAc (6:1) as eluant to give tert-butyl 4-(2-(4-(4,4,5,5-tetramethyl-1,3,2-dioxaborolan-2-yl)-2-(trifluoromethyl)phenoxy)ethyl)piperidine-1-carboxylate as an colourless oil (67 g).
$^1$H NMR (CDCl3) δ: 8.0 (s, 1H), 7.90 (d, 1H), 6.96 (d, 1H), 4.0-4.2 (m, 4H), 2.7 (m, 2H), 1.65-1.8 (m, 5H), 1.45 (s, 9H), 1.34 (s, 12H), 1.15 (m, 2H).

E: tert-butyl 4-(2-(4-(5-amino-6-cyano-4-(methylamino)pyridin-2-yl)-2-(trifluoromethyl)phenoxy)ethyl)piperidine-1-carboxylate The mixture of tert-butyl 4-(2-(4-(4,4,5,5-tetramethyl-1,3,2-dioxaborolan-2-yl)-2-(trifluoromethyl)phenoxy)ethyl)piperidine-1-carboxylate (2.41 g), 3-amino-6-chloro-4-(methylamino)picolinonitrile (0.8 g), tris(dibenzylideneacetone)dipalladium (201 mg), tricyclohexylphosphine (147 mg) in a mixed solvent of dioxane (30 ml) and water (15 ml) was heated under nitrogen at 100° C. for 3 hours. After cooling to room temperature, the mixture extracted with ethyl acetate (200 ml), organic layer dried over sodium sulphate, solvent removed under reduced pressure, residue was columned on silica gel using 20:1 DCM:MeOH as eluant to give tert-butyl 4-(2-(4-(5-amino-6-cyano-4-(methylamino)pyridin-2-yl)-2-(trifluoromethyl)phenoxy)ethyl)-piperidine-1-carboxylate (1.6 g) as a brown solid.
$^1$H NMR (CDCl3) δ: 8.05-8.12 (m, 2H), 7.04 (d, 1H), 6.90 (s, 1H), 4.30 (br, 1H), 4.05-4.2 (m, 4H), 4.86 (s, 2H), 3.01 (d, 3H), 2.72 (t, br, 2H), 1.7-1.9 (m, 5H), 1.46 (s, 9H), 1.15 (m, 2H).

F: tert-butyl 4-(2-(4-(4-cyano-1-methyl-1H-[1,2,3]triazolo[4,5-c]pyridin-6-yl)-2-(trifluoromethyl)phenoxy)ethyl)piperidine-1-carboxylate To tert-butyl 4-(2-(4-(5-amino-6-cyano-4-(methylamino)pyridin-2-yl)-2-(trifluoromethyl)phenoxy)ethyl)piperidine-1-carboxylate (1.8 g) in NMP (20 ml) was added 1M hydrochloric acid (15 ml) and cooled to 5-10° C. with an ice bath. To above solution was then added dropwise a solution of sodium nitrite (0.335 g) in water (3 ml) during 2 minutes. The mixture was stirred further at room temperature for another 1 hour. After adding ethyl acetate (200 ml), the mixture washed with water (4×100 ml), brine (50 ml), solvent removed under reduced pressure and residue was columned on silica gel using 2:1 EtOAc:Heptane as eluant to give tert-butyl 4-(2-(4-(4-cyano-1-methyl-1H-[1,2,3]triazolo[4,5-c]pyridin-6-yl)-2-(trifluoromethyl)phenoxy)ethyl)-piperidine-1-carboxylate (1.55 g) as a white solid.
$^1$H NMR (CDCl$_3$) δ: 8.34 (d, 1H), 8.28 (s, 1H), 7.96 (s, 1H), 7.14 (d, 1H), 4.43 (s, 3H), 4.21 (t, 2H), 4.13 (m, 2H), 2.72 (m, 2H), 1.7-1.9 (m, 5H), 1.46 (s, 9H), 1.15 (m, 2H).
MS m/z 531 (M+H).

G: 1-methyl-6-(4-(2-(piperidin-4-yl)ethoxy)-3-(trifluoromethyl)phenyl)-1H-[1,2,3]triazolo[4,5-c]pyridine-4-carbonitrile TFA salt To tert-butyl 4-(2-(4-(4-cyano-1-methyl-1H-[1,2,3]triazolo[4,5-c]pyridin-6-yl)-2-(trifluoromethyl)phenoxy)ethyl) piperidine-1-carboxylate (6 g) in DCM (40 ml) and acetonitrile (20 ml) was added TFA (40 ml). The mixture was stirred at room temperature for 10 minutes, then solvent removed under vacuum. To the residue was then dissolved ethyl acetate (40 ml) and product was precipitated by adding ether (50 ml) and collected by filtration (6.05 g as TFA salt).
$^1$H NMR (CD3OD) δ: 8.56 (s, 1H), 8.44 (s, 1H), 8.42 (d, 1H), 7.36 (d, 1H), 4.45 (s, 3H), 4.29 (t, 2H), 3.42 (m, 2H), 3.0 (td, 2H), 2.05 (m, 2H), 1.95 (m, 1H), 1.90 (m, 2H), 1.50 (m, 2H). MS m/z 431 (M+H).

EXAMPLE 2a 6-(4-(2-(1-(2-dimethylamino-2-oxoethyl)piperidin-4-yl)ethoxy)-3-(trifluoromethyl)-phenyl)-1-methyl-1H-[1,2,3]triazolo[4,5-c]pyridine-4-carbonitrile hydrochloride

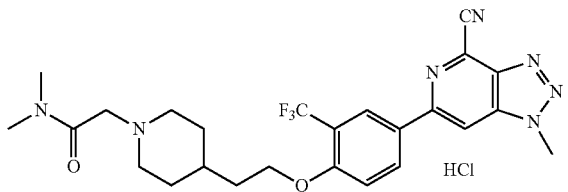 [SMILES: CN(C)C(=O)CN1CCC(CCOc2ccc(-c3cc4c(nnn4C)c(C#N)n3)cc2C(F)(F)F)CC1 ; Cl]

To 1-methyl-6-(4-(2-(piperidin-4-yl)ethoxy)-3-(trifluoromethyl)phenyl)-1H-[1,2,3]triazolo[4,5-c]pyridine-4-carbonitrile TFA salt (150 mg) in methanol (2 ml) was added 2-chloro-N,N-dimethylacetamide (67 mg) and DIPEA (0.23 ml). The mixture was heated at 90° C. for 40 minutes, then purified by basic HPLC to give 6-(4-(2-(1-(2-dimethylamino-2-oxoethyl)-piperidin-4-yl)ethoxy)-3-(trifluoromethyl)phenyl)-1-methyl-1H-[1,2,3]triazolo[4,5-c]pyridine-4-carbonitrile which was then converted to HCl salt by lypholising with 1M hydrochloric acid (1 ml) (130 mg).

$^1$H NMR (CD3OD) δ: 8.60 (s, 1H), 8.4-8.5 (m, 2H), 7.38 (d, 1H), 4.45 (s, 3H), 4.30 (t, 2H), 4.20 (s, 2H), 3.65 (m, 2H), 3.05 (m, 2H), 3.00 (s, 6H), 2.10 (m, 2H), 2.0 (m, 1H), 1.90 (m, 2H), 1.65 (m, 2H). MS m/z 516 (M+H).

The procedure described in Example 2a was further applied, using the appropriate alkylating agent, to prepare the following compounds:

2b: 1-methyl-6-(4-(2-(1-(2-methylamino-2-oxoethyl)piperidin-4-yl)ethoxy)-3-(trifluoromethyl)phenyl)-1H-[1,2,3]triazolo[4,5-c]pyridine-4-carbonitrile TFA salt

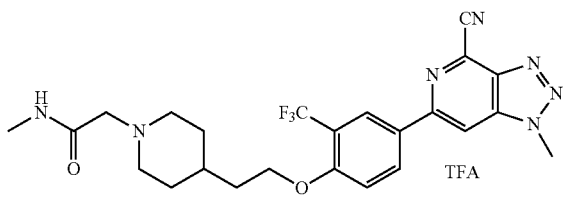 [SMILES: CNC(=O)CN1CCC(CCOc2ccc(-c3cc4c(nnn4C)c(C#N)n3)cc2C(F)(F)F)CC1 ; "TFA"]

$^1$H NMR (CD3OD) δ: 8.57 (s, 1H), 8.45 (s, 1H), 8.42 (d, 1H), 7.38 (d, 1H), 4.45 (s, 3H), 4.30 (t, 2H), 3.89 (s, 2H), 3.65 (m, 2H), 3.05 (m, 2H), 2.80 (s, 3H), 2.10 (m, 2H), 1.85-2.08 (m, 3H), 1.70 (m, 2H). MS m/z 502 (M+H).

2c: 6-(4-(2-(1-(2-amino-2-oxoethyl)piperidin-4-yl)ethoxy)-3-(trifluoromethyl)phenyl)-1-methyl-1H-[1,2,3]triazolo[4,5-c]pyridine-4-carbonitrile

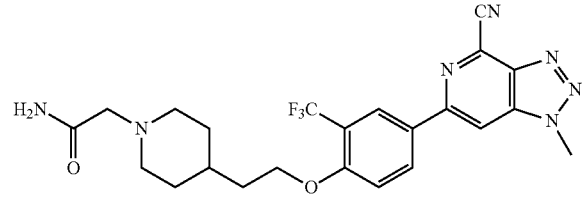 [SMILES: Cn1nnc2c(C#N)nc(-c3ccc(OCCC4CCN(CC(N)=O)CC4)c(C(F)(F)F)c3)cc21]

$^1$H NMR (DMSO-d6) δ: 8.95 (s, 1H), 8.48 (d, 1H), 8.44 (s, 1H), 7.50 (d, 1H), 7.05)br, 2H) 4.46 (s, 3H), 4.27 (t, 2H), 2.81 (s, 2H), 2.79 (m, 2H), 2.02 (td, 2H), 1.6-1.8 (m, 4H), 1.5 (m, 1H), 1.3 (m, 2H). MS m/z 488 (M+H).

2d: 6-(4-(2-(1-(2-hydroxy-2-methylpropyl)piperidin-4-yl)ethoxy)-3-(trifluoromethyl)phenyl)-1-methyl-1H-[1,2,3]triazolo-[4,5-c]pyridine-4-carbonitrile hydrochloride

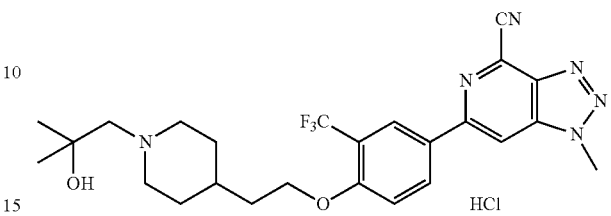

$^1$H NMR (CD3OD) δ: 8.59 (s, 1H), 8.46 (s, 1H), 8.44 (d, 1H), 7.39 (d, 1H), 4.45 (s, 3H), 4.30 (t, 2H), 3.77 (m, 2H), 3.12 (s, 2H), 3.05 (m, 2H), 1.8-2.2 (m, 5H), 1.7 (m, 2H), 1.34 (s, 6H). MS m/z 503 (M+H).

2e: 6-(4-(2-(1-(2-hydroxyethyl)piperidin-4-yl)ethoxy)-3-(trifluoromethyl)phenyl)-1-methyl-1H-[1,2,3]triazolo[4,5-c]pyridine-4-carbonitrile

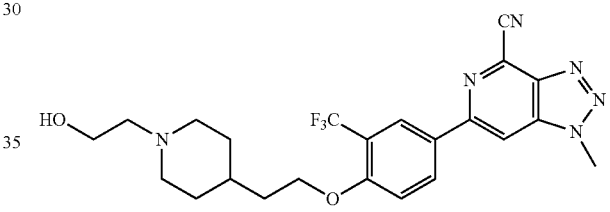

$^1$H NMR (CD3OD) δ: 8.32 (d, 1H), 8.26 (s, 1H), 7.94 (s, 1H), 7.16 (d, 1H), 4.43 (s, 3H), 4.20 (t, 2H), 3.62 (t, 2H), 3.12 (s, 2H), 2.95 (m, 2H), 2.55 (t, 2H), 2.1 (t, 2H), 1.45-1.9 (m, 5H), 1.34 (m, 2H). MS m/z 475 (M+H).

2f: 6-(4-(2-(1-(2-hydroxy-2-methyl-3,3,3-trifluoropropyl)piperidin-4-yl)ethoxy)-3-(trifluoromethyl)phenyl)-1-methyl-1H-[1,2,3]triazolo[4,5-c]pyridine-4-carbonitrile

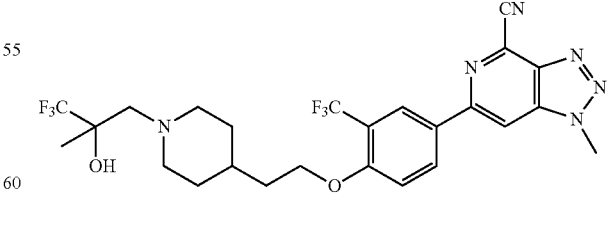

$^1$H NMR (CD3OD) δ: 8.32 (d, 1H), 8.26 (s, 1H), 7.94 (s, 1H), 7.13 (d, 1H), 4.43 (s, 3H), 4.19 (t, 2H), 2.75-2.95 (m, 3H), 2.3-2.5 (m, 3H), 1.4-1.9 (m, 5H), 1.35 (m, 2H), 1.31 (s, 3H). MS m/z 557 (M+H).

EXAMPLE 3a 1-methyl-6-(4-(2-(1-(oxazol-2-ylmethyl)piperidin-4-yl)ethoxy)-3-(trifluoromethyl)phenyl)-1H-[1,2,3]triazolo[4,5-c]pyridine-4-carbonitrile

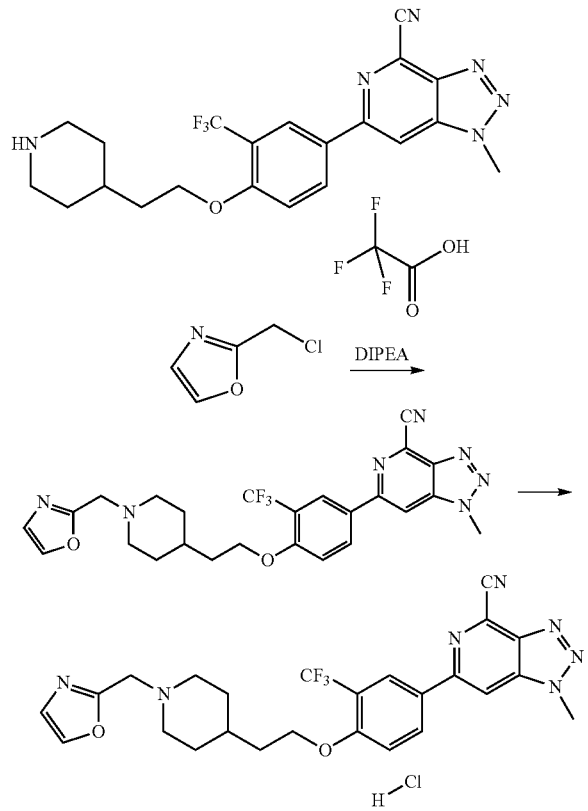

2-(Chloromethyl)oxazole (21.59 mg) was added to a solution containing 1-methyl-6-(4-(2-(piperidin-4-yl)ethoxy)-3-(trifluoromethyl)phenyl)-1H-[1,2,3]triazolo[4,5-c]pyridine-4-carbonitrile 2,2,2-trifluoroacetate (50 mg), and diisopropyethylamine (0.076 ml, 59.3 mg) dissolved in Acetonitrile (1 ml). Reaction was heated at 100° C. under microwave condition for 15 minutes. Solvent removed under reduced pressure, crude residue dissolved in dichloromethane (1 ml) and 1 ml water added. Mixture was filtered though a hydrophobic fret and dichloromethane removed in vacuo. Sample purified by basic prep LCMS to afford free base 1-methyl-6-(4-(2-(1-(oxazol-2-ylmethyl)piperidin-4-yl)ethoxy)-3-(trifluoromethyl)phenyl)-1H-[1,2,3]triazolo[4,5-c]pyridine-4-carbonitrile. HCl salt formed by adding 0.98 ml 0.5M HCl (aq) to sample and lyophilising sample in genevac to give 1-methyl-6-(4-(2-(1-(oxazol-2-ylmethyl)piperidin-4-yl)ethoxy)-3-(trifluoromethyl)phenyl)-1H-[1,2,3]triazolo[4,5-c]pyridine-4-carbonitrile hydrochloride (25.6 mg).
$^1$H NMR (MEOD) δ: 8.75 (s, 1H), 8.45 (m, 2H), 8.06 (s, 1H), 7.35 (d, 1H), 7.32 (s, 1H), 4.54 (broad s, 2H), 4.45 (s, 3H), 4.29 (t, 2H), 3.62 (broad m, 2H), 3.13 (broad m, 2H), 2.14 (broad d, 2H), 1.90 (broad m, 3H), 1.59 (broad m, 2H). MS m/z 512.2 (M+H).

The procedure described in Example 3a was further applied, using the appropriate alkylation reagent, to prepare the following compounds as free bases or hydrochloric acid salt:

3b: 6-(4-(2-(1-((3,5-dimethylisoxazol-4-yl)methyl)piperidin-4-yl)ethoxy)-3-(trifluoromethyl)phenyl)-1-methyl-1H-[1,2,3]triazolo[4,5-c]pyridine-4-carbonitrile

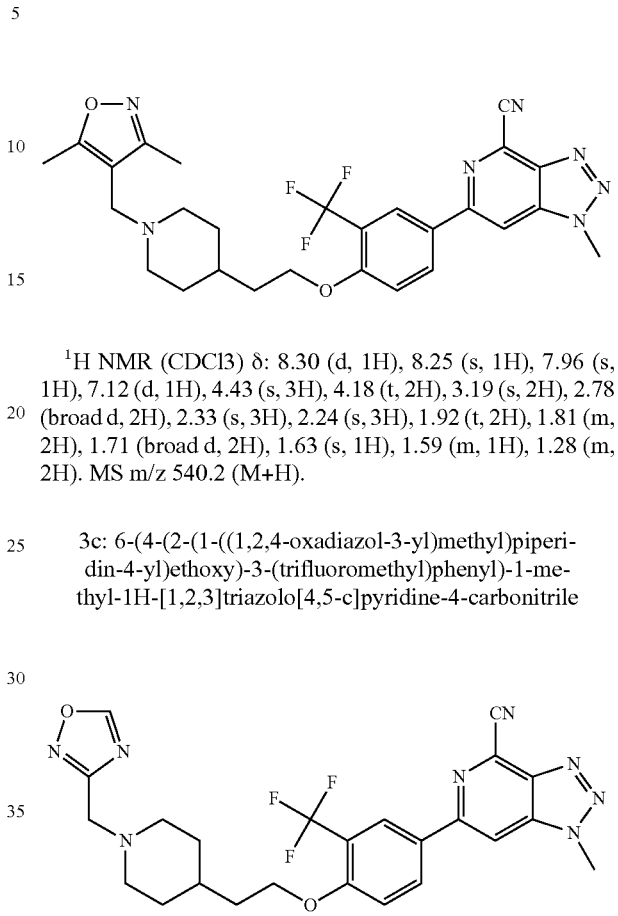

$^1$H NMR (CDCl3) δ: 8.30 (d, 1H), 8.25 (s, 1H), 7.96 (s, 1H), 7.12 (d, 1H), 4.43 (s, 3H), 4.18 (t, 2H), 3.19 (s, 2H), 2.78 (broad d, 2H), 2.33 (s, 3H), 2.24 (s, 3H), 1.92 (t, 2H), 1.81 (m, 2H), 1.71 (broad d, 2H), 1.63 (s, 1H), 1.59 (m, 1H), 1.28 (m, 2H). MS m/z 540.2 (M+H).

3c: 6-(4-(2-(1-((1,2,4-oxadiazol-3-yl)methyl)piperidin-4-yl)ethoxy)-3-(trifluoromethyl)phenyl)-1-methyl-1H-[1,2,3]triazolo[4,5-c]pyridine-4-carbonitrile $^1$H NMR (CDCl3) δ: 8.69 (s, 1H), 8.31 (d, 1H), 8.25 (s, 1H), 7.14 (d, 1H), 4.43 (s, 3H), 4.18 (t, 2H), 3.76 (s, 2H), 2.99 (broad d, 2H), 2.18 (t, 2H), 1.84-1.74 (broad m, 4H), 1.63 (m, 1H), 1.41 (d, 2H). MS m/z 513.2 (M+H).

3d: 1-methyl-6-(4-(2-(1-((5-methylisoxazol-3-yl)methyl)piperidin-4-yl)ethoxy)-3-(trifluoromethyl)phenyl)-1H-[1,2,3]triazolo[4,5-c]pyridine-4-carbonitrile

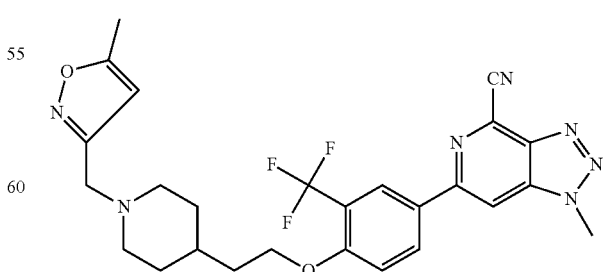

$^1$H NMR (CDCl3) δ: 8.21 (d, 1H), 8.25 (s, 1H), 7.12 (d, 1H), 5.99 (s, 1H), 4.43 (s, 3H), 4.18 (t, 2H), 3.54 (s, 2H), 2.88

(d, 2H), 2.40 (s, 3H), 2.07 (t, 2H), 1.81 (m, 2H), 1.73 (broad d, 2H), 1.56 (m, 1H), 1.36 (m, 2H). MS m/z 526.2 (M+H).

3e: 1-methyl-6-(4-(2-(1-((5-methyl-1,2,4-oxadiazol-3-yl)methyl)piperidin-4-yl)ethoxy)-3-(trifluoromethyl)phenyl)-1H-[1,2,3]triazolo[4,5-c]pyridine-4-carbonitrile

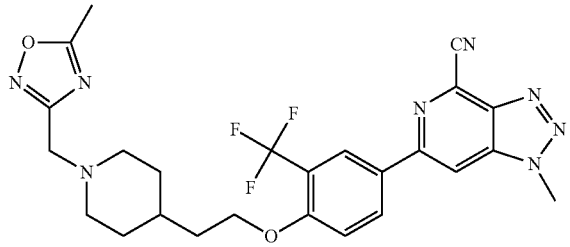 [SMILES: Cc1nc(CN2CCC(CCOc3ccc(-c4cc5c(nnn5C)c(C#N)n4)cc3C(F)(F)F)CC2)no1]

¹H NMR (CDCl3) δ: 8.30 (d, 1H), 8.25 (s, 1H), 7.95 (s, 1H), 7.14 (d, 1H), 4.43 (s, 3H), 4.18 (t, 2H), 2.98 (d, 2H), 2.15 (t, 2H), 1.80 (q, 2H), 1.73 (d, 1H), 1.61 (m, 1H), 1.43 (m, 2H). MS m/z 527.2 (M+H)

3f: 1-methyl-6-(4-(2-(1-((3-methylisoxazol-5-yl)methyl)piperidin-4-yl)ethoxy)-3-(trifluoromethyl)phenyl)-1H-[1,2,3]triazolo[4,5-c]pyridine-4-carbonitrile

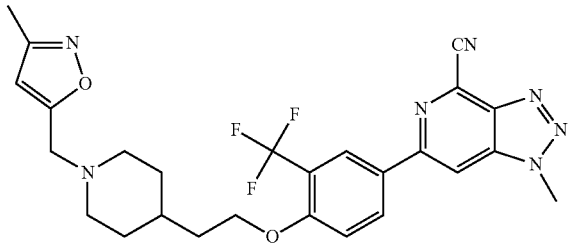 [SMILES: Cc1cc(CN2CCC(CCOc3ccc(-c4cc5c(nnn5C)c(C#N)n4)cc3C(F)(F)F)CC2)on1]

¹H NMR (CDCl3) δ: 8.32 (d, 1H), 8.25 (s, 1H), 7.95 (s, 1H), 7.12 (d, 1H), 6.00 (s, 1H), 4.43 (s, 3H), 4.17 (t, 2H), 3.63 (s, 2H), 2.90 (d, 2H), 2.29 (s, 3H), 2.13 (t, 2H), 1.84-1.74 (broad m, 4H), 1.56 (m, 1H), 1.36 (m, 2H). MS m/z 526.2 (M+H)

3g: 1-methyl-6-(4-(2-(1-((5-methyl-1,3,4-oxadiazol-2-yl)methyl)piperidin-4-yl)ethoxy)-3-(trifluoromethyl)phenyl)-1H-[1,2,3]triazolo[4,5-c]pyridine-4-carbonitrile

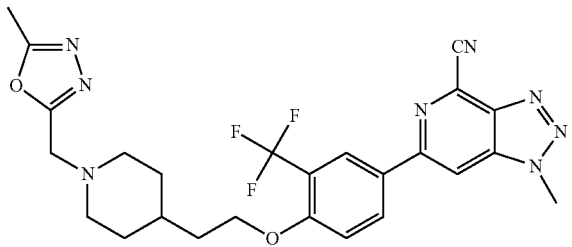 [SMILES: Cc1nnc(CN2CCC(CCOc3ccc(-c4cc5c(nnn5C)c(C#N)n4)cc3C(F)(F)F)CC2)o1]

¹H NMR (CDCl3) δ: 8.27 (m, 2H), 7.99 (s, 1H), 7.13 (d, 1H), 4.44 (s, 3H), 4.18 (t, 2H), 3.75 (s, 2H), 2.95 (d, 2H), 2.54 (s, 3H), 2.18 (t, 2H), 1.79 (m, 4H), 1.62 (m, 1H), 1.40 (m, 2H). MS m/z 527.2 (M+H)

3h: 6-(4-(2-(1-((2-isopropyloxazol-4-yl)methyl)piperidin-4-yl)ethoxy)-3-(trifluoromethyl)phenyl)-1-methyl-1H-[1,2,3]triazolo[4,5-c]pyridine-4-carbonitrile

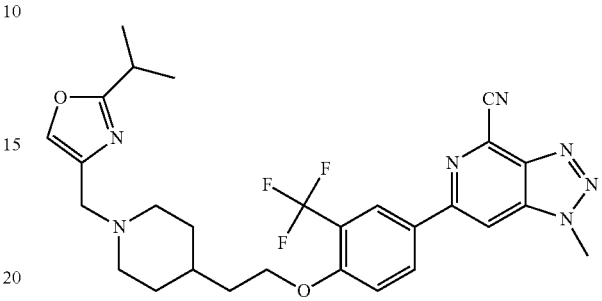

¹H NMR (CDCl3) δ: 8.26 (d, 1H), 8.24 (s, 1H), 7.96 (s, 1H), 7.40 (s, 1H), 7.13 (d, 1H), 4.43 (s, 3H), 4.18 (t, 2H), 3.42 (s, 2H), 3.07 (m, 1H), 2.95 (d, 2H), 2.03 (t, 2H), 1.83-1.72 (broad m, 4H), 1.59 (m, 2H), 1.32 (d, 6H). MS m/z 554.2 (M+H)

3i: 6-(4-(2-(1-((5-isopropylisoxazol-3-yl)methyl)piperidin-4-yl)ethoxy)-3-(trifluoromethyl)phenyl)-1-methyl-1H-[1,2,3]triazolo[4,5-c]pyridine-4-carbonitrile

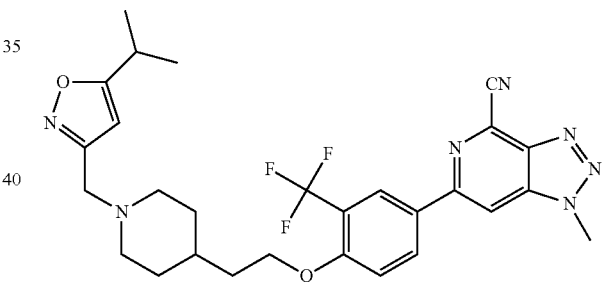

¹H NMR (CDCl3) δ: 8.30 (d, 1H), 8.24 (s, 1H), 7.12 (d, 1H), 5.98 (s, 1H), 4.43 (s, 3H), 4.18 (t, 2H), 3.54 (s, 2H), 3.05 (m, 1H), 2.89 (d, 2H), 2.07 (t, 2H), 1.84-1.74 (broad m, 4H), 1.58 (m, 1H), 1.35 (m, 2H), 1.31 (d, 6H). MS m/z 554.2 (M+H)

3j: 6-(4-(2-(1-((3-ethyl-1,2,4-oxadiazol-5-yl)methyl)piperidin-4-yl)ethoxy)-3-(trifluoromethyl)phenyl)-1-methyl-1H-[1,2,3]triazolo[4,5-c]pyridine-4-carbonitrile

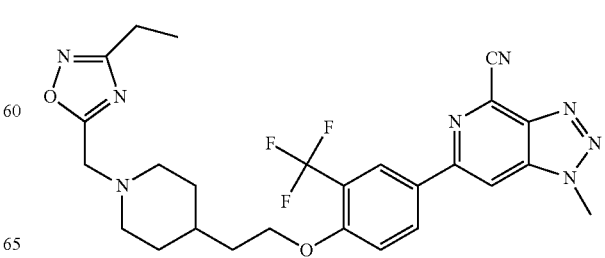

¹H NMR (CDCl3) δ: 8.29 (d, 1H), 8.24 (s, 1H), 7.95 (s, 1H), 7.14 (d, 1H), 4.43 (s, 3H), 4.18 (t, 2H), 3.81 (s, 2H), 2.98 (d, 2H), 2.77 (q, 2H), 2.21 (t, 2H), 1.85-1.75 (broad m, 4H), 1.58 (m, 1H), 1.41 (m, 2H), 1.34 (t, 3H). MS m/z 541.2 (M+H)

3k: 6-(4-(2-(1-((1,2,4-oxadiazol-5-yl)methyl)piperidin-4-yl)ethoxy)-3-(trifluoromethyl)phenyl)-1-methyl-1H-[1,2,3]triazolo[4,5-c]pyridine-4-carbonitrile

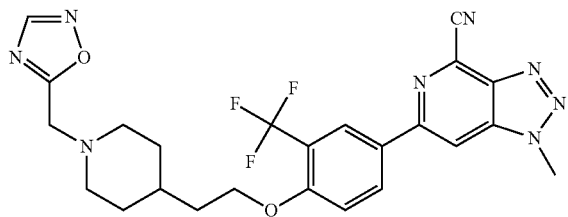 [SMILES: Cn1nnc2c(C#N)nc(-c3ccc(OCCC4CCN(Cc5ncno5)CC4)c(C(F)(F)F)c3)cc21]

¹H NMR (CDCl3) δ: 8.69 (s, 1H), 8.25 (m, 2H), 7.95 (s, 1H), 7.13 (d, 1H), 4.43 (s, 3H), 4.18 (t, 2H), 3.76 (s, 2H), 2.96 (d, 2H), 2.18 (t, 2H), 1.82-1.74 (broad m, 4H), 1.59 (m, 1H), 1.40 (m, 2H). MS m/z 513.2 (M+H)

EXAMPLE 4a 1-methyl-6-(4-(2-(1-(pyridin-2-yl)piperidin-4-yl)ethoxy)-3-(trifluoromethyl)phenyl)-1H-[1,2,3]triazolo[4,5-c]pyridine-4-carbonitrile hydrochloride

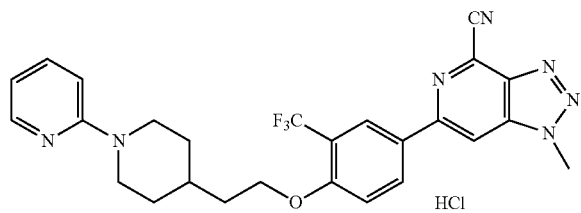 [SMILES: Cn1nnc2c(C#N)nc(-c3ccc(OCCC4CCN(c5ccccn5)CC4)c(C(F)(F)F)c3)cc21 ; Cl]

To 1-methyl-6-(4-(2-(piperidin-4-yl)ethoxy)-3-(trifluoromethyl)phenyl)-1H-[1,2,3]triazolo[4,5-c]pyridine-4-carbonitrile TFA salt (170 mg) in DMSO (2 ml) was added 2-fluoropyridine (121 mg) and TEA (0.22 ml). The mixture was heated at 200° C. for 40 minutes, then purified by basic HPLC to give 1-methyl-6-(4-(2-(1-(pyridin-2-yl)piperidin-4-yl)ethoxy)-3-(trifluoromethyl)phenyl)-1H-[1,2,3]triazolo[4,5-c]pyridine-4-carbonitrile which was then converted to HCl salt by lypholising with 1M hydrochloric acid (1 ml) (50 mg).

¹H NMR (CD3OD) δ: 8.57 (s, 1H), 8.45 (s, 1H), 8.44 (d, 1H), 8.0 (m, 1H), 7.9 (d, 1H), 7.35-7.45 (m, 2H), 6.95 (t, 1H), 4.45 (s, 3H), 4.31 (t, 2H), 4.22 (m, 2H), 3.3 (m, 2H), 2.0-2.2 (m, 3H), 1.90 (m, 2H), 1.49 (m, 2H). MS m/z 508 (M+H).

The procedure described in Example 4a was further applied, using the appropriate aryl or heteroaryl halide, to prepare the following compounds:

4b: 1-methyl-6-(4-(2-(1-(6-methylpyridin-2-yl)piperidin-4-yl)ethoxy)-3-(trifluoromethyl)phenyl)-1H-[1,2,3]triazolo[4,5-c]pyridine-4-carbonitrile hydrochloride

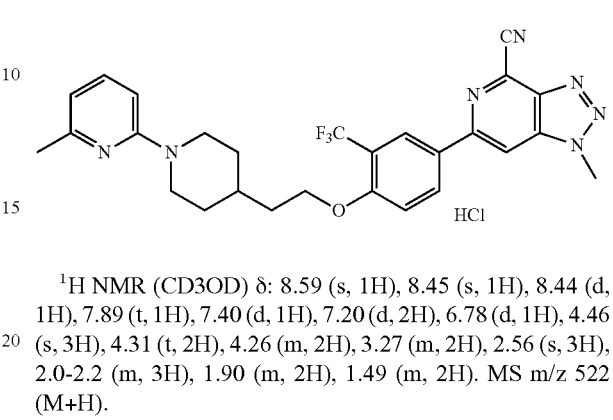

¹H NMR (CD3OD) δ: 8.59 (s, 1H), 8.45 (s, 1H), 8.44 (d, 1H), 7.89 (t, 1H), 7.40 (d, 1H), 7.20 (d, 2H), 6.78 (d, 1H), 4.46 (s, 3H), 4.31 (t, 2H), 4.26 (m, 2H), 3.27 (m, 2H), 2.56 (s, 3H), 2.0-2.2 (m, 3H), 1.90 (m, 2H), 1.49 (m, 2H). MS m/z 522 (M+H).

4c: 6-(4-(2-(1-(3-cyanopyridin-2-yl)piperidin-4-yl)ethoxy)-3-(trifluoromethyl)phenyl)-1-methyl-1H-[1,2,3]triazolo[4,5-c]pyridine-4-carbonitrile

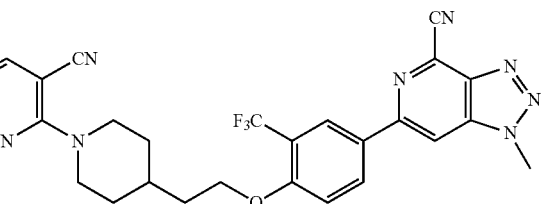

¹H NMR (CD3OD) δ: 8.57 (s, 1H), 8.45 (s, 1H), 8.44 (d, 1H), 8.34 (d, 1H), 7.89 (t, 1H), 7.40 (d, 1H), 6.82 (t, 1H), 4.45 (s, 3H), 4.3-4.4 (m, 4H), 3.05 (t, 2H), 1.85-2.0 (m, 5H), 1.49 (m, 2H). MS m/z 533 (M+H).

4d: 6-(4-(2-(1-(3-fluoropyridin-2-yl)piperidin-4-yl)ethoxy)-3-(trifluoromethyl)phenyl)-1-methyl-1H-[1,2,3]triazolo[4,5-c]pyridine-4-carbonitrile

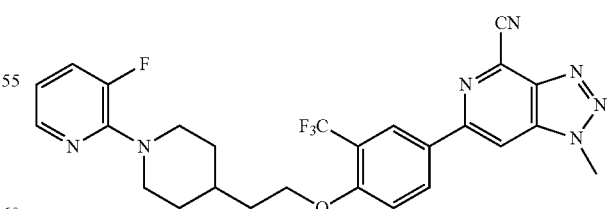

¹H NMR (CD3OD) δ: 8.57 (s, 1H), 8.45 (s, 1H), 8.44 (d, 1H), 7.92 (d, 1H), 7.45 (dd, 1H), 7.40 (d, 1H), 6.86 (m, 1H), 4.45 (s, 3H), 4.30 (t, 2H), 4.05 (m, 2H), 2.95 (t, 2H), 1.85-2.0 (m, 5H), 1.49 (m, 2H). MS m/z 526 (M+H).

4e: 6-(4-(2-(1-(5-fluoropyridin-2-yl)piperidin-4-yl)ethoxy)-3-(trifluoromethyl)phenyl)-1-methyl-1H-[1,2,3]triazolo[4,5-c]pyridine-4-carbonitrile

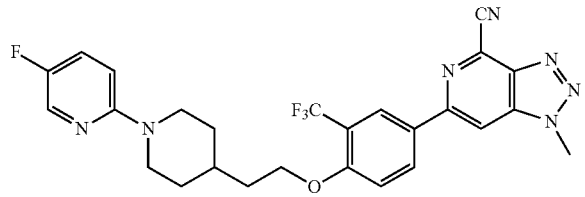 [SMILES: Cn1nnc2c(C#N)nc(-c3ccc(OCCC4CCN(c5ccc(F)cn5)CC4)c(C(F)(F)F)c3)cc21]

¹H NMR (CD3OD) δ: 8.56 (s, 1H), 8.44 (s, 1H), 8.42 (d, 1H), 7.95 (d, 1H), 7.70 (m, 1H), 7.38 (d, 1H), 7.17 (dd, 1H), 4.45 (s, 3H), 4.30 (t, 2H), 4.22 (m, 2H), 3.10 (t, 2H), 1.85-2.1 (m, 5H), 1.45 (m, 2H). MS m/z 526 (M+H).

4f: 1-methyl-6-(4-(2-(1-(quinolin-2-yl)piperidin-4-yl)ethoxy)-3-(trifluoromethyl)phenyl)-1H-[1,2,3]triazolo[4,5-c]pyridine-4-carbonitrile TFA salt

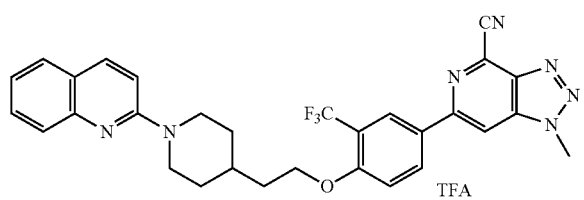 [SMILES: Cn1nnc2c(C#N)nc(-c3ccc(OCCC4CCN(c5ccc6ccccc6n5)CC4)c(C(F)(F)F)c3)cc21 ; "TFA"]

¹H NMR (CD3OD) δ: 8.57 (s, 1H), 8.46 (s, 1H), 8.42 (d, 1H), 8.38 (d, 1H), 7.9 (m, 2H), 7.8 (t, 1H), 7.53 (t, 1H), 7.49 (d, 1H), 7.39 (d, 1H), 4.50 (m, 2H), 4.45 (s, 3H), 4.33 (t, 2H), 3.47 (t, 2H), 2.1-2.25 (m, 3H), 1.92 (m, 2H), 1.55 (m, 2H). MS m/z 558 (M+H).

EXAMPLE 5

6-(4-((2-methoxyethoxy)methoxy)-3-(trifluoromethyl)phenyl)-1-methyl-1H-[1,2,3]triazolo[4,5-c]pyridine-4-carbonitrile

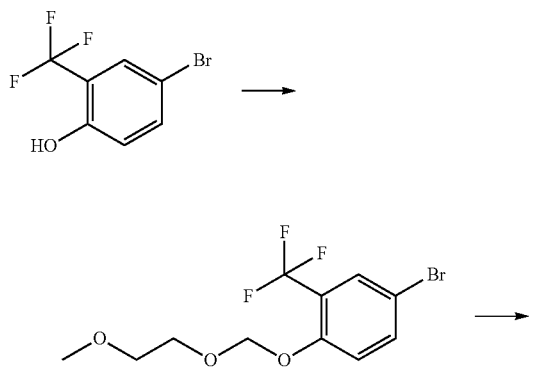

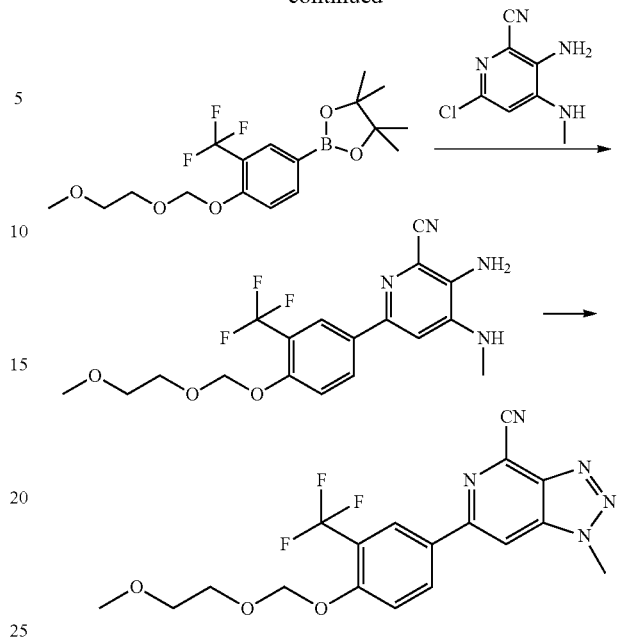

A: 4-bromo-1-((2-methoxyethoxy)methoxy)-2-(trifluoromethyl)benzene

Sodium hydride (6.55 g) was added in small portions to a solution of 4-bromo-2-(trifluoromethyl)phenol (32.9 g) in THF (150 ml). After stirring at room temperature for 10 minutes, 1-(chloromethoxy)-2-methoxyethane (17 g) was then added by syringe. The mixture was stirred at room temperature for 24 hours then diluted with ethyl acetate (300 mL) and washed with water. Organics were dried over sodium sulphate and solvent evaporated under reduced pressure. The resulting residue was columned on silica gel using heptane as eluant to afford 4-bromo-1-((2-methoxy-ethoxy)methoxy)-2-(trifluoromethyl)benzene (78% yield).

¹H NMR (CDCl3) δ: 7.70 (s, 1H), 7.55 (d, 1H), 7.20 (d, 1H), 5.34 (s, 2H), 3.82 (t, 2H), 3.54 (t, 2H), 3.36 (s, 3H).

B: 2-(4-((2-methoxyethoxy)methoxy)-3-(trifluoromethyl)phenyl)-4,4,5,5-tetramethyl-1,3,2-dioxaborolane 4-Bromo-1-((2-methoxyethoxy)methoxy)-2-(trifluoromethyl)benzene (6.33 g) bis(pinacolato)diboron (23.08 mmol, 5.86 g), 1,1'-bis(diphenylphosphino)-ferrocenedichloropalladium(II) (0.696 g) and potassium acetate (3.78 g) were suspended in DMSO (71 ml) and heated to 80° C. under a nitrogen for 3 hours. After cooling to room temperature the reaction mixture was diluted with EtOAc (300 ml) filtered through celite and washed with water (3×200 ml) and brine. Organics were dried over sodium sulphate and solvent evaporated under reduced pressure to yield crude product as a brown oil. Purification by flash chromatography (340 g silica column, 10% to 25% EtOAc/heptane gradient) afforded 2-(4-((2-methoxyethoxy)-methoxy)-3-(trifluoromethyl)phenyl)-4,4,5,5-tetramethyl-1,3,2-dioxaborolane (54% yield) as a clear oil.

¹H NMR (CDCl3) δ: 8.05 (s, 1H), 7.90 (d, 1H), 7.22 (d, 1H), 5.39 (s, 2H), 3.80 (t, 2H), 3.55 (t, 2H), 3.36 (s, 3H), 1.34 (s, 12H).

29

C: 3-amino-6-(4-((2-methoxyethoxy)methoxy)-3-(trifluoromethyl)phenyl)-4-(methylamino)picolinonitrile 2-(4-((2-Methoxyethoxy)methoxy)-3-(trifluoromethyl)phenyl)-4,4,5,5-tetramethyl-1,3,2-dioxaborolane (3.83 g), 3-amino-6-chloro-4-(methylamino)-picolinonitrile (1.55 g), tris(dibenzylideneacetone)dipalladium (0) (0.389 g), tricyclohexylphosphine (0.286 g) and potassium phosphate (3.60 g) were charged to a 100 ml flask. Dioxane (30 ml) and water (12 ml) were added and the mixture placed under a nitrogen atmosphere. The reaction was heated to 110° C. for 3 hours and allowed to stand at room temperature for 2 hours. The mixture was diluted with EtOAc (200 ml) filtered through celite, washed with water (3×200 ml), dried over sodium sulphate and then solvent was evaporated under reduced pressure to yield crude product as a brown oil. DCM was added to the residue causing a pale brown solid to crash out of solution. The mixture was filtered and the solid washed with a small amount of DCM followed by ether to afford 3-amino-6-(4-((2-methoxyethoxy)-methoxy)-3-(trifluoromethyl)phenyl)-4-(methylamino)picolinonitrile (28% yield). The liquors were purified by flash chromatography (340 g silica column; 2:1, 1:1, 0:1 heptane/EtOAc mobile phase) to afford further 3-amino-6-(4-((2-methoxyethoxy)-methoxy)-3-(trifluoromethyl)phenyl)-4-(methylamino)picolinonitrile (49% yield).

$^1$H NMR (DMSO) δ 8.19 (d, 1H), 8.18 (s, 1H), 7.40 (d, 1H), 6.97 (s, 1H), 6.30 (broad m, 1H), 5.72 (broad s, 2H), 5.46 (s, 2H), 3.76 (t, 2H), 3.50 (t, 2H), 3.23 (s, 3H), 2.91 (d, 3H).

D: 6-(4-((2-methoxyethoxy)methoxy)-3-(trifluoromethyl)phenyl)-1-methyl-1H-[1,2,3]triazolo[4,5-c]pyridine-4-carbonitrile 3-amino-6-(4-((2-methoxyethoxy)methoxy)-3-(trifluoromethyl)phenyl)-4-(methylamino)picolinonitrile (100 mg) was suspended in dioxane (1500 μl) and water (1500 μl) and cooled to 0° C. Hydrochloric acid (2M, 189 μl) followed by dropwise addition of sodium nitrite (25 mg) in water (500 μl) and the mixture stirred at room temperature for 2 hours. The suspension was filtered and the solid washed with water to afford pale brown solid 6-(4-((2-methoxyethoxy)methoxy)-3-(trifluoromethyl)-phenyl)-1-methyl-1H-[1,2,3]triazolo[4,5-c]pyridine-4-carbonitrile (92% yield).

$^1$H NMR (CDCl3) δ 8.31 (s, 1H), 8.29 (d, 1H), 7.96 (s, 1H), 7.45 (d, 1H), 5.45 (s, 2H), 4.43 (s, 3H), 3.87 (t, 2H), 3.57 (t, 2H), 3.38 (s, 3H). MS m/z 408.0 (M+H).

EXAMPLE 6

6-(4-hydroxy-3-(trifluoromethyl)phenyl)-1-methyl-1H-[1,2,3]triazolo[4,5-c]pyridine-4-carbonitrile

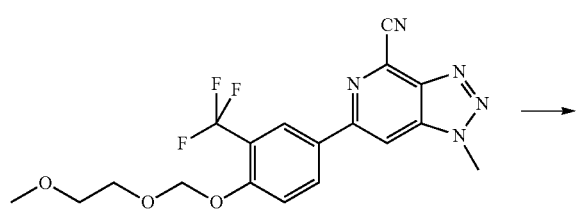

30

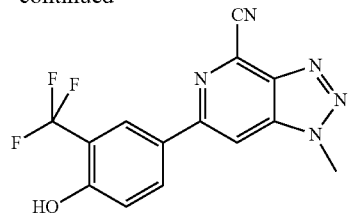

6-(4-((2-Methoxyethoxy)methoxy)-3-(trifluoromethyl)phenyl)-1-methyl-1H-[1,2,3]triazolo[4,5-c]pyridine-4-carbonitrile (6.31 mmol, 2.57 g) was dissolved in THF (42 ml) and hydrochloric acid (2M aq) (31.5 mmol, 15.77 ml) added. The mixture was heated to 65° C. for 4 hours, after which time LCMS indicated no reaction. THF (21 ml) was added and heating continued for 16 hours then EtOAc was added and the solution basified with aqueous ammonia. Organics were separated and solvent evaporated under reduced pressure. The resulting pale yellow solid was washed with EtOAc/ether (1:1) and dried to afford product 6-(4-hydroxy-3-(trifluoromethyl)-phenyl)-1-methyl-1H-[1,2,3]triazolo[4,5-c]pyridine-4-carbonitrile (82% yield). $^1$H NMR (DMSO) δ: 8.85 (s, 1H), 8.36 (s, 1H), 8.32 (d, 1H), 7.18 (d, 1H), 4.45 (s, 3H).

EXAMPLE 7a

(S)-1-methyl-6-(4-(2-(1-(pyridin-2-yl)pyrrolidin-3-yl)ethoxy)-3-(trifluoromethyl)phenyl)-1H-[1,2,3]triazolo[4,5-c]pyridine-4-carbonitrile hydrochloride

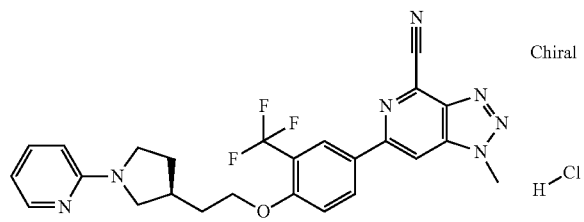

A: (S)-2-(1-(pyridin-2-yl)pyrrolidin-3-yl)ethanol (S)-2-(Pyrrolidin-3-yl)ethanol 2-fluoropyridine (6.95 mmol, 0.598 ml, 0.674 g) and triethylamine (17.36 mmol, 2.420 ml, 1.757 g) were dissolved in MeOH (2.5 ml) and heated to 150° C. for 1 hour in the microwave. TLC (permanganate stain) suggested SM remained. Further 2-fluoropyridine (6.95 mmol, 0.598 ml, 0.674 g) was added and heating continued for 1 hour. The reaction mixture was concentrated in vacuo. The resulting residue was purified by silica chromatography, eluting with DCM—3% MeOH/DCM to afford (S)-2-(1-(pyridin-2-yl)pyrrolidin-3-yl)ethanol. $^1$H NMR (CDCl3) δ: 8.14 (d, 1H), 7.44 (m, 1H), 6.51 (m, 1H), 6.33 (d, 1H), 3.71 (m, 3H), 3.55 (m, 1H), 3.38 (m, 1H), 3.05 (m, 1H), 2.42 (m, 1H), 2.17 (m, 1H), 1.78 (m, 2H), 1.66 (m, 1H).

B: (S)-1-methyl-6-(4-(2-(1-(pyridin-2-yl)pyrrolidin-3-yl)ethoxy)-3-(trifluoromethyl)-phenyl)-1H-[1,2,3]triazolo[4,5-c]pyridine-4-carbonitrile hydrochloride 6-(4-Hydroxy-3-(trifluoromethyl)phenyl)-1-methyl-1H-[1,2,3]triazolo[4,5-c]pyridine-4-carbonitrile (0.157 mmol, 50 mg) (3-isopropyl-1,2,4-oxadiazol-5-yl)-methanol (0.313 mmol, 45 mg) and triphenylphosphine (0.235 mmol, 62 mg) were dissolved in NMP (1 ml) and DIAD (0.235 mmol, 0.047 ml, 48 mg) added. The reaction was stirred at room temperature for 20 hours. The reaction was purified by preparative HPLC (acidic) followed by SCX. Solvent was evaporated under reduced pressure and the resulting residue was dissolved in a minimum volume of THF. Excess HCl (2M in ether) was added the suspension filtered and the solid washed with ether. (S)-1-methyl-6-(4-(2-(1-(pyridin-2-yl)pyrrolidin-3-yl)ethoxy)-3-(trifluoro-methyl)phenyl)-1H-[1,2,3]triazolo[4,5-c]pyridine-4-carbonitrile hydrochloride obtained as a white solid after drying. $^1$H NMR (DMSO) δ: 9.00 (s, 1H), 8.54 (d, 1H), 8.47 (s, 1H), 7.98 (m, 2H), 7.52 (d, 1H), 7.08 (d, 1H), 6.90 (t, 1H), 4.47 (s, 3H), 4.33 (t, 2H), 3.80 (m, 1H), 3.70 (m, 1H), 3.55 (m, 1H), 3.30 (m, 1H), 2.52 (m, 1H), 2.28 (m, 1H), 1.99 (m, 2H), 1.82 (m, 1H). MS m/z 492 (M+H).

The above procedure for 7a was applied to synthesise the following compounds:

7b: (R)-1-methyl-6-(4-(2-(1-(pyridin-2-yl)pyrrolidin-3-yl)ethoxy)-3-(trifluoromethyl)phenyl)-1H-[1,2,3]triazolo[4,5-c]pyridine-4-carbonitrile hydrochloride

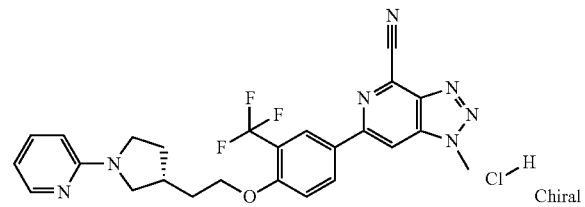

A: (R)-2-(1-(pyridin-2-yl)pyrrolidin-3-yl)ethanol $^1$H NMR (CDCl3) δ: 8.14 (d, 1H), 7.44 (m, 1H), 6.51 (m, 1H), 6.33 (d, 1H), 3.71 (m, 3H), 3.55 (m, 1H), 3.38 (m, 1H), 3.05 (m, 1H), 2.42 (m, 1H), 2.17 (m, 1H), 1.78 (m, 2H), 1.66 (m, 1H).

B: (R)-1-methyl-6-(4-(2-(1-(pyridin-2-yl)pyrrolidin-3-yl)ethoxy)-3-(trifluoromethyl)phenyl)-1H-[1,2,3]triazolo[4,5-c]pyridine-4-carbonitrile hydrochloride $^1$H NMR (DMSO) δ: 9.00 (s, 1H), 8.54 (d, 1H), 8.47 (s, 1H), 7.98 (m, 2H), 7.52 (d, 1H), 7.02 (m, 1H), 6.88 (t, 1H), 4.47 (s, 3H), 4.33 (t, 2H), 3.80 (m, 1H), 3.70 (m, 1H), 3.55 (m, 1H), 3.30 (m, 1H), 2.52 (m, 1H), 2.28 (m, 1H), 1.99 (m, 2H), 1.82 (m, 1H). MS m/z 492 (M+H).

EXAMPLE 8

1-methyl-6-(4-(2-(1-(5-methylpyridin-2-yl)piperidin-4-yl)ethoxy)-3-(trifluoromethyl)phenyl)-1H-[1,2,3]triazolo[4,5-c]pyridine-4-carbonitrile hydrochloride

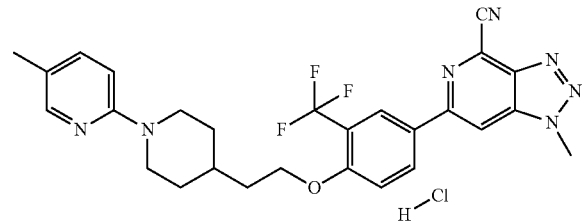

6-(4-Hydroxy-3-(trifluoromethyl)phenyl)-1-methyl-1H-[1,2,3]triazolo[4,5-c]pyridine-4-carbonitrile (7.99 mmol, 2.55 g) 2-(1-(5-methylpyridin-2-yl)piperidin-4-yl)ethanol (11.98 mmol, 2.64 g) and triphenylphosphine (15.98 mmol, 4.19 g) were suspended in DCM (26.6 ml) and DIAD (15.98 mmol, 3.15 ml, 3.23 g) added. The reaction was heated to reflux for 20 hours. The reaction mixture was concentrated under reduced pressure and purified by flash chromatography (100 g silica column, heptane to 1:1 heptane/EtOAc gradient). Solvent was evaporated from the appropriate fractions and the residue was suspended in a small volume of THF, sonicated and heated to 50 C. for 10 minutes. The suspension was filtered and the resulting white solid lyophilised in a genevac with 0.5M HCl followed by water. Product 1-methyl-6-(4-(2-(1-(5-methylpyridin-2-yl)piperidin-4-yl)ethoxy)-3-(trifluoromethyl)phenyl)-1H-[1,2,3]triazolo[4,5-c]pyridine-4-carbonitrile hydrochloride (46.0% yield) obtained. $^1$H NMR (DMSO) δ: 8.96 (s, 1H), 8.50 (d, 1H), 8.40 (s, 1H), 7.82 (m, 2H), 7.85 (d, 1H), 7.50 (d, 1H), 7.30 (d, 1H), 4.46 (s, 3H), 4.30 (t, 2H), 4.20 (m, 2H), 31.2 (m, 2H), 2.21 (s, 3H), 1.90 (m, 3H), 1.76 (m, 2H), 1.30 (m, 2H). MS m/z 522 (M+H).

EXAMPLE 9a (S)-1-methyl-6-(4-(2-(1-(5-methylpyridin-2-yl)pyrrolidin-3-yl)ethoxy)-3-(trifluoromethyl)phenyl)-1H-[1,2,3]triazolo[4,5-c]pyridine-4-carbonitrile hydrochloride

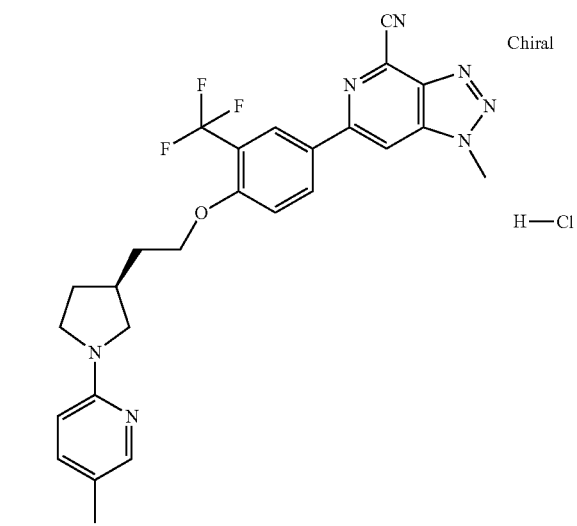

A: (S)-2-(1-(5-methylpyridin-2-yl)pyrrolidin-3-yl)ethanol (S)-2-(Pyrrolidin-3-yl)ethanol (4.12 mmol, 474 mg) 2-fluoro-5-methylpyridine (20.58 mmol, 2287 mg) and triethylamine (20.58 mmol, 2.87 ml, 2082 mg) were combined in acetonitrile (2 ml) and heated to 150° C. in a microwave for 2 hours. Solvent was evaporated under reduced pressure and the remaining residue purified by flash chromatography (50 g silica column, DCM to 3% MeOH in DCM gradient) to afford (S)-2-(1-(5-methylpyridin-2-yl)pyrrolidin-3-yl)ethanol (41.7% yield) as a clear oil. $^1$H NMR (CDCl3) δ: 7.97 (s, 1H), 7.26 (d, 1H), 6.27 (d, 1H), 3.75 (m, 2H), 3.68 (t, 1H), 3.56 (m, 1H), 3.38 (m, 1H), 3.05 (t, 1H), 2.42 (m, 1H), 2.18 (m, 1H), 2.17 (s, 3H), 1.74 (m, 2H), 1.70 (m, 1H).

B: (S)-1-methyl-6-(4-(2-(1-(5-methylpyridin-2-yl)pyrrolidin-3-yl)ethoxy)-3-(trifluoromethyl)phenyl)-1H-[1,2,3]triazolo[4,5-c]pyridine-4-carbonitrile hydrochloride 6-(4-hydroxy-3-(trifluoromethyl)phenyl)-1-methyl-1H-[1,2,3]triazolo[4,5-c]pyridine-4-carbonitrile (0.157 mmol, 50 mg) (S)-2-(1-(5-methylpyridin-2-yl)pyrrolidin-3-yl)ethanol (0.188 mmol, 38.8 mg) and triphenylphosphine (0.188 mmol, 49.3 mg) were suspended in DCM (1000 µl) and DIAD (0.188 mmol, 37.0 µl, 38.0 mg) added. The mixture was stirred at room temperature for 16 hours then a further 0.5 eq of all non-limiting reagents added. Stirring was continued for 4 hours then the mixture purified by SCX and solvent removed under reduced pressure. The solid was suspended in MeOH, filtered, and washed with ether to afford clean product as the free base. The solid was dissolved in a minimum volume of DCM and HCl in ether added. Solvent was removed in a genevac and the resulting solid dried to afford (S)-1-methyl-6-(4-(2-(1-(5-methylpyridin-2-yl)pyrrolidin-3-yl)ethoxy)-3-(trifluoromethyl)phenyl)-1H-[1,2,3]triazolo[4,5-c]pyridine-4-carbonitrile hydrochloride (42.7% yield). $^1$H NMR (DMSO) δ: 8.99 (s, 1H), 8.53 (d, 1H), 8.47 (s, 1H), 7.90 (d, 1H), 7.79 (s, 1H), 7.53 (d, 1H), 6.99 (d, 1H), 4.46 (s, 3H), 4.32 (t, 2H), 3.75 (m, 1H), 3.65 (m, 1H), 3.48 (m, 1H), 3.25 (m, 1H), 2.53 (m, 1H), 2.32 (m, 1H), 2.21 (s, 3H), 2.00 (m, 2H), 1.80 (m, 1H). MS m/z 508 (M+H).

The above procedure for 9a was applied to synthesise the following compounds:

9b: (R)-1-methyl-6-(4-(2-(1-(5-methylpyridin-2-yl)pyrrolidin-3-yl)ethoxy)-3-(trifluoromethyl)phenyl)-1H-[1,2,3]triazolo[4,5-c]pyridine-4-carbonitrile hydrochloride

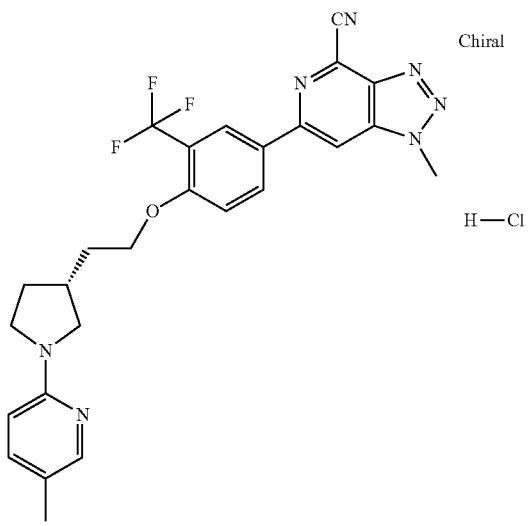

A: (R)-2-(1-(5-methylpyridin-2-yl)pyrrolidin-3-yl)ethanol $^1$H NMR (CDCl3) δ: 7.97 (s, 1H), 7.26 (d, 1H), 6.27 (d, 1H), 3.75 (m, 2H), 3.68 (t, 1H), 3.56 (m, 1H), 3.38 (m, 1H), 3.05 (t, 1H), 2.42 (m, 1H), 2.18 (m, 1H), 2.17 (s, 3H), 1.74 (m, 2H), 1.70 (m, 1H).

B: (R)-1-methyl-6-[4-(2-(1-(5-methylpyridin-2-yl)pyrrolidin-3-yl)ethoxy)-3-(trifluoromethyl)phenyl)-1H-1,2,3]triazolo[4,5-c]pyridine-4-carbonitrile hydrochloride $^1$H NMR (DMSO) δ: 9.00 (s, 1H), 8.54 (d, 1H), 8.47 (s, 1H), 7.87 (d, 1H), 7.80 (s, 1H), 7.52 (d, 1H), 7.01 (d, 1H), 4.47 (s, 3H), 4.33 (t, 2H), 3.80 (m, 1H), 3.70 (m, 1H), 3.48 (m, 1H), 3.27 (m, 1H), 2.55 (m, 1H), 2.25 (m, 1H), 2.21 (s, 3H), 2.00 (m, 2H), 1.80 (m, 1H). MS m/z 508 (M+H).

EXAMPLE 10

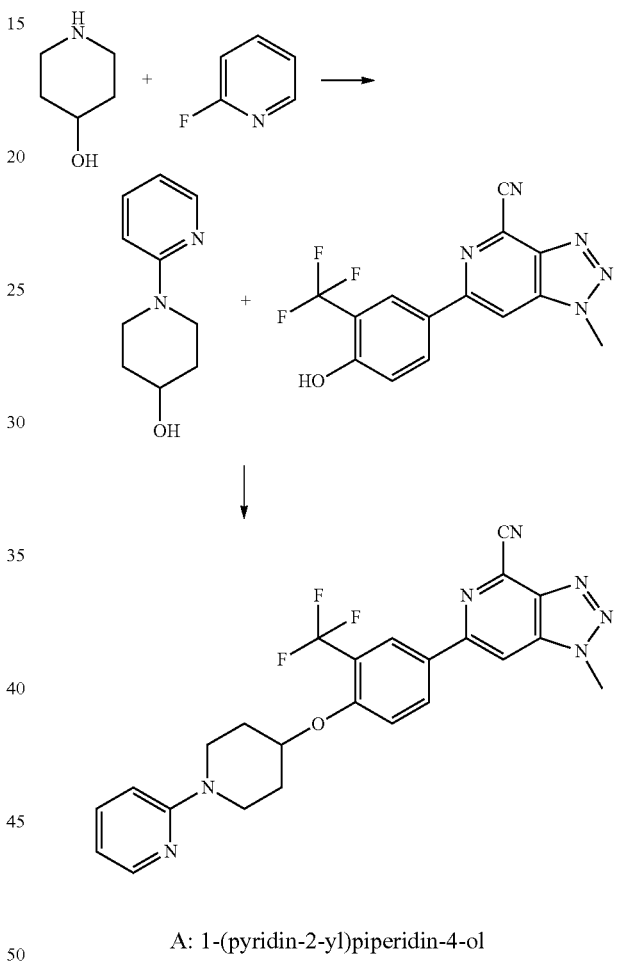

A: 1-(pyridin-2-yl)piperidin-4-ol 1-(pyridin-2-yl)piperidin-4-ol (64.7% yield), 2-fluoropyridine (29.7 mmol, 2.88 g) and triethylamine (49.4 mmol, 6.89 ml, 5.00 g) were dissolved in MeOH (2.5 ml) and heated to 150° C. for 1 hour in the microwave. The solvent was removed at reduced pressure. The resulting residue was purified by column chromatography, eluting with DCM—3% MeOH/DCM to afford 1-(pyridin-2-yl)piperidin-4-ol. (1.14 g) $^1$H NMR (CDCl3) δ: 8.18 (d, 1H), 7.45 (m, 1H), 6.67 (d, 1H), 6.58 (m, 1H), 4.06 (m, 2H), 3.92 (br, 1H), 3.15 (m, 2H), 1.98 (m, 2H), 1.59 (m, 2H).

B: 1-methyl-6-(4-(1-(pyridin-2-yl)piperidin-4-yloxy)-3-(trifluoromethyl)phenyl)-1H-[1,2,3]triazolo[4,5-c]pyridine-4-carbonitrile 6-(4-hydroxy-3-(trifluoromethyl)phenyl)-1-methyl-1H-[1,2,3]triazolo[4,5-c]pyridine-4-carbonitrile (0.940 mmol, 300 mg), 1-(pyridin-2-yl)piperidin-4-ol (1.410 mmol, 251 mg) and Triphenylphosphine (1.410 mmol, 370 mg) were suspended in NMP (1 ml) and DIAD (1.410 mmol, 0.278 ml, 285 mg) added. The mixture was stirred at room temperature overnight. The reaction mixture was passed down an SCX column to afford 1-methyl-6-(4-(1-(pyridin-2-yl)piperidin-4-yloxy)-3-(trifluoro-methyl)phenyl)-1H-[1,2,3]triazolo[4,5-c]pyridine-4-carbonitrile. (0.024 g)

$^1$H NMR (d6-DMSO) δ: 8.95 (s, 1H), 8.47 (m, 2H), 8.13 (s, 1H), 7.60 (d, 1H), 7.52 (t, 1H), 6.88 (d, 1H), 6.64 (br, 1H), 5.03 (br, 1H), 3.78 (br, 2H), 3.58 (br, 2H), 2.03 (m, 2H), 1.75 (br, 2H).

EXAMPLE 11

(S)-1-methyl-6-(4-((1-(pyridin-2-yl)pyrrolidin-3-yl)methoxy)-3-(trifluoromethyl)phenyl)-1H-[1,2,3]triazolo[4,5-c]pyridine-4-carbonitrile

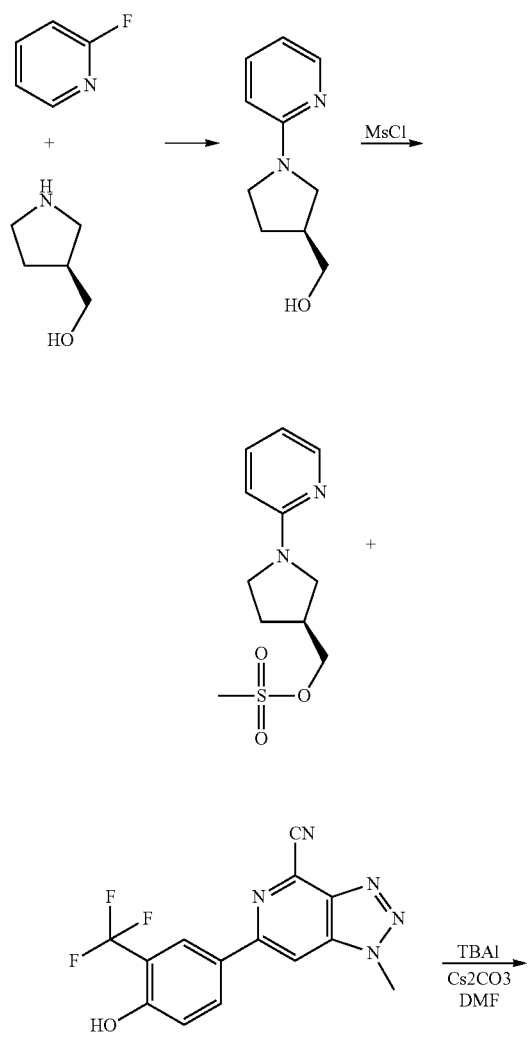

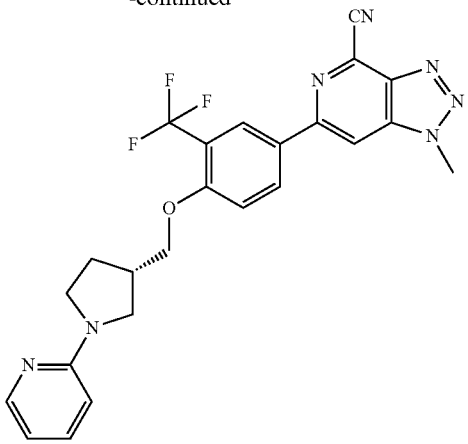

A: (S)-(1-(pyridin-2-yl)pyrrolidin-3-yl)methanol (S)-Pyrrolidin-3-ylmethanol (9.89 mmol, 1 g), 2-fluoropyridine (29.7 mmol, 2.88 g) and triethylamine (49.4 mmol, 6.89 ml, 5.00 g) were dissolved in MeOH (2.5 ml) and heated to 150° C. for 1 hour in the microwave. The resulting residue was purified by silica chromatography, eluting with DCM—5% MeOH/DCM to afford (S)-(1-(pyridin-2-yl)pyrrolidin-3-yl)methanol (1.03 g).

$^1$H NMR (CDCl$_3$) δ: 8.15 (d, 1H), 7.43 (m, 1H), 6.52 (t, 1H), 6.36 (d, 1H), 3.65 (br, 2H), 3.60 (m, 2H), 3.55 (m, 1H), 3.27 (m, 1H), 2.57 (m, 1H), 2.15 (m, 1H), 1.85 (m, 1H).

B: (S)-(1-(pyridin-2-yl)pyrrolidin-3-yl)methyl methanesulfonate (S)-(1-(Pyridin-2-yl)pyrrolidin-3-yl)methanol (1.683 mmol, 0.3 g) and triethylamine (5.05 mmol, 0.702 ml, 0.511 g) were stirred in DCM (10 ml) at 0° C. Methanesulfonyl chloride (2.52 mmol, 0.195 ml, 0.289 g) was added and the reaction allowed to warm to room temperature over 1 hour. The reaction mixture was washed with water, dried over Na$_2$SO$_4$ and concentrated at reduced pressure to afford (S)-(1-(pyridin-2-yl)pyrrolidin-3-yl)methyl methanesulfonate. (0.38 g)

$^1$H NMR (CDCl3) δ: 8.16 (d, 1H), 7.45 (m, 1H), 6.56 (t, 1H), 6.36 (d, 1H), 4.22 (m, 2H), 3.70 (m, 1H), 3.59 (m, 1H), 3.48 (m, 1H), 3.33 (m, 1H), 2.79 (m, 1H), 2.23 (m, 1H), 1.90 (m1H). MS m/z 279.0 (M+H).

C: (S)-1-methyl-6-(4-((1-(pyridin-2-yl)pyrrolidin-3-yl)methoxy)-3-(trifluoromethyl)-phenyl)-1H-[1,2,3]triazolo[4,5-c]pyridine-4-carbonitrile 6-(4-Hydroxy-3-(trifluoromethyl)phenyl)-1-methyl-1H-[1,2,3]triazolo[4,5-c]pyridine-4-carbonitrile (0.313 mmol, 0.1 g), (S)-(1-(pyridin-2-yl)pyrrolidin-3-yl)methyl methanesulfonate (0.376 mmol, 0.096 g), cesium carbonate (0.470 mmol, 0.153 g) and tetrabutylammonium iodide (0.157 mmol, 0.058 g) were stirred in DMF (1 ml) at 50° C. overnight. The reaction mixture was diluted with ethyl acetate, washed with water and dried over Na$_2$SO$_4$. The resulting residue was triturated with ether and filtered. The solid was sonicated in methanol, filtered and dried to afford (S)-1-methyl-6-(4-((1-(pyridin-2-yl)pyrrolidin-3-yl)methoxy)-3-(trifluoromethyl)phenyl)-1H-[1,2,3]triazolo[4,5-c]pyridine-4-carbonitrile. (0.032 g)

¹H NMR (d6-DMSO) δ: 8.99 (s, 1H), 8.48 (m, 2H), 8.06 (d, 1H), 7.51 (m, 2H), 6.54 (t, 1H), 6.44 (d, 1H), 4.46 (s, 3H), 4.29 (d, 2H), 3.63 (m, 1H), 3.54 (m, 1H), 3.42 (m, 1H), 3.31 (m, 1H), 2.85 (m, 1H), 2.19 (m, 1H), 1.93 (m, 1H). MS m/z 480.0 (M+H).

EXAMPLE 12

1-methyl-6-(4-((1-(4-methylpyridin-2-yl)piperidin-4-yl)methoxy)-3-(trifluoromethyl)phenyl)-1H-[1,2,3]triazolo[4,5-c]pyridine-4-carbonitrile

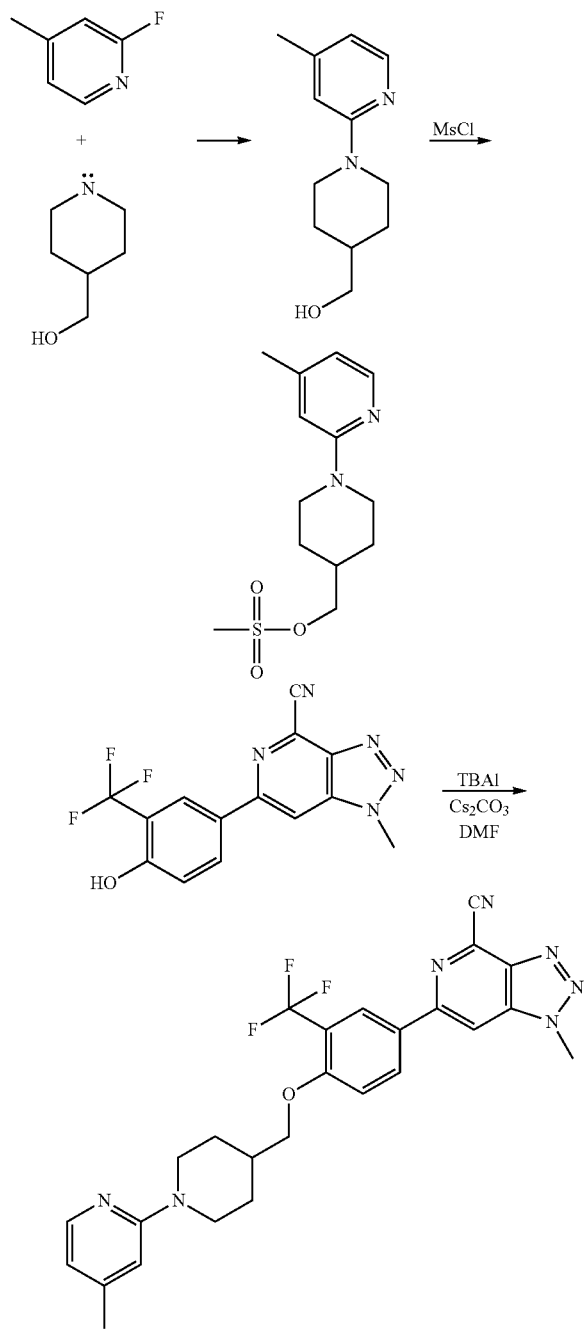

A: (1-(4-methylpyridin-2-yl)piperidin-4-yl)methanol

Piperidin-4-ylmethanol (8.68 mmol, 1 g), 2-fluoro-4-methylpyridine (26.0 mmol, 2.89 g) and triethylamine (26.0 mmol, 3.63 mL, 2.64 g) were combined and heated to 150° C. for 1 hour in the microwave. The solvent was removed at reduced pressure and the residue purified by silica chromatography eluting with DCM—2% MeOH/CM to afford (1-(4-methylpyridin-2-yl)piperidin-4-yl)methanol. (0.75 g) MS m/z 207.2 (M+H).

B: (1-(4-methylpyridin-2-yl)piperidin-4-yl)methyl methanesulfonate (1-(4-Methylpyridin-2-yl)piperidin-4-yl)methanol (0.970 mmol, 0.2 g) and triethylamine (2.91 mmol, 0.404 mL, 0.294 g) were stirred in DCM at 0° C. Methanesulfonyl chloride (1.454 mmol, 0.113 mL, 0.167 g) was added dropwise and the reaction allowed to warm to room temperature and stirred for 1 hour. The reaction mixture was washed with water, dried over Na₂SO₄ and concentrated in vacuo to afford (1-(4-methylpyridin-2-yl)piperidin-4-yl)methyl methanesulfonate. (0.234 g)

¹H NMR (CDCl3) δ: 8.04 (d, 1H), 6.48 (s, 1H), 6.45 (d, 1H), 4.32 (d, 2H), 4.10 (d, 2H), 3.06 (br, 1H), 3.01 (s, 3H), 2.53 (m, 2H), 2.26 (s, 3H), 2.02 (br, 1H), 1.85 (d, 2H). MS m/z 285.0 (M+H).

C: 1-methyl-6-(4-((1-(4-methylpyridin-2-yl)piperidin-4-yl)methoxy)-3-(trifluoromethyl)phenyl)-1H-[1,2,3]triazolo[4,5-c]pyridine-4-carbonitrile 6-(4-Hydroxy-3-(trifluoromethyl)phenyl)-1-methyl-1H-[1,2,3]triazolo[4,5-c]pyridine-4-carbonitrile (0.626 mmol, 0.2 g), (1-(4-methylpyridin-2-yl)piperidin-4-yl)methyl methanesulfonate (0.752 mmol, 0.214 g), cesium carbonate (0.940 mmol, 0.306 g) and tetrabutylammonium iodide (0.313 mmol, 0.116 g) were stirred in DMF (1 ml) at 50° C. overnight. The reaction mixture was diluted with ethyl acetate, washed with water and dried over Na₂SO₄. The resulting residue was triturated with ether and filtered. The solid was sonicated in methanol, filtered and dried to afford 1-methyl-6-(4-((1-(4-methylpyridin-2-yl)piperidin-4-yl)methoxy)-3-(trifluoromethyl)phenyl)-1H-[1,2,3]triazolo[4,5-c]pyridine-4-carbonitrile. (134 mg)

¹H NMR (d6-DMSO) δ: 8.99 (d, 1H), 8.46 (m, 2H), 7.92 (dd, 1H), 7.50 (dd, 2H), 6.66 (s, 0.5H), 6.40 (dd, 1H), 6.24 (s, 0.5H), 4.46 (s, 3H), 4.32 (m, 2H), 4.11 (d, 1H), 3.65 (m, 0.5H), 3.52 (m, 0.5H), 3.06 (m, 0.5H), 2.82 (m, 1H), 2.16 (m, 4H), 1.96 (m, 1H), 1.86 (m, 1H), 1.72 (m, 1H), 1.36 (m, 1H). MS m/z 508.2 (M+H).

EXAMPLE 13

(R)-1-methyl-6-(4-((1-(pyridin-2-yl)pyrrolidin-3-yl)methoxy)-3-(trifluoromethyl)phenyl)-1H-[1,2,3]triazolo[4,5-c]pyridine-4-carbonitrile

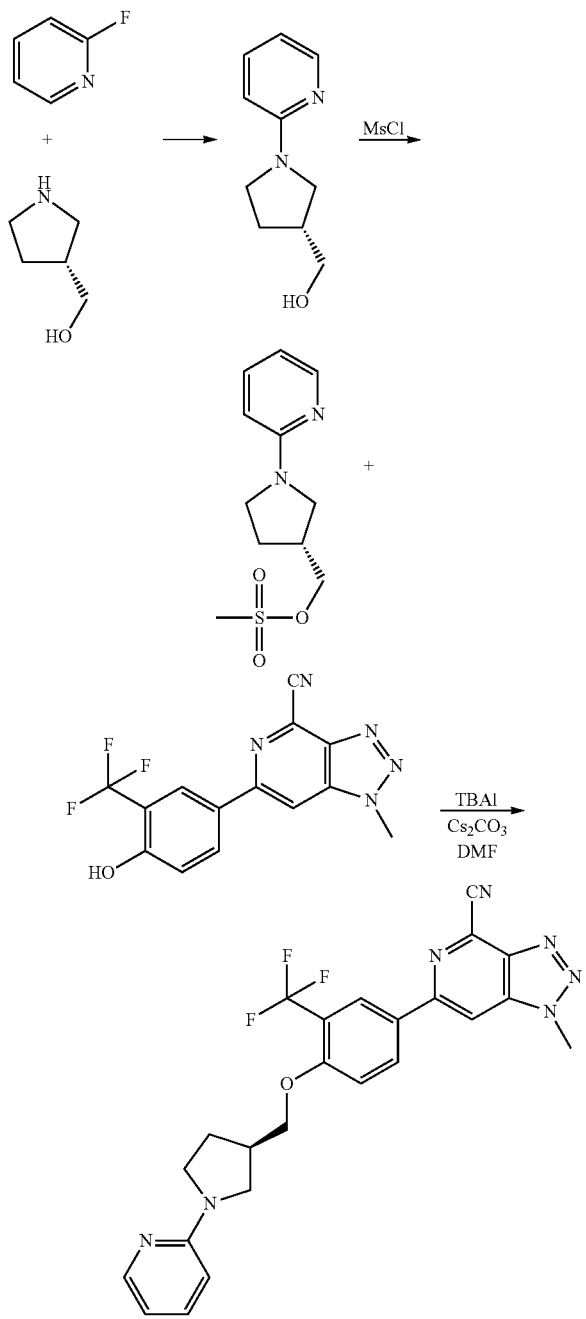

A: (R)-1-(pyridin-2-yl)pyrrolidin-3-yl)methanol (R)-(1-(Pyridin-2-yl)pyrrolidin-3-yl)methanol (1.683 mmol, 0.3 g) and triethylamine (5.05 mmol, 0.702 ml, 0.511 g) were stirred in DCM (10 ml) at 0° C. methanesulfonyl chloride (2.52 mmol, 0.195 ml, 0.289 g) was added and the reaction allowed to warm to room temperature over 1 hour. The reaction mixture was washed with water, dried over Na2SO4 and concentrated at reduced pressure to afford (R)-(1-(pyridin-2-yl)pyrrolidin-3-yl)methanol. (0.408 g)

$^1$H NMR (CDCl3) δ: 8.16 (d, 1H), 7.43 (m, 1H), 6.52 (t, 1H), 6.36 (d, 1H), 3.65 (br, 2H), 3.60 (m, 2H), 3.55 (m, 1H), 3.27 (m, 1H), 2.57 (m, 1H), 2.15 (m, 1H), 1.85 (m, 1H).

B: (R)-(1-(pyridin-2-yl)pyrrolidin-3-yl)methyl methanesulfonate (R)-Pyrrolidin-3-ylmethanol (9.89 mmol, 1 g), 2-fluoropyridine (29.7 mmol, 2.88 g) and triethylamine (49.4 mmol, 6.89 ml, 5.00 g) were dissolved in MeOH (2.5 ml) and heated to 150° C. for 1 hour in the microwave. The resulting residue was purified by silica chromatography, eluting with DCM—5% MeOH/DCM to afford (R)-(1-(pyridin-2-yl)pyrrolidin-3-yl)methyl methanesulfonate. (0.79 g)

$^1$H NMR (CDCl3) δ: 8.04 (d, 1H), 6.48 (s, 1H), 6.45 (d, 1H), 4.32 (d, 2H), 4.10 (d, 2H), 3.06 (br, 1H), 3.01 (s, 3H), 2.53 (m, 2H), 2.26 (s, 3H), 2.02 (br, 1H), 1.85 (d, 2H). MS m/z 257.0 (M+H).

C: (R)-1-methyl-6-(4-((1-(pyridin-2-yl)pyrrolidin-3-yl)methoxy)-3-(trifluoromethyl)phenyl)-1H-[1,2,3]triazolo[4,5-c]pyridine-4-carbonitrile 6-(4-Hydroxy-3-(trifluoromethyl)phenyl)-1-methyl-1H-[1,2,3]triazolo[4,5-c]pyridine-4-carbonitrile (0.235 mmol, 0.075 g), (R)-(1-(pyridin-2-yl)pyrrolidin-3-yl)methyl methanesulfonate (0.282 mmol, 0.072 g), cesium carbonate (0.352 mmol, 0.115 g) and tetrabutylammonium iodide (0.117 mmol, 0.043 g) were stirred in DMF (1 ml) at 50° C. overnight. The reaction mixture was diluted with ethyl acetate, washed with water and dried over Na$_2$SO$_4$. The resulting residue was triturated with ether and filtered. The solid was sonicated in methanol, filtered and dried to afford (R)-1-methyl-6-(4-((1-(pyridin-2-yl)pyrrolidin-3-yl)methoxy)-3-(trifluoromethyl)phenyl)-1H-[1,2,3]triazolo[4,5-c]pyridine-4-carbonitrile. (47 mg)

$^1$H NMR (d6-DMSO) δ: 8.99 (s, 1H), 8.48 (m, 2H), 8.06 (d, 1H), 7.51 (m, 2H), 6.54 (t, 1H), 6.44 (d, 1H), 4.46 (s, 3H), 4.29 (d, 2H), 3.63 (m, 1H), 3.54 (m, 1H), 3.42 (m, 1H), 3.31 (m, 1H), 2.85 (m, 1H), 2.19 (m, 1H), 1.93 (m, 1H). MS m/z 480.0 (M+H).

EXAMPLE 14

1-methyl-6-(4-(2-(1-(pyridin-2-yl)azetidin-3-yl)ethoxy)-3-(trifluoromethyl)phenyl)-1H-[1,2,3]triazolo[4,5-d]pyridine-4-carbonitrile hydrochloride

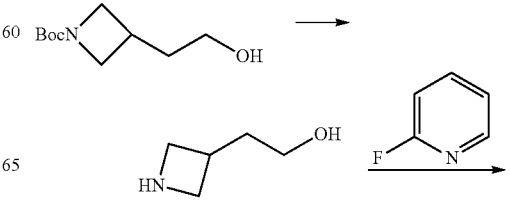

-continued

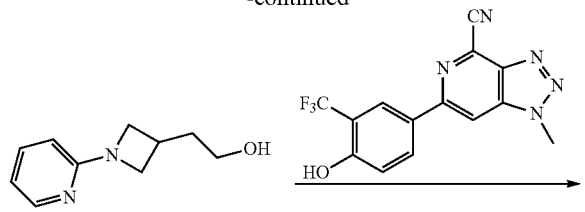

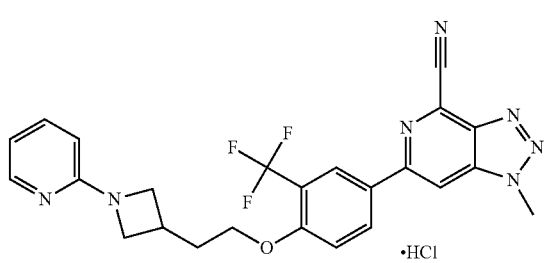

A: 2-(azetidin-3-yl)ethanol

Tert-butyl 3-(2-hydroxyethyl)azetidine-1-carboxylate (13.91 mmol, 2.8 g) was dissolved in DCM (80 ml). Trifluoroacetic acid (278 mmol, 20.67 ml, 31.7 g) was added and the reaction stirred at room temperature for c. 45 minutes. Solvent was removed under reduced pressure and the product purified by SCX to give 2-(azetidin-3-yl)ethanol as a crude oil. $^1$H NMR (CDCl$_3$) δ: 4.52 (t, 1H), 4.29 (t, 1H), 4.10 (m, 1H), 3.83 (m, 1H), 3.68 (m, 2H), 2.89 (m, 1H), 1.87 (m, 2H).

B: 2-(1-(pyridin-2-yl)azetidin-3-yl)ethanol 2-(Azetidin-3-yl)ethanol (4.92 mmol, 0.498 g), 2-fluoropyridine (9.85 mmol, 0.846 ml, 0.956 g), triethylamine (14.77 mmol, 2.053 ml, 1.495 g) and methanol (2.5 ml) were combined and heated to 150° C. in a microwave for 40 minutes. TLC analysis showed some starting material remained and therefore the solution was heated for a further 40 minutes. The resulting solution was dissolved in DCM (c. 20 ml) and washed with water. Solvent was removed under reduced pressure to yield a crude product. This was then purified by flash chromatography (10 g silica column, DCM to 3% MeOH in DCM gradient). Appropriate fractions were combined and solvent removed under reduced pressure to give final product. $^1$H NMR (CDCl$_3$) δ: 8.17 (d, 1H), 7.42 (t, 1H), 6.57 (t, 1H), 6.26 (d, 1H), 4.16 (t, 2H), 3.70 (m, 4H), 2.88 (m, 1H), 1.95 (q, 2H).

C: 1-methyl-6-(4-(2-(1-(pyridin-2-yl)azetidin-3-yl)ethoxy)-3-(trifluoromethyl)phenyl)-1H-[1,2,3]triazolo[4,5-c]pyridine-4-carbonitrile hydrochloride 6-(4-Hydroxy-3-(trifluoromethyl)phenyl)-1-methyl-1H-[1,2,3]triazolo[4,5-c]pyridine-4-carbonitrile (0.626 mmol, 0.2 g), 2-(1-(pyridin-2-yl)azetidin-3-yl)ethanol (0.940 mmol, 0.167 g) and triphenylphosphine (0.940 mmol, 0.246 g) were dissolved in NMP (c. 6 ml). DIAD (0.940 mmol, 0.185 ml, 0.190 g) was added dropwise and the reaction stirred at room temperature for 6 hours. The resulting solution was then dissolved in ethyl acetate (c. 100 ml) and washed with a 1:1 mix of water and saturated NaHCO$_3$ (3×c. 100 ml). Solution was dried (Na$_2$SO$_4$) and solvent removed under reduced pressure to give crude product as a dark orange oil (1.1687 g). This was then purified by flash chromatography (25 g silica column, DCM to 4% MeOH in DCM gradient) followed by SCX. Solvent was removed under reduced pressure and the resulting solid lyophilised in 0.5 M HCl followed by water in a genevac. The resulting salt was analysed by LCMS, proton and COSY NMR, showing small amounts of impurity remaining. Salt was suspended in MeOH (3 ml) and heated. Solid was removed by filtration to give final product. $^1$H NMR (DMSO) δ: 9.00 (s, 1H), 8.52 (d, 1H), 8.48 (s, 1H), 7.97 (d, 1H), 7.93 (t, 1H), 7.53 (d, 1H), 6.87 (t, 1H), 6.80 (d, 1H), 4.47 (s, 3H), 4.37 (t, 2H), 4.29 (t, 2H), 4.02 (m, 2H), 3.07 (m, 1H), 2.21 (q, 2H). MS m/z 480.20 (M+H).

EXAMPLE 15

1-methyl-6-(4-(2-(1-(6-methylpyridin-2-yl)azetidin-3-yl)ethoxy)-3-(trifluoromethyl)phenyl)-1H-[1,2,3]triazolo[4,5-c]pyridine-4-carbonitrile hydrochloride

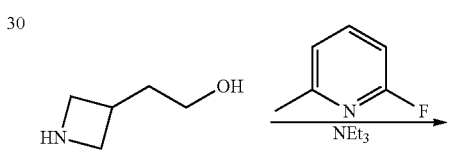

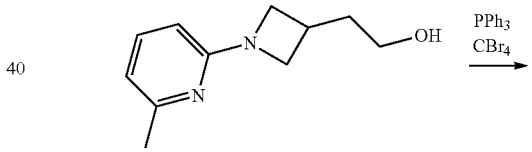

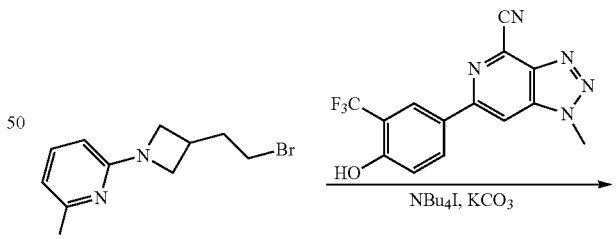

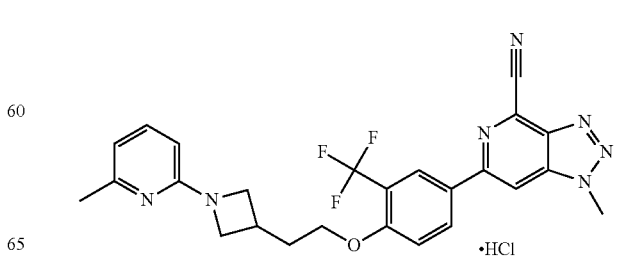

A: 2-(1-(6-methylpyridin-2-yl)azetidin-3-yl)ethanol 2-(Azetidin-3-yl)ethanol (4.91 mmol, 0.497 g), 2-fluoro-6-methylpyridine (9.83 mmol, 1.014 ml, 1.092 g), and triethylamine (14.74 mmol, 2.072 ml, 1.492 g) were dissolved in MeOH (2 ml). The solution was then heated (microwave) to 150° C. for 1 hour. Solvent was removed under reduced pressure. The resulting oil was redissolved in DCM and washed once with water. Solution was dried (Na$_2$SO$_4$), and solvent removed under reduced pressure to give a crude product. This was then purified by flash chromatography (10 g silica column, DCM to 2% MeOH in DCM gradient). Appropriate fractions were combined and solvent removed under reduced pressure to give final product. $^1$H NMR (CDCl$_3$) δ: 7.32 (t, 1H), 6.43 (d, 1H), 6.08 (d, 1H), 4.13 (t, 2H), 3.69 (m, 4H), 2.84 (m, 1H), 2.39 (s, 3H), 1.92 (q, 2H).

B: 2-(3-(2-bromoethyl)azetidin-1-yl)-6-methylpyridine 2-(1-(6-Methylpyridin-2-yl)azetidin-3-yl)ethanol (1.415 mmol, 0.272 g) and carbon tetrabromide (2.83 mmol, 0.938 g) were dissolved in DCM (2 ml). Triphenylphosphine (2.83 mmol, 0.742 g) was added and the reaction stirred for 16 hours. Reaction mixture was purified by flash chromatography (DCM to 4% MeOH in DCM gradient, 25 g silica column). Appropriate fractions were combined and solvent removed under reduced pressure giving a crude product containing some triphenylphosphine related impurities. Used in next step. $^1$H NMR (CDCl$_3$) δ: 7.46 (m, 1H), 6.48 (m, 1H), 4.40 (t, 2H), 3.93 (t, 2H), 3.48 (t, 1H), 3.42 (t, 2H), 2.97 (m, 1H), 2.59 (s, 3H), 2.25 (q, 2H).

C: 1-methyl-6-(4-(2-(1-(6-methylpyridin-2-yl)azetidin-3-yl)ethoxy)-3-(trifluoromethyl)phenyl)-1H-[1,2,3]triazolo[4,5-c]pyridine-4-carbonitrile hydrochloride 2-(3-(2-Bromoethyl)azetidin-1-yl)-6-methylpyridine (0.940 mmol, 240 mg), 6-(4-hydroxy-3-(trifluoromethyl)phenyl)-1-methyl-1H-[1,2,3]triazolo[4,5-c]pyridine-4-carbonitrile (0.626 mmol, 200 mg), potassium carbonate (0.940 mmol, 130 mg) and tetrabutylammonium iodide (0.313 mmol, 116 mg) were dissolved in DMF (6 ml). The reaction was heated to 50° C. and stirred for 16 hours. The reaction mixture was then dissolved in ethyl acetate (c. 100 ml) and washed with a 1:1 mixture of saturated sodium bicarbonate solution in water (3×100 ml). Solution was dried (Na$_2$SO$_4$) and solvent removed under reduced pressure. Product purified by flash chromatography (25 g silica column, ethyl acetate). Appropriate fractions were combined and solvent removed under reduced pressure to give a crude product containing a triphenylphosphine derivative impurity. Solid was then suspended in methanol (c. 10 ml) and heated to 50° C. Solid product was removed by filtration and washed with ether. Solid was then lyophilised (genevac) with HCl (0.5 M) and then water to give the product as a HCl salt. $^1$H NMR (DMSO) δ: 9.00 (s, 1H), 8.51 (d, 1H), 8.48 (s, 1H), 7.84 (t, 1H), 7.53 (d, 1H), 6.71 (d, 1H), 6.62 (d, 1H), 4.47 (s, 3H), 4.40 (t, 2H), 4.29 (t, 2H), 4.04 (t, 2H), 3.04 (m, 1H), 2.47 (s, 3H), 2.22 (q, 2H). MS m/z 494.21 (M+H).

EXAMPLE 16

1-methyl-6-(4-(2-(1-(methylsulfonyl)piperidin-4-yl)ethoxy)-3-(trifluoromethyl)phenyl)-1H-[1,2,3]triazolo[4,5-c]pyridine-4-carbonitrile

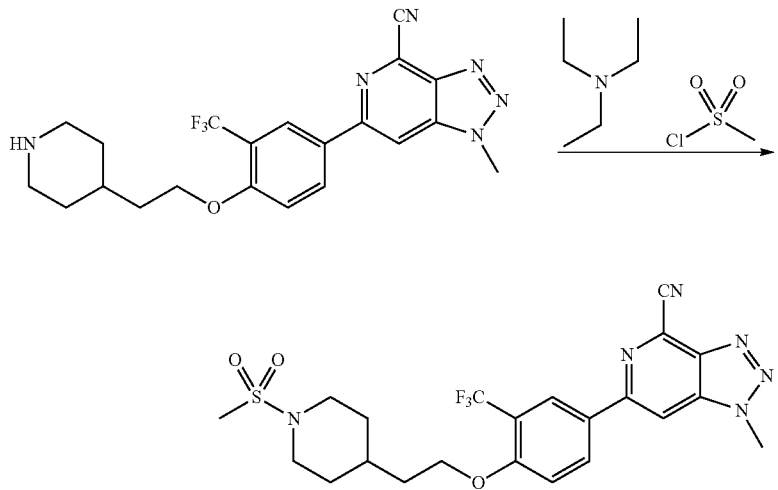

1-Methyl-6-(4-(2-(piperidin-4-yl)ethoxy)-3-(trifluoromethyl)phenyl)-1H-[1,2,3]-triazolo[4,5-c]pyridine-4-carbonitrile (50 mg), triethylamine (0.019 ml), and methanesulfonyl chloride (8.99 μl) were combined in dichloromethane (1 ml) and the reaction mixture stirred at room temperature for 3 hours. Washed with water, the organic layer was separated, dried, and blown down to afford crude product. Solid was suspended in methanol and filtered off to afford the title compound (32.5 mg).

$^1$H NMR (DMSO) δ: 8.98 (s, 1H), 8.50 (d, 1H), 8.45 (s, 1H), 7.52 (d, 1H), 4.46 (s, 3H), 4.29 (t, 2H), 3.55 (d, 2H), 2.85 (s, 3H), 2.67 (t, 2H), 1.82 (m, 4H), 1.62 (m, 1H), 1.27 (q, 2H). MS m/z 509 (M+H).

EXAMPLE 17

6-(4-(2-(1-acetylpiperidin-4-yl)ethoxy)-3-(trifluoromethyl)phenyl)-1-methyl-1H-[1,2,3]triazolo[4,5-c]pyridine-4-carbonitrile

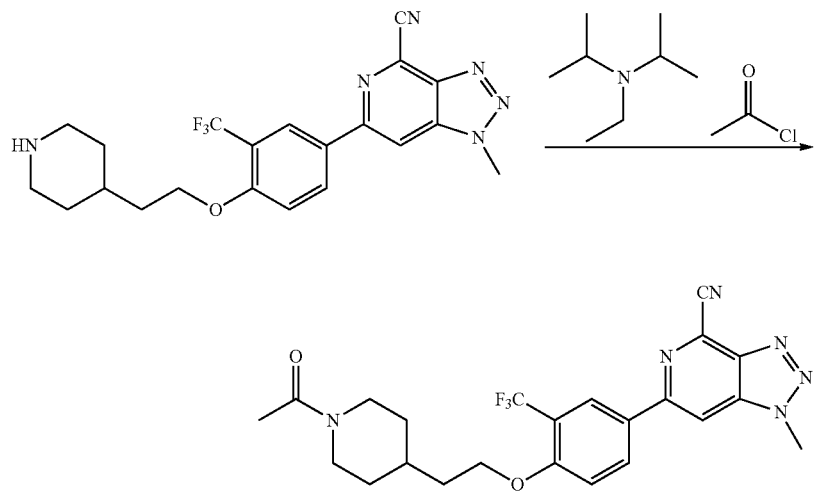

1-Methyl-6-(4-(2-(piperidin-4-yl)ethoxy)-3-(trifluoromethyl)phenyl)-1H-[1,2,3]triazolo[4,5-c]pyridine-4-carbonitrile (50 mg), acetyl chloride (0.041 ml), and N-ethyl-N-isopropylpropan-2-amine (0.096 ml) were combined in dichloromethane (1 ml) and the reaction mixture stirred at room temperature for 2 hours. Washed with water the organic layer was separated, dried, and blown down to afford crude product. Solid was suspended in methanol and filtered off to afford the title compound (29.1 mg).

$^1$H NMR (CDCl3) δ: 8.32 (d, 1H), 8.27 (s, 1H), 7.95 (s, 1H), 7.14 (d, 1H), 4.62 (d, 1H), 4.43 (s, 3H), 4.21 (t, 2H), 3.82 (d, 1H), 3.07 (t, 1H), 2.57 (t, 1H), 2.09 (s, 3H), 1.85 (m, 5H), 1.24 (m, 2H). MS m/z 473 (M+H).

EXAMPLE 18

4-(2-(4-(4-cyano-1-methyl-1H-[1,2,3]triazolo[4,5-d]pyridin-6-yl)-2-(trifluoromethyl)phenoxy)ethyl)-N-methylpiperidine-1-carboxamide

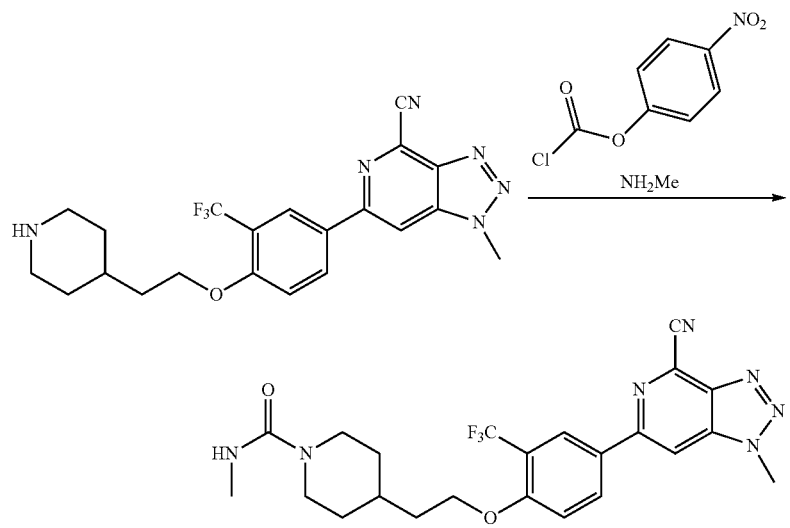

1-Methyl-6-(4-(2-(piperidin-4-yl)ethoxy)-3-(trifluoromethyl)phenyl)-1H-[1,2,3]triazolo[4,5-c]pyridine-4-carbonitrile (50 mg) and 4-nitrophenyl carbono-chloridate (23 mg) were combined in dichloromethane and the reaction mixture stirred at room temperature for an hour. Methylamine (0.290 ml) was added and the reaction mixture stirred for 3 hours. Washed with water, the organic layer was separated, dried, and blown down to afford crude product. Purified by acidic prep HPLC to afford the title compound (8.1 mg).

$^1$H NMR (CDCl3) δ: 8.31 (d, 1H), 8.26 (s, 1H), 7.95 (s, 1H), 7.13 (d, 1H), 4.43 (s, 3H), 4.40 (m, 1H), 4.20 (t, 2H), 3.93 (d, 2H), 2.81 (m, 5H), 1.80 (m, 5H), 1.26 (m, 2H). MS m/z 488.2 (M+H).

EXAMPLE 19

1-methyl-6-(4-(2-(1-(2-(methylsulfonyl)ethyl)piperidin-4-yl)ethoxy)-3-(trifluoromethyl)phenyl)-1H-[1,2,3]triazolo[4,5-d]pyridine-4-carbonitrile

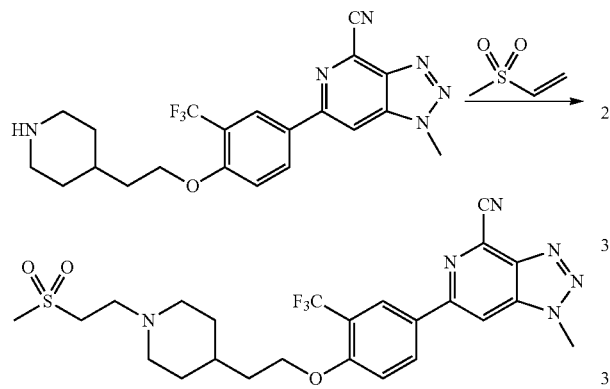

1-Methyl-6-(4-(2-(piperidin-4-yl)ethoxy)-3-(trifluoromethyl)phenyl)-1H-[1,2,3]-triazolo[4,5-c]pyridine-4-carbonitrile (50 mg) and methylsulfonylethene (0.051 ml) were combined in acetonitrile (3 ml) and the reaction mixture microwaved at 120° C. for 20 minutes. The reaction mixture was concentrated under vacuum and the resulting solid suspended in methanol and filtered off to afford the title compound (43.8 mg).

$^1$H NMR (DMSO) δ: 8.97 (s, 1H), 8.47 (d, 1H), 8.44 (s, 1H), 7.50 (d, 1H), 4.46 (s, 3H), 4.26 (t, 2H), 3.27 (t, 2H), 3.02 (s, 3H), 2.88 (d, 2H), 2.67 (t, 2H), 1.91 (t, 2H), 1.71 (m, 4H), 1.51 (m, 1H), 1.20 (qd, 2H). MS m/z 537 (M+H).

EXAMPLE 20

1-methyl-6-(4-(pyridin-2-ylmethoxy)-3-(trifluoromethyl)phenyl)-1H-[1,2,3]triazolo[4,5-c]pyridine-4-carbonitrile

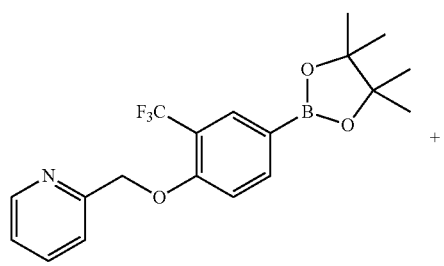
+

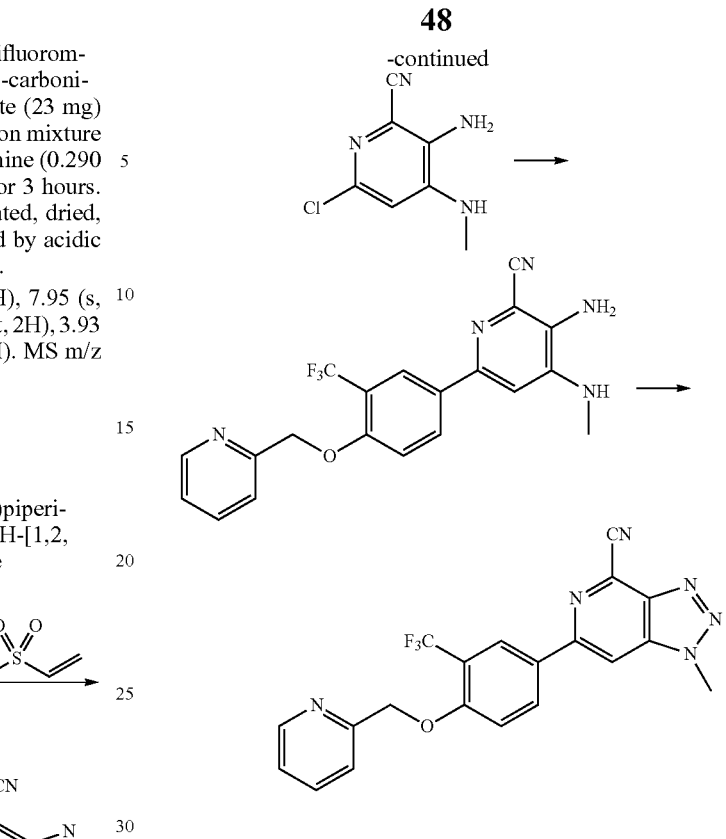

A: 3-amino-4-(methylamino)-6-(4-(pyridin-2-ylmethoxy)-3-(trifluoromethyl)phenyl)picolinonitrile The mixture of 2-((4-(4,4,5,5-tetramethyl-1,3,2-dioxaborolan-2-yl)-2-(trifluoromethyl)phenoxy)methyl)pyridine (1.35 g), 3-amino-6-chloro-4-(methylamino)-picolinonitrile (0.5 g), tris(dibenzylideneacetone)dipalladium (125 mg), tricyclohexylphosphine (92 mg) in a mixed solvent of dioxane (15 ml) and water (10 ml) was heated under nitrogen at 100° C. for 3 hours. After cooling to room temperature, the mixture extracted with ethyl acetate (200 ml), organic layer dried over sodium sulphate, solvent removed under reduced pressure, residue was used for next step without further purification. MS m/z 400 (M+H).

B: 1-methyl-6-(4-(pyridin-2-ylmethoxy)-3-(trifluoromethyl)phenyl)-1H-[1,2,3]triazolo[4,5-c]pyridine-4-carbonitrile To 3-amino-4-(methylamino)-6-(4-(pyridin-2-ylmethoxy)-3-(trifluoromethyl)-phenyl)picolinonitrile (1.7 g) in NMP (20 ml) was added 1M hydrochloric acid (22 ml) and cooled to 5-10° C. with an ice bath. To above solution was then added dropwise a solution of sodium nitrite (0.59 g) in water (5 ml) during 5 minutes. The mixture was stirred at room temperature for another 1 hour. After adding ethyl acetate (200 ml), the mixture washed with water (4×100 ml), brine (50 ml), solvent removed under reduced pressure. Upon addition of methanol (20 ml) to the residue, the desired product precipitated and collected by filtration to give 1-methyl-6-(4-(pyridin-2-yl-methoxy)-3-(trifluoromethyl)phenyl)-1H-[1,2,3]triazolo[4,5-c]pyridine-4-carbonitrile (480 mg) as a white solid. $^1$H NMR (CDCl3) δ: 8.61 (d, 1H), 8.35 (s, 1H), 8.29 (d, 1H), 7.98 (s, 1H), 7.78 (t, 1H), 7.60 (d, 1H), 7.27 (t, 1H), 7.22 (d, 1H), 5.40 (s, 2H), 4.44 (s, 3H). MS m/z 411 (M+H).

EXAMPLE 21

1-methyl-6-(4-(1-N-oxy-pyridin-2-ylmethoxy)-3-(trifluoromethyl)phenyl)-1H-[1,2,3]triazolo[4,5-c]pyridine-4-carbonitrile

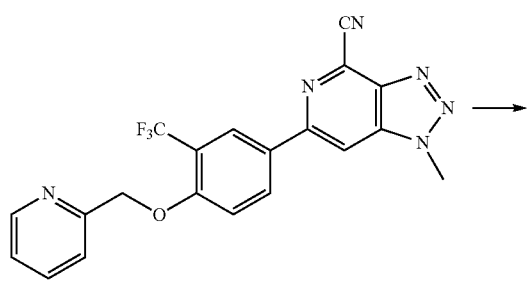

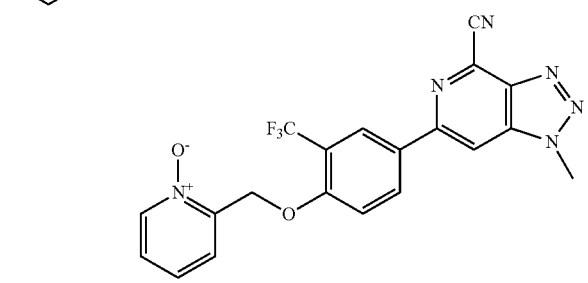

1-Methyl-6-(4-(pyridin-2-ylmethoxy)-3-(trifluoromethyl)phenyl)-1H-[1,2,3]triazolo[4,5-c]pyridine-4-carbonitrile (185 mg) and MCPBA (233 mg) in DCM (10 ml) was stirred at room temperature for 2 hours. After diluting with ethyl acetate (150 ml), washed with sodium carbonate (5%, 4×100 ml), dried over sodium sulphate, solvent removed under reduced pressure, residue was washed with methanol to give 1-methyl-6-(4-(1-N-oxy-pyridin-2-ylmethoxy)-3-(trifluoromethyl)phenyl)-1H-[1,2,3]-triazolo[4,5-c]pyridine-4-carbonitrile (128 mg) as a white solid.

¹H NMR (CDCl3) δ: 8.42 (s, 1H), 8.3-8.4 (m, 2H), 8.01 (s, 1H), 7.78 (d, 1H), 7.43 (t, 1H), 7.36 (d, 1H), 7.32 (t, 1H), 5.50 (s, 2H), 4.46 (s, 3H). MS m/z 427 (M+H).

EXAMPLE 22

1-methyl-6-(4-(pyridin-3-ylmethoxy)-3-(trifluoromethyl)phenyl)-1H-[1,2,3]triazolo[4,5-c]pyridine-4-carbonitrile

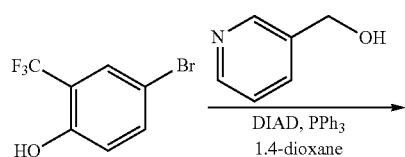

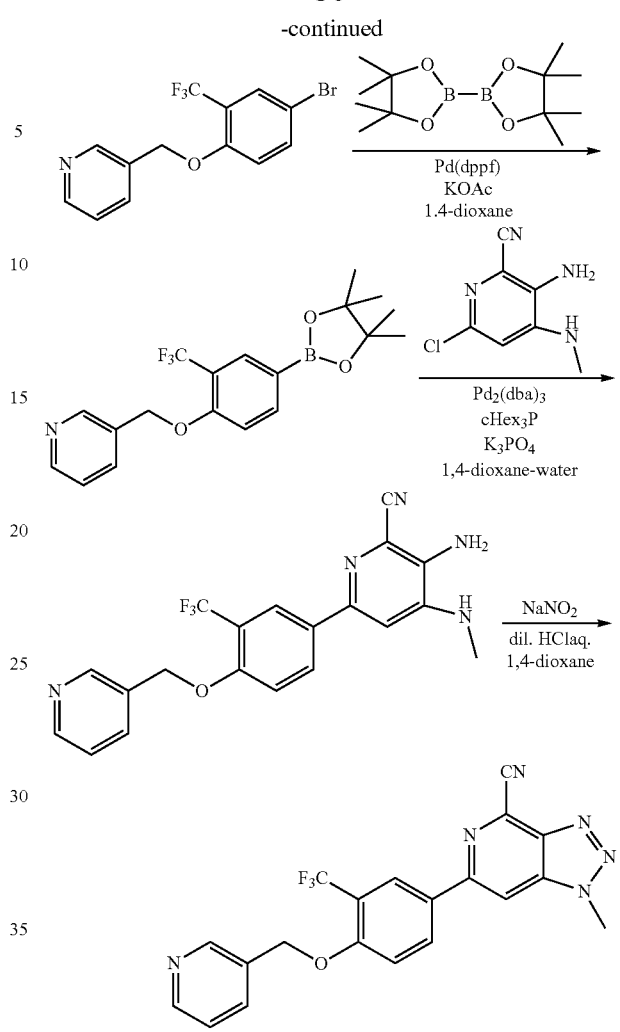

A: 3-((4-Bromo-2-(trifluoromethyl)phenoxy)methyl)pyridine

To a suspension of 4-bromo-2-(trifluoromethyl)phenol (8.00 g) in 1,4-dioxane (100 ml), triphenylphosphine (10.99 g) and 3-pyridylcarbinol (3.88 g) were added. Then diisopropyl azodicarboxylate (8.93 g) was dropwised and stirred at 20° C. for 18 h. The mixture was evaporated off the solvent, diethyl ether (100 ml) and iso-hexane (25 ml) were added and stirred at 20° C. for 2 h, stood for 3 days, filtered and washed with diethyl ether and iso-hexane. The filtrate was concentrated and purified by Biotage SNAP cartridge KP-Sil column (100 g, heptane:ethyl acetate=1:0, 2:1 to 1:1) to give 15.2 g light yellow solid as 3-((4-bromo-2-(trifluoromethyl)phenoxy)-methyl)pyridine (70% purity).

¹H NMR (CDCl₃) δ: 8.67 (d, 1H, J=1.3 Hz), 8.60 (d, 1H, J=3.6 Hz), 7.79 (d, 1H, J=7.8 Hz), 7.72 (d, 1H, J=2.4 Hz), 7.60 (dd, 1H, J=8.8, 2.4 Hz), 7.34 (dd, 1H, J=7.8, 4.8 Hz), 6.94 (d, 1H, J=8.8 Hz), 5.18 (s, 2H).

B: 3-((4-(4,4,5,5-Tetramethyl-1,3,2-dioxaborolan-2-yl)-2-(trifluoromethyl)phenoxy)methyl)pyridine A suspension of 3-((4-bromo-2-(trifluoromethyl)phenoxy)methyl)pyridine (15.20 g), bis(pinacolato)diboron (10.38 g), 1,1'-bis(diphenylphosphino)ferrocenedichloropalladium(II) (1.17 g) and potassium acetate (9.53 g) in dry 1,4-dioxane (60 ml) was stirred at 100° C. for 2.5 h. The solvent was evaporated and partitioned between water and dichloromethane then separated. The aqueous layer was extracted further with dichloromethane, combined organic layer was dried over sodium sulfate, filtered and concentrated. Purified by Biotage SNAP cartridge KP-Sil column (100 g, heptane:ethyl acetate=1:0, 3:1 to 2:1) to give 15.234 g orange oil. Dissolved in diethyl ether (25 ml), 2N hydrochloric acid in diethyl ether (20 ml) was added, filtered to collect the precipitate and washed with ethyl acetate to give colourless solid. This solid was partitioned between ethyl acetate and water, neutralised with saturated sodium bicarbonate solution then separated. The aqueous layer was extracted further with ethyl acetate, combined organic layer was dried over sodium sulfate, filtered and concentrated to give 9.64 g orange oil as 3-((4-(4,4,5,5-tetramethyl-1,3,2-dioxaborolan-2-yl)-2-(trifluoromethyl)phenoxy)methyl)pyridine (79%).

$^1$H NMR (CDCl$_3$) δ: 8.68 (s, 1H), 8.59 (d, 1H, J=3.2 Hz), 8.05 (s, 1H), 7.93 (dd, 1H, J=8.3, 1.2 Hz), 7.81 (d, 1H, J=7.9 Hz), 7.34 (dd, 1H, J=7.5, 5.0 Hz), 7.04 (d, 1H, J=8.3 Hz), 5.23 (s, 2H), 1.34 (s, 12H).

C: 3-Amino-4-(methylamino)-6-(4-(pyridin-3-yl-methoxy)-3-(trifluoromethyl)-phenyl)picolinonitrile A suspension of 3-((4-(4,4,5,5-tetramethyl-1,3,2-dioxaborolan-2-yl)-2-(trifluoromethyl)phenoxy)methyl)pyridine (2.38 g), 3-amino-6-chloro-4-(methylamino)-picolinonitrile (1.15 g), tris(dibenzylideneacetone)dipalladium (0) (296 mg), tricyclohexylphosphine (218 mg) and potassium phosphate (2.78 g) in 1,4-dioxane (20 ml) and water (10 ml) was stirred at 100° C. for 2 h. The reaction mixture was cooled and partitioned between water and ethyl acetate, washed with water, brine, dried over sodium sulfate, filtered and concentrated. Purified by Biotage SNAP cartridge KP-Sil column (50 g, heptane:ethyl acetate=1:0, 1:1 to 0:1 then dichloromethane:methanol=1:0, 20:1) to give 1.335 g brown solid as 3-amino-4-(methylamino)-6-(4-(pyridin-3-ylmethoxy)-3-(trifluoromethyl)phenyl)picolinonitrile (53%).

$^1$H NMR (DMSO-d6) δ: 8.69 (d, 1H, J=1.3 Hz), 8.56 (dd, 1H, J=4.7, 1.3 Hz), 8.15-8.25 (m, 2H), 7.86 (d, 1H, J=7.9 Hz), 7.40-7.50 (m, 2H), 6.96 (s, 1H), 6.27 (d, 1H, J=4.7 Hz), 5.70 (s, 2H), 5.38 (s, 2H), 2.91 (d, 3H, J=4.6 Hz).

D: 1-Methyl-6-(4-(pyridin-3-ylmethoxy)-3-(trifluoromethyl)phenyl)-1H-[1,2,3]triazolo[4,5-c]pyridine-4-carbonitrile To a suspension of 3-amino-4-(methylamino)-6-(4-(pyridin-3-ylmethoxy)-3-(trifluoromethyl)phenyl)picolinonitrile (1.33 g) in water (15 ml) and 1,4-dioxane (15 ml), 2N hydrochloric acid (2.5 ml) was added at 0° C. and sodium nitrite (0.332 g) in water (3 ml) was added then stirred at 0° C. for 10 min then at 20° C. for 70 h. The reaction mixture was filtered, washed with water, dried in vacuum oven to give 1.14 g brown solid. Purified by Biotage SNAP cartridge KP-Sil column (100 g, heptane:ethyl acetate=1:0, 2:1, 1:1, 1:2 to 0:1 then ethyl acetate:methanol=25:1, 20:1 to 15:1 then dichloromethane:methanol=15:1, 10:1), fractions were passed through Strata SCX column (5 g) to give 560.7 mg light brown solid as 1-methyl-6-(4-(pyridin-3-ylmethoxy)-3-(trifluoromethyl)phenyl)-1H-[1,2,3]triazolo[4,5-c]pyridine-4-carbonitrile (41%).

$^1$H NMR (CDCl$_3$) δ: 8.74 (s, 1H), 8.63 (d, 1H, J=4.3 Hz), 8.35 (dd, 1H, J=8.7, 2.2 Hz), 8.32 (d, 1H, J=2.0 Hz), 7.98 (s, 1H), 7.86 (d, 1H, J=7.8 Hz), 7.39 (dd, 1H, J=7.8, 4.9 Hz), 7.23 (d, 1H, J=8.9 Hz), 5.32 (s, 2H), 4.45 (s, 3H). MS m/z: 411 (M+H).

EXAMPLE 23 methyl-6-(4-(1-N-oxy-pyridin-3-ylmethoxy)-3-(trifluoromethyl)phenyl)-1H-[1,2,3]triazolo[4,5-c]pyridine-4-carbonitrile

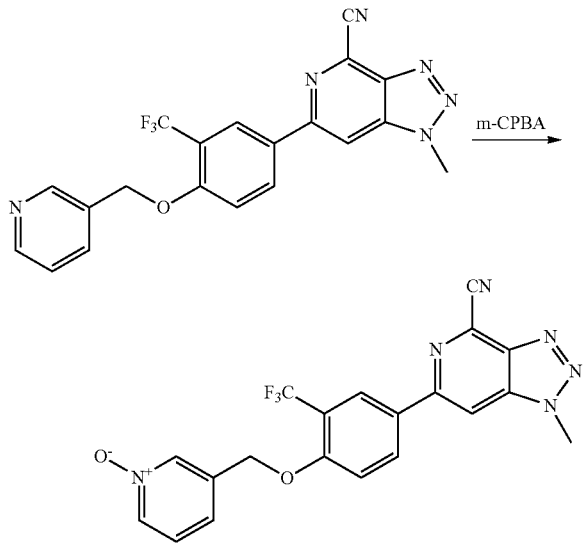

To a suspension of 1-methyl-6-(4-(pyridin-3-ylmethoxy)-3-(trifluoromethyl)phenyl)-1H-[1,2,3]triazolo[4,5-c]pyridine-4-carbonitrile (110 mg) in dichloromethane (5 ml), 3-chloroperoxybenzoic acid (0.603 mmol, 139 mg) was added at 0° C. and stirred at 0° C. for 0.5 h then at 20° C. for 3 h. The reaction mixture was diluted with ethyl acetate and water, extracted with ethyl acetate, washed with 5% sodium bicarbonate solution, dried over sodium sulfate, filtered and concentrated. Dichloromethane and methanol were added to the solid, filtered and washed with dichloromethane and methanol, dried in vacuum oven to give 50 mg orange solid as 3-((4-(4-cyano-1-methyl-1H-[1,2,3]triazolo[4,5-c]pyridin-6-yl)-2-(trifluoromethyl)-phenoxy)methyl)pyridine 1-oxide (58%).

$^1$H NMR (DMSO-d6) δ: 9.01 (s, 1H), 8.53 (d, 1H, J=8.8 Hz), 8.50 (s, 1H), 8.34 (s, 1H), 8.23 (d, 1H, J=6.3 Hz), 7.59 (d, 1H, J=8.8 Hz), 7.45-7.55 (m, 1H), 7.42 (d, 1H, J=8.0 Hz), 5.42 (s, 2H), 4.46 (s, 3H).

MS m/z: 427 (M+H).

EXAMPLE 24

1-methyl-6-(4-(pyridin-4-ylmethoxy)-3-(trifluoromethyl)phenyl)-1H-[1,2,3]triazolo[4,5-c]pyridine-4-carbonitrile

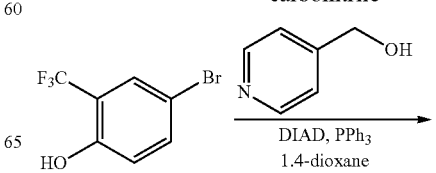

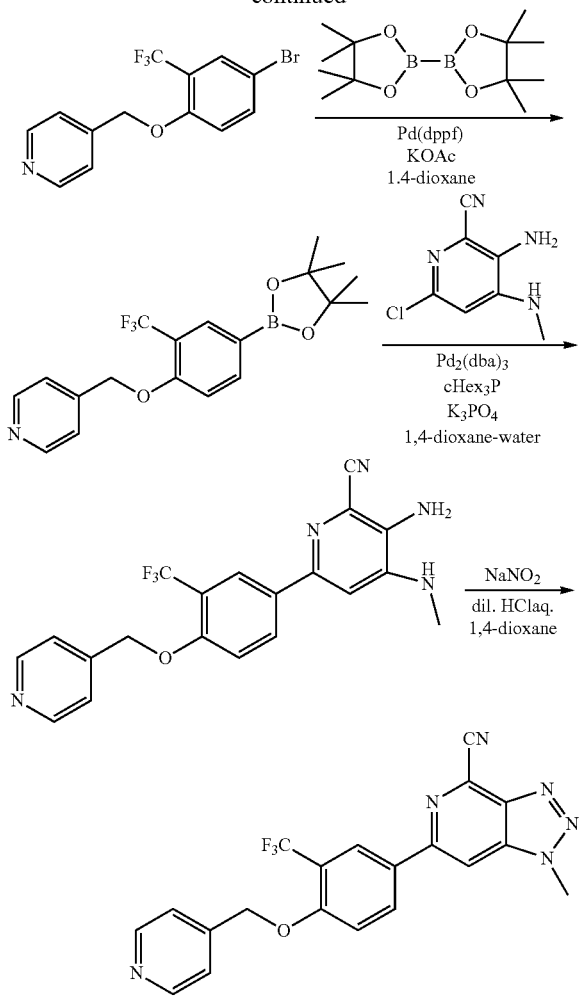

A: 4-((4-Bromo-2-(trifluoromethyl)phenoxy)methyl) pyridine

To a suspension of 4-bromo-2-(trifluoromethyl)phenol (8.00 g) in 1,4-dioxane (100 ml), triphenylphosphine (10.99 g) and 4-pyridylcarbinol (3.84 g) were added. Then diisopropyl azodicarboxylate (8.93 g) was dropwised and stirred at 20° C. for 18 h. The mixture was evaporated off the solvent, diethyl ether (100 ml) and iso-hexane (25 ml) were added and stirred at 20° C. for 2 h, stood for 3 days, filtered and washed with diethyl ether and iso-hexane. The filtrate was concentrated and purified by Biotage SNAP cartridge KP-Sil column (100 g, heptane:ethyl acetate=1:0, 2:1 to 1:1) to give 11.16 g red-orange oil as 4-((4-bromo-2-(trifluoromethyl)phenoxy) methyl)-pyridine (80% purity).

¹H NMR (CDCl₃) δ: 8.64 (d, 2H, J=6.0 Hz), 7.74 (d, 1H, J=2.4 Hz), 7.59 (dd, 1H, J=8.8, 2.4 Hz), 7.35 (d, 2H, J=5.9 Hz), 6.87 (d, 1H, J=8.8 Hz), 5.17 (s, 2H).

B: 4-((4-(4,4,5,5-Tetramethyl-1,3,2-dioxaborolan-2-yl)-2-(trifluoromethyl)phenoxy)-methyl)pyridine A suspension of 4-((4-bromo-2-(trifluoromethyl)phenoxy)methyl)pyridine (11.15 g), bis(pinacolato)diboron (8.70 g), 1,1'-bis(diphenylphosphino)ferrocenedichloropalladium(II) (0.982 g) and potassium acetate (7.99 g) in dry 1,4-dioxane (50 ml) was stirred at 100° C. for 2 h. The solvent was evaporated and partitioned between water and dichloromethane then separated. The aqueous layer was extracted further with dichloromethane, combined organic layer was dried over sodium sulfate, filtered and concentrated. Purified by Biotage SNAP cartridge KP-Sil column (100 g, heptane: ethyl acetate=1:0, 3:1, 2:1 to 1:1) to give 10.345 g orange oil. Dissolved in diethyl ether (20 ml), 2N hydrochloric acid in diethyl ether (15 ml) was added, filtered to collect the precipitate and washed with diethyl ether to give colourless solid. This solid was partitioned between ethyl acetate and water then neutralised with saturated sodium bicarbonate solution then separated. The aqueous layer was extracted further with ethyl acetate, combined organic layer was dried over sodium sulfate, filtered and concentrated to give 7.005 g light brown solid as 4-((4-(4,4,5,5-tetramethyl-1,3,2-dioxaborolan-2-yl)-2-(trifluoromethyl)phenoxy)methyl)-pyridine (69%).

¹H NMR (CDCl₃) δ: 8.63 (d, 2H, J=3.1 Hz), 8.07 (s, 1H), 7.92 (d, 1H, J=8.2 Hz), 7.38 (d, 2H, J=3.9 Hz), 6.97 (d, 1H, J=8.3 Hz), 5.22 (s, 2H), 1.34 (s, 12H).

C: 3-Amino-4-(methylamino)-6-(4-(pyridin-4-ylmethoxy)-3-(trifluoromethyl)-phenyl)picolinonitrile A suspension of 4-((4-(4,4,5,5-tetramethyl-1,3,2-dioxaborolan-2-yl)-2-(trifluoromethyl)phenoxy)methyl)pyridine (1.39 g), 3-amino-6-chloro-4-(methylamino)-picolinonitrile (0.669 g), tris(dibenzylideneacetone)dipalladium (0) (173 mg), tricyclohexylphosphine (127 mg) and potassium phosphate (1.621 g) in 1,4-dioxane (15 ml) and water (7.5 ml) was stirred at 100° C. for 2 h. The reaction mixture was cooled, filtered to remove insoluble precipitate. The precipitate was dried in vacuum oven to give 430 mg light brown solid as 3-amino-4-(methylamino)-6-(4-(pyridin-4-ylmethoxy)-3-(trifluoromethyl)phenyl)picolinonitrile (29%). Filtrate was partitioned between water and ethyl acetate, washed with water, dried over sodium sulfate, filtered and concentrated. Purified by Biotage SNAP cartridge KP-Sil column (25 g, heptane:ethyl acetate=1:0, 1:1, 1:3 to 0:1 then ethyl acetate: methanol=25:1, 20:1 then dichloromethane:methanol=20:1) to give 568 mg of the title compound as a light brown solid (39%).

¹H NMR (DMSO-d6) δ: 8.61 (d, 2H, J=6.0 Hz), 8.15-8.25 (s+d, 2H), 7.44 (d, 2H, J=6.0 Hz), 7.34 (d, 1H, J=9.5 Hz), 6.96 (s, 1H), 6.27 (d, 1H, J=4.6 Hz), 5.70 (s, 2H), 5.41 (s, 2H), 2.90 (d, 3H, J=4.7 Hz).

D: 1-Methyl-6-(4-(pyridin-4-ylmethoxy)-3-(trifluoromethyl)phenyl)-1H-[1,2,3]-triazolo[4,5-c]pyridine-4-carbonitrile To a suspension of 3-amino-4-(methylamino)-6-(4-(pyridin-4-ylmethoxy)-3-(trifluoromethyl)phenyl)picolinonitrile (580 mg) in water (5 ml) and 1,4-dioxane (5 ml), 2N hydrochloric acid (1.089 ml) was added at 0° C. and sodium nitrite (145 mg) in water (1 ml) was added then stirred at 0° C. for 10 min then at 20° C. for 70 h. The reaction mixture was filtered, washed with water, dried in vacuum oven to give 410 mg brown solid. Purified by Biotage SNAP cartridge KP-Sil column (25 g, dichloromethane:methanol=1:0, 20:1 to 10:1) then passed through Strata SCX column (20 g) to give 495 mg brown solid as 1-methyl-6-(4-(pyridin-4-ylmethoxy)-3-(trifluoromethyl)phenyl)-1H-[1,2,3]triazolo[4,5-c]pyridine-4-carbonitrile (83%).

¹H NMR (CDCl₃) δ: 8.67 (d, 2H, J=6.0 Hz), 8.30-8.40 (s+d, 2H), 7.99 (s, 1H), 7.41 (d, 2H, J=6.0 Hz), 7.16 (d, 1H, J=9.0 Hz), 5.31 (s, 2H), 4.45 (s, 3H).

MS m/z: 411 (M+H).

EXAMPLE 25 methyl-6-(4-(1-N-oxy-pyridin-4-ylmethoxy)-3-(trifluoromethyl)phenyl)-1H-[1,2,3]triazolo[4,5-c]pyridine-4-carbonitrile

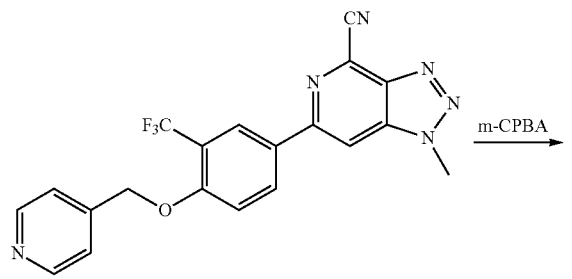

To a suspension of 1-methyl-6-(4-(pyridin-4-ylmethoxy)-3-(trifluoromethyl)-phenyl)-1H-[1,2,3]triazolo[4,5-c]pyridine-4-carbonitrile (76.4 mg) in dichloromethane (5 ml), 3-chloroperoxybenzoic acid (129 mg) was added at 0° C. and stirred at 0° C. for 0.5 h then at 20° C. for 4 h (precipitate formed). Dichloromethane and methanol were added to the reaction mixture, filtered and washed with dichloromethane and methanol, dried in vacuum oven to give 60 mg light pink solid as 4-((4-(4-cyano-1-methyl-1H-[1,2,3]triazolo[4,5-c]pyridin-6-yl)-2-(trifluoromethyl)phenoxy)methyl)-pyridine 1-oxide (76%).

$^1$H NMR (DMSO-d6) δ: 9.00 (s, 1H), 8.52 (d, 1H, J=8.8 Hz), 8.50 (s, 1H), 8.29 (d, 2H, J=6.9 Hz), 7.57 (d, 1H, J=8.8 Hz), 7.48 (d, 2H, J=6.9 Hz), 5.41 (s, 2H), 4.46 (s, 3H).

MS m/z: 427 (M+H).

EXAMPLE 26

1-Methyl-6-(6-(2-(piperidin-4-yl)ethoxy)-5-(trifluoromethyl)pyridin-3-yl)-1H-[1,2,3]-triazolo[4,5-c]pyridine-4-carbonitrile trifluoroacetate

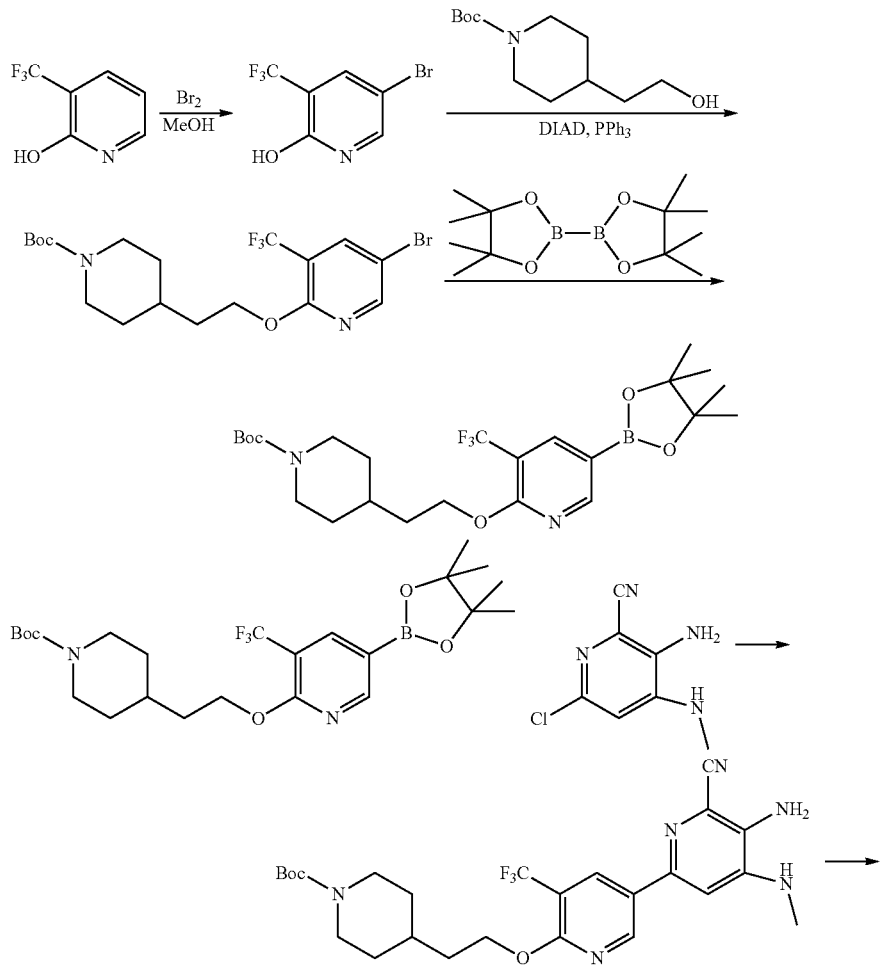

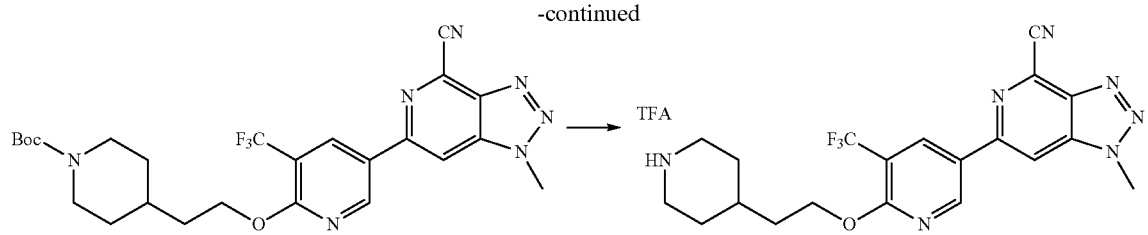

A: 5-Bromo-2-hydroxy-3-(trifluoromethyl)pyridine (WO2005/058848, pp. 59)

A solution of 2-hydroxy-3-(trifluoromethyl)pyridine (10.0 g) and bromine (3.08 ml, 9.60 g) in methanol (50 ml) was stirred at 20° C. for 22 h. The solution was concentrated and the residue partitioned between ethyl acetate (400 ml) and water (100 ml). The layers were separated and the organic layer was washed with 5% $Na_2S_2O_3$aq. (100 ml) and brine (100 ml), dried over sodium sulphate, filtered and concentrated. Purified by Biotage SNAP cartridge KP-Sil column twice (100 g, heptane:ethyl acetate=1:0, 3:1 to 2:1) to give 13.69 g light yellow solid as 5-bromo-2-hydroxy-3-(trifluoromethyl)pyridine (95%).

$^1$H NMR (CDCl$_3$) δ: 13.0 (br, 1H), 7.91 (d, 1H, J=2.8 Hz), 7.73 (d, 1H, J=2.8 Hz).

B: tert-Butyl 4-(2-(5-bromo-3-(trifluoromethyl)pyridin-2-yloxy)ethyl)piperidine-1-carboxylate To a suspension of 5-bromo-2-hydroxy-3-(trifluoromethyl)pyridine (6.90 g) in 1,4-dioxane (100 ml), triphenylphosphine (9.44 g) and tert-butyl 4-(2-hydroxyethyl)-piperidine-1-carboxylate (7.41 g) were added. Then diisopropyl azodicarboxylate (DIAD, 7.52 ml, 7.67 g) was added dropwise and stirred at 20° C. for 18 h. Solvent was then removed under reduced pressure and residue purified by Biotage SNAP cartridge KP-Sil column (340 g, hepane:ethyl acetate=1:0, 5:1 to 4:1) to give 9.0 g orange oil as tert-butyl 4-(2-(5-bromo-3-(trifluoromethyl)pyridin-2-yloxy)ethyl)-piperidine-1-carboxylate (70%).

$^1$H NMR (CDCl$_3$) δ: 8.33 (d, 1H, J=2.4 Hz), 7.93 (d, 1H, J=2.4 Hz), 4.44 (t, 2H, J=6.4 Hz), 4.08 (d, 2H, J=12.8 Hz), 2.69 (t, 2H, J=12.2 Hz), 1.60-1.80 (m, 5H), 1.45 (s, 9H), 1.05-1.20 (m, 2H).

C: tert-Butyl 4-(2-(5-(4,4,5,5-tetramethyl-1,3,2-dioxaborolan-2-yl)-3-(trifluoromethyl)-pyridin-2-yloxy) ethyl)piperidine-1-carboxylate A suspension of tert-butyl 4-(2-(5-bromo-3-(trifluoromethyl)pyridin-2-yloxy)-ethyl)piperidine-1-carboxylate (8.98 g), bis(pinacolato)diboron (7.70 g), 1,1'-bis-(diphenylphosphino)ferrocenedichloropalladium (II) (0.72 g) and potassium acetate (5.89 g) in dry 1,4-dioxane (40 ml) was stirred at 100° C. under nitrogen for 3 h. The solvent was removed under reduced pressure, and residue partitioned between water and dichloromethane. The aqueous layer was extracted further with dichloromethane, combined dichloromethane layer was dried over sodium sulphate, filtered and concentrated. Purified by Biotage SNAP cartridge KP-Sil column (340 g, hepane:ethyl acetate=1:0 to 4:1) to give 9.99 g colorless amorphous as tert-butyl 4-(2-(5-(4,4,5,5-tetramethyl-1,3,2-dioxaborolan-2-yl)-3-(trifluoromethyl)pyridin-2-yloxy) ethyl)piperidine-1-carboxylate (101%, 70% purity).

$^1$H NMR (CDCl$_3$) δ: 8.63 (s, 1H), 8.19 (s, 1H), 4.50 (t, 2H, J=6.4 Hz), 4.07 (d, 2H, J=10.8 Hz), 2.69 (t, 2H, J=12.2 Hz), 1.60-1.80 (m, 5H), 1.45 (s, 9H), 1.34 (s, 12H), 1.05-1.20 (m, 2H).

D: tert-Butyl 4-(2-(5-amino-6-cyano-4-(methylamino)-5'-(trifluoromethyl)-2,3'-bipyridin-6'-yloxy) ethyl)piperidine-1-carboxylate A suspension of tert-butyl 4-(2-(5-(4,4,5,5-tetramethyl-1,3,2-dioxaborolan-2-yl)-3-(trifluoromethyl)pyridin-2-yloxy) ethyl)piperidine-1-carboxylate (8.95 g), 3-amino-6-chloro-4-(methylamino)picolinonitrile (2.29 g), tris (dibenzylideneacetone)dipalladium (0) (0.59 g), tricyclohexylphosphine (0.43 g) and potassium phosphate (5.48 g) in 1,4-dioxane (80 ml) and water (40 ml) was stirred at 100° C. under nitrogen for 2 h. The reaction mixture was cooled and partitioned between water and ethyl acetate, washed with water, brine, dried over sodium sulphate, filtered and concentrated. Purified by Biotage SNAP cartridge KP-Sil column (340 g, heptane:ethyl acetate=1:0, 2:1, 1:1 to 1:2) to give 6.43 g light brown solid as tert-butyl 4-(2-(5-amino-6-cyano-4-(methylamino)-5'-(trifluoromethyl)-2,3'-bipyridin-6'-yloxy)ethyl)piperidine-1-carboxylate (99%, 90% purity).

$^1$H NMR (DMSO-d6) δ: 8.99 (d, 1H, J=2.4 Hz), 8.51 (d, 1H, J=2.4 Hz), 7.05 (s, 1H), 6.35 (q, 1H, J=4.7 Hz), 5.83 (s, 2H), 4.50 (t, 2H, J=6.4 Hz), 3.85-4.00 (m, 2H), 2.91 (d, 3H, J=4.8 Hz), 2.55-2.80 (m, 2H), 1.55-1.80 (m, 5H), 1.39 (s, 9H), 1.00-1.15 (m, 2H).

E: tert-Butyl 4-(2-(5-(4-cyano-1-methyl-1H-[1,2,3] triazolo[4,5-c]pyridin-6-yl)-3-(trifluoromethyl)pyridin-2-yloxy)ethyl)piperidine-1-carboxylate To a suspension of tert-butyl 4-(2-(5-amino-6-cyano-4-(methylamino)-5'-(trifluoromethyl)-2,3'-bipyridin-6'-yloxy) ethyl)piperidine-1-carboxylate (5.20 g) in water (40 ml) and 1,4-dioxane (40 ml) was added 2N hydrichloric acid (6.89 ml) at 0° C. To above suspension was then added dropwise sodium nitrite (0.92 g) in water (10 ml). The mixture was then stirred at 0° C. for 10 min and at 20° C. for 16 h. The solid product was collected by filtration and washed with water, dried in vacuum oven to give 4.61 g tert-butyl 4-(2-(5-(4-cyano-1-methyl-1H-[1,2,3]triazolo[4,5-c]pyridin-6-yl)-3-(trifluoro-methyl)pyridin-2-yloxy)ethyl)piperidine-1-carboxylate (94%).

$^1$H NMR (CDCl$_3$) δ: 9.01 (d, 1H, J=2.4 Hz), 8.59 (d, 1H, J=2.4 Hz), 7.96 (s, 1H), 4.58 (t, 2H, J=6.4 Hz), 4.44 (s, 3H), 4.10 (d, 2H, J=10.0 Hz), 2.72 (d, 2H, J=12.4 Hz), 1.60-1.85 (m, 5H), 1.46 (s, 9H), 1.10-1.30 (m, 2H).

F: 1-Methyl-6-(6-(2-(piperidin-4-yl)ethoxy)-5-(trifluoromethyl)pyridin-3-yl)-1H-[1,2,3]triazolo[4,5-c] pyridine-4-carbonitrile trifluoroacetate To a solution of tert-butyl 4-(2-(5-(4-cyano-1-methyl-1H-[1,2,3]triazolo[4,5-c]pyridin-6-yl)-3-(trifluoromethyl)pyridin-2-yloxy)ethyl)piperidine-1-carboxylate (1.15 g) in dichloromethane (10 ml) and acetonitrile (5 ml), trifluoroacetic acid (2 ml) was added and the mixture stirred at 20° C. for 1 h then solvent evaporated under reduced pressure. The resulting residue was dissolved in ethyl acetate (10 ml) and diethyl ether added dropwise until the mixture turned cloudy. The solution was allowed to stand for two hours. The desired product was collected by filtration and washed with ether, dried in vacuum oven to give 920 mg 1-methyl-6-(6-(2-(piperidin-4-yl)ethoxy)-5-(trifluoromethyl)pyridin-3-yl)-1H-[1,2,3]triazolo[4,5-c]pyridine-4-carbonitrile trifluoroacetate (78%).

$^1$H NMR (CD$_3$OD-d4) δ: 9.19 (s, 1H), 8.78 (s, 1H), 8.69 (s, 1H), 4.64 (t, 2H, J=6.0 Hz), 4.47 (s, 3H), 3.40 (d, 2H, J=12.8 Hz), 2.99 (dt, 2H, J=12.8, 2.8 Hz), 2.07 (d, 2H, J=14.4 Hz), 1.80-2.00 (t+m, 3H), 1.40-1.60 (m, 2H). MS m/z: 432 (M+H).

EXAMPLE 27a 6-(6-(2-(1-(2-Dimethylamino-2-oxo-ethyl)piperidin-4-yl)ethoxy)-5-(trifluoromethyl)pyridin-3-yl)-1-methyl-1H-[1,2,3]triazolo[4,5-c]pyridine-4-carbonitrile hydrochloride

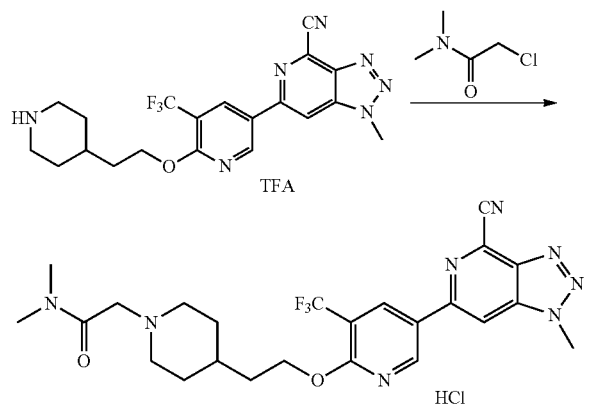

To a solution of 1-methyl-6-(6-(2-(piperidin-4-yl)ethoxy)-5-(trifluoromethyl)-pyridin-3-yl)-1H-[1,2,3]triazolo[4,5-c]pyridine-4-carbonitrile trifluoroacetate (200 mg) and N,N-diisopropylethylamine (310 μl) in acetonitrile (8 ml), 2-chloro-N,N-dimethylacetamide (77 μl, 91 mg) was added and the mixture stirred at 20° C. for 65 h. The reaction mixture was concentrated. The residue diluted with water (20 ml) and extrated with DCM (50 ml×3), combined DCM layer dried over sodium sulphate and solvent removed under reduced pressure. The residue was then purified by Strata Si column (5 g, dichloromethane:methanol=1:0, 25:1 to 15:1), converted to hydrochloric acid salt using 2N hydrochloric acid in diethyl ether to give 1-methyl-6-(6-(2-(1-(2-dimethylamino-2-oxo-ethyl)piperidin-4-yl)ethoxy)-5-(trifluoromethyl)pyridin-3-yl)-1H-[1,2,3]triazolo[4,5-c]pyridine-4-carbonitrile hydrochloride (179 mg).

$^1$H NMR (CD$_3$OD-d4) δ: 9.19 (d, 1H, J=2.4 Hz), 8.78 (d, 1H, J=2.0 Hz), 8.69 (s, 1H), 4.65 (t, 2H, J=5.6 Hz), 4.47 (s, 3H), 4.15 (brs, 2H), 3.40-3.70 (br, 2H), 2.90-3.10 (2×s+br, 8H), 2.08 (d, 2H, J=14.0 Hz), 1.80-2.00 (t+m, 3H), 1.50-1.80 (m, 2H). MS m/z: 517 (M+H).

The procedure described in Example 27a was further applied, using the appropriate alkylation agent, to prepare the following compounds:

27b: 1-Methyl-6-(6-(2-(1-(2-methylamino-2-oxo-ethyl)piperidin-4-yl)ethoxy)-5-(trifluoromethyl)pyridin-3-yl)-1H-[1,2,3]triazolo[4,5-c]pyridine-4-carbonitrile hydrochloride

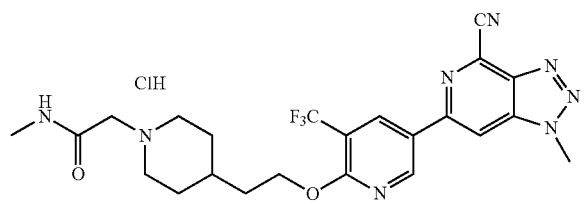 [SMILES: CNC(=O)CN1CCC(CCOc2ncc(-c3cc4c(nnn4C)c(C#N)n3)cc2C(F)(F)F)CC1 ; Cl]

$^1$H NMR (CD$_3$OD-d4) δ: 9.18 (d, 1H, J=2.0 Hz), 8.77 (d, 1H, J=2.4 Hz), 8.69 (s, 1H), 4.64 (t, 2H, J=5.6 Hz), 4.47 (s, 3H), 3.88 (s, 2H), 3.62 (d, 2H, J=12.4 Hz), 3.07 (t, 2H, J=11.6 Hz), 2.11 (d, 2H, J=14.0 Hz), 1.80-2.00 (t+m, 3H), 1.55-1.75 (m, 2H). MS m/z: 503 (M+H).

27c: 6-(6-(2-(1-(2-Amino-2-oxo-ethyl)piperidin-4-yl)ethoxy)-5-(trifluoromethyl)pyridin-3-yl)-1-methyl-1H-[1,2,3]triazolo[4,5-c]pyridine-4-carbonitrile

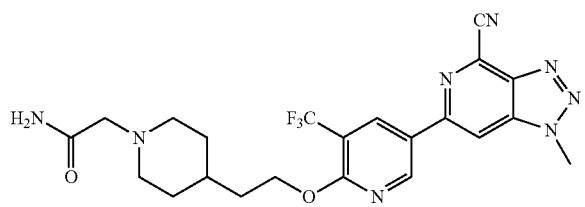 [SMILES: Cn1nnc2c(C#N)nc(-c3cnc(OCCC4CCN(CC(N)=O)CC4)c(C(F)(F)F)c3)cc21]

$^1$H NMR (DMSO-d6) δ: 9.25 (s, 1H), 9.06 (s, 1H), 8.80 (s, 1H), 7.11 (br, 2H), 4.56 (t, 2H, J=6.6 Hz), 4.46 (s, 3H), 2.70-2.90 (s+d, 4H), 1.99 (t, 2H, J=10.6 Hz), 1.60-1.80 (t+t, 4H), 1.40-1.50 (m, 1H), 1.20-1.40 (dq, 2H). MS m/z: 489 (M+H).

27d: 1-Methyl-6-(6-(2-(1-(2-oxo-2-(pyrrolidin-1-yl) ethyl)piperidin-4-yl)ethoxy)-5-(trifluoromethyl)pyridin-3-yl)-1H-[1,2,3]triazolo[4,5-c]pyridine-4-carbonitrile hydrochloride

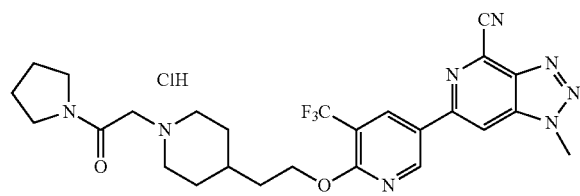 [SMILES: Cn1nnc2c(C#N)nc(-c3cnc(OCCC4CCN(CC(=O)N5CCCC5)CC4)c(C(F)(F)F)c3)cc21 ; Cl]

$^1$H NMR (CD$_3$OD-d4) δ: 9.18 (s, 1H), 8.77 (s, 1H), 8.69 (s, 1H), 4.65 (t, 2H, J=5.8 Hz), 4.47 (s, 3H), 4.12 (s, 2H), 3.62 (d, 2H, J=12.4 Hz), 3.45 (t, 2H, J=6.8 Hz), 3.44 (t, 2H, J=6.8 Hz), 3.08 (t, 2H, J=12.6 Hz), 2.12 (d, 2H, J=14.4 Hz), 2.02 (t, 2H,

J=6.6 Hz), 1.80-2.00 (t+t+m, 5H), 1.67 (dd, 2H, J=24.2 Hz, 11.0 Hz). MS m/z: 543 (M+H).

27e: 1-Methyl-6-(6-(2-(1-(2-morpholino-2-oxoethyl) piperidin-4-yl)ethoxy)-5-(trifluoromethyl)pyridin-3-yl)-1H-[1,2,3]triazolo[4,5-c]pyridine-4-carbonitrile hydrochloride

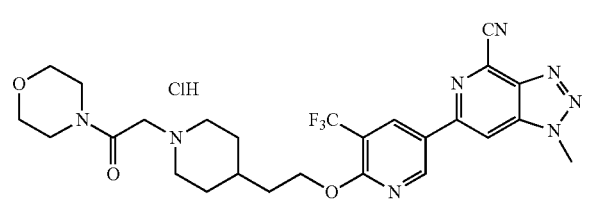 [SMILES: Cn1nnc2c(C#N)nc(-c3cnc(OCCC4CCN(CC(=O)N5CCOCC5)CC4)c(C(F)(F)F)c3)cc21 ; Cl]

¹H NMR (CD₃OD-d4) δ: 9.18 (s, 1H), 8.77 (s, 1H), 8.69 (s, 1H), 4.65 (t, 2H, J=5.6 Hz), 4.47 (s, 3H), 4.23 (s, 2H), 3.60-3.80 (m, 8H), 3.40-3.50 (m, 2H), 3.06 (t, 2H, J=12.6 Hz), 2.12 (d, 2H, J=14.0 Hz), 1.80-2.00 (t+m, 3H), 1.67 (dd, 2H, J=24.2 Hz, 11.0 Hz). MS m/z: 559 (M+H).

27f: 6-(6-(2-(1-(2-Hydroxyethyl)piperidin-4-yl)ethoxy)-5-(trifluoromethyl)pyridin-3-yl)-1-methyl-1H-[1,2,3]triazolo[4,5-c]pyridine-4-carbonitrile

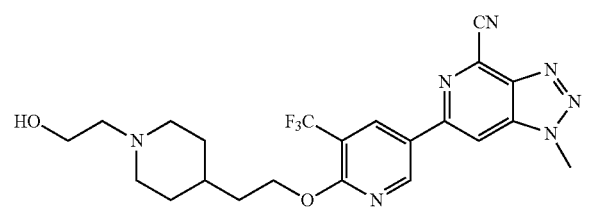 [SMILES: Cn1nnc2c(C#N)nc(-c3cnc(OCCC4CCN(CCO)CC4)c(C(F)(F)F)c3)cc21]

¹H NMR (CD₃OD-d4) δ: 9.17 (s, 1H), 8.76 (s, 1H), 8.68 (s, 1H), 4.60 (t, 2H, J=6.0 Hz), 4.46 (s, 3H), 3.71 (t, 2H, J=6.0 Hz), 2.95-3.20 (m, 2H), 2.62 (br, 2H), 2.10-2.30 (m, 2H), 1.75-1.90 (m, 4H), 1.55-1.70 (br, 1H), 1.30-1.50 (m, 2H). MS m/z: 476 (M+H).

EXAMPLE 28

6-(6-(2-(1-(2-Hydroxy-2-methylpropyl)piperidin-4-yl)ethoxy)-5-(trifluoromethyl)pyridin-3-yl)-1-methyl-1H-[1,2,3]triazolo[4,5-c]pyridine-4-carbonitrile

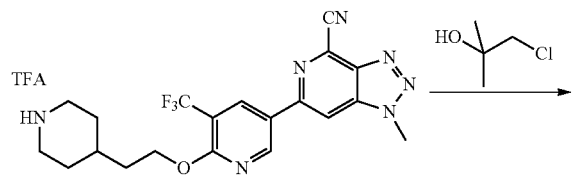

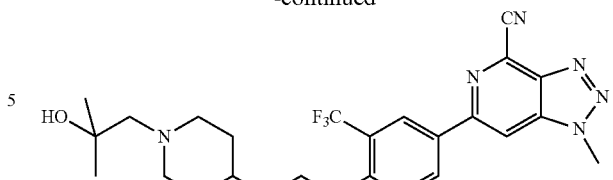

To a solution of 1-methyl-6-(6-(2-(piperidin-4-yl)ethoxy)-5-(trifluoromethyl)-pyridin-3-yl)-1H-[1,2,3]triazolo[4,5-c]pyridine-4-carbonitrile trifluoroacetate (70 mg) and N,N-diisopropylethylamine (85 mg) in acetonitrile (2 ml), 1-chloro-2-methylpropan-2-ol (48 mg) and sodium iodide (19 mg) were added and heated in microwave at 160° C. for 0.5 h. The reaction mixture was concentrated then diluted with dichloromethane and water, extracted with dichloromethane and separated by hydrophobic frits, concentrated. Purified by Strata Si column (5 g, dichloromethane:methanol=1:0, 25:1, 15:1, 12.5:1 to 10:1) then passed through Strata SCX column (1 g) to give 20.0 mg yellow amorphous as 6-(6-(2-(1-(2-hydroxy-2-methylpropyl)piperidin-4-yl)ethoxy)-5-(trifluoromethyl)pyridin-3-yl)-1-methyl-1H-[1,2,3]triazolo[4,5-c]pyridine-4-carbonitrile (31%).

¹H NMR (CD₃OD-d4) δ: 9.16 (s, 1H), 8.75 (s, 1H), 8.66 (s, 1H), 4.59 (t, 2H, J=6.4 Hz), 4.46 (s, 3H), 2.98 (t, 2H, J=11.6 Hz), 2.30 (s, 2H), 2.23 (d, 2H, J=11.6 Hz), 1.70-1.85 (q+d, 4H), 1.45-1.60 (br, 1H), 1.38 (dq, 2H, J=12.0 Hz, 3.30 Hz), 1.17 (s, 6H). MS m/z: 504 (M+H).

EXAMPLE 29

6-(4-(2-(1-(1-aminocyclopropanecarbonyl)piperidin-4-yl)ethoxy)-3-(trifluoromethyl)phenyl)-1-methyl-1H-[1,2,3]triazolo[4,5-d]pyridine-4-carbonitrile

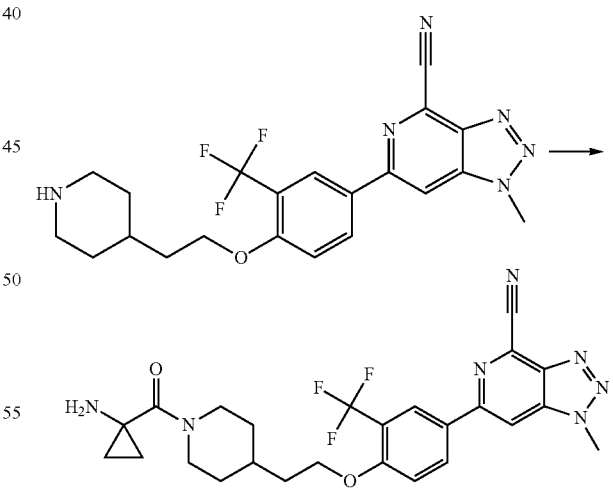

1-Methyl-6-(4-(2-(piperidin-4-yl)ethoxy)-3-(trifluoromethyl)phenyl)-1H-[1,2,3]triazolo[4,5-c]pyridine-4-carbonitrile (76 mg), Boc-1-aminocyclopropane-1-carboxylic (71.1 mg) and DIPEA (146 μl) were dissolved in NMP (2 ml) and HATU (0.265 mmol, 101 mg) was then added. The reaction was stirred at room temperature for 72 hours then diluted with EtOAc (20 ml) and washed with 1:1 saturated sodium bicarbonate solution/water (3×15 ml). Organics were dried over sodium sulphate and solvent evaporated under reduced pressure. The resulting residue was re-dissolved in DCM (1 ml) and acetonitrile (200 μl) and trifluoroacetic acid (200 μl) added. The mixture was stirred for 30 minutes at room temperature then solvent evaporated under reduced pressure. Toluene (500 μl) was added and then removed under reduced pressure. The resulting brown residue was purified by flash chromatography (10 g silica column, DCM to 5% MeOH in DCM gradient). Solvent was evaporated under reduced pressure and the resulting solid was washed with DCM and ether and dried under vacuum to afford desired product 6-(4-(2-(1-(1-aminocyclopropanecarbonyl)piperidin-4-yl)ethoxy)-3-(trifluoromethyl)phenyl)-1-methyl-1H-[1,2,3]triazolo[4,5-c]pyridine-4-carbonitrile (52% yield) as a solid.

$^1$H NMR (CD3OD) δ: 8.57 (s, 1H), 8.45 (s, 2H), 8.44 (d, 1H), 7.38 (d, 1H), 4.45 (s, 3H), 4.30 (d, 2H), 4.27 (t, 2H), 2.90 (t, 2H), 1.95 (m, 1H), 1.86 (t, 2H), 1.37 (m, 4H), 1.22 (m, 2H), 1.12 (m, 2H). MS m/z 514.2 (M+H).

EXAMPLE 30

6-(4-(2-(azetidin-3-yl)ethoxy)-3-(trifluoromethyl)phenyl)-1-methyl-1H-[1,2,3]triazolo[4,5-d]pyridine-4-carbonitrile 2,2,2-trifluoroacetate

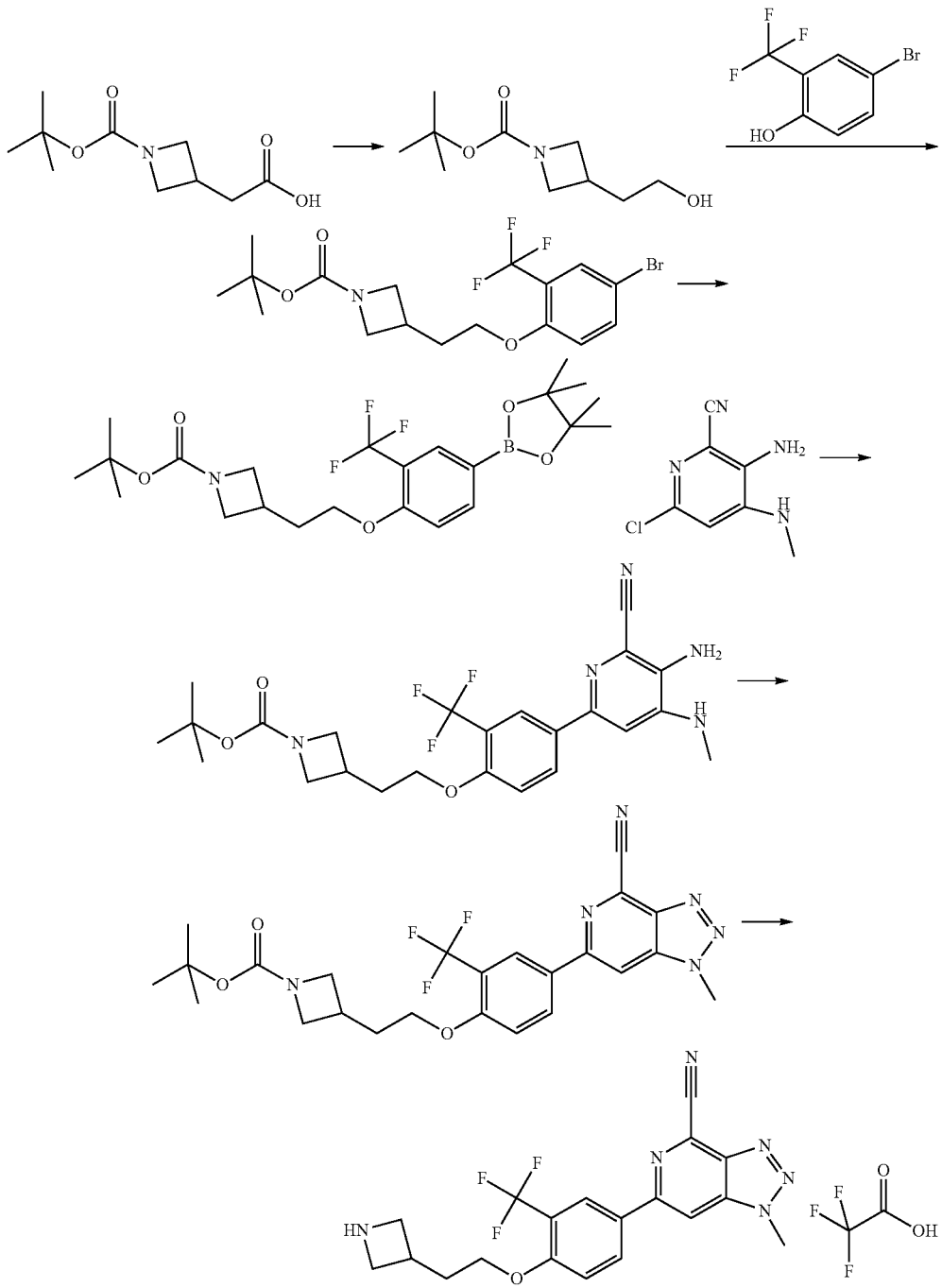

A: tert-butyl 3-(2-hydroxyethyl)azetidine-1-carboxylate 2-(1-(tert-Butoxycarbonyl)azetidin-3-yl)acetic acid (3.91 g) was dissolved in THF (18.17 ml) and cooled to 0° C. Diborane (1M in THF, 54.5 ml) was added dropwise and the reaction stirred for one hour. Water was added dropwise to quench unreacted borane and the mixture diluted with EtOAc (150 mL) and washed with water (100 mL). Organics were dried over sodium sulphate and solvent evaporated under reduced pressure to afford tert-butyl 3-(2-hydroxyethyl)azetidine-1-carboxylate (100% yield) as a clear oil.

$^1$H NMR (CDCl3) δ: 4.0 (t, 2H), 3.60 (m, 4H), 2.65 (m, 1H), 1.85 (m, 2H), 1.43 (s, 9H).

B: tert-butyl 3-(2-(4-bromo-2-(trifluoromethyl)phenoxy)ethyl)azetidine-1-carboxylate 4-Bromo-2-(trifluoromethyl)phenol (3 g), tert-butyl 3-(2-hydroxyethyl)azetidine-1-carboxylate (2.81 g) and triphenylphosphine (3.92 g) were dissolved in DCM (25 ml). The reaction mixture was placed under a nitrogen atmosphere and cooled to 0° C. then DIAD (2.94 ml) was added dropwise. The mixture was stirred at room temperature for 16 hours then solvent evaporated under reduced pressure. The resulting residue was dissolved in ether (10 ml), heptane (15 mL) was then added and the suspension stirred for 45 minutes. The mixture was filtered (solid was washed with 3:2 heptane/ether) and the filtrate washed with NaOH (1M, 2×40 mL). Organics were dried over sodium sulphate and solvent evaporated under reduced pressure to yield crude product as a clear oil (6.05 g). Purification by flash chromatography (100 g silica column, 10% to 25% EtOAc in heptane gradient) afforded tert-butyl 3-(2-(4-bromo-2-(trifluoromethyl)phenoxy)ethyl)azetidine-1-carboxylate (52.6% yield) as a clear oil.

$^1$H NMR (CDCl3) δ: 7.70 (s, 1H), 7.57 (d, 1H), 6.85 (d, 1H), 4.08 (t, 2H), 4.02 (t, 2H), 3.65 (m, 2H), 1.78 (m, 1H), 2.10 (m, 2H), 1.44 (s, 9H).

C: tert-butyl 3-(2-(4-(4,4,5,5-tetramethyl-1,3,2-dioxaborolan-2-yl)-2-(trifluoromethyl)phenoxy)ethyl)azetidine-1-carboxylate tert-Butyl 3-(2-(4-bromo-2-(trifluoromethyl)phenoxy)ethyl)azetidine-1-carboxylate (2.78 g), bis(pinacolato)diboron (1.997 g), 1,1'-bis(diphenylphosphino)-ferrocenedichloropalladium (II) (0.237 g) and potassium acetate (1.286 g) were combined in DMSO (26 ml) and heated to 80° C. under nitrogen for 3 hours. The reaction was allowed to cool to room temperature, EtOAc (300 ml) added and the mixture filtered through celite and washed with water (2×150 ml) and brine (75 ml). Organics were dried over sodium sulphate and solvent evaporated under reduced pressure to yield crude product as a brown oil. Purification by flash chromatography (100 g silica column, 20% EtOAc/heptane mobile phase) afforded tert-butyl 3-(2-(4-(4,4,5,5-tetramethyl-1,3,2-dioxaborolan-2-yl)-2-(trifluoromethyl)phenoxy)ethyl)-azetidine-1-carboxylate (61% yield) as a clear oil.

NMR (CDCl3) δ: 8.05 (s, 1H), 7.90 (d, 1H), 6.92 (d, 1H), 4.08 (t, 4H), 3.62 (m, 2H), 2.75 (m, 1H), 2.10 (m, 2H), 1.44 (s, 9H), 1.34 (s, 12H).

D: tert-butyl 3-(2-(4-(5-amino-6-cyano-4-(methylamino)pyridin-2-yl)-2-(trifluoromethyl)phenoxy)ethyl)azetidine-1-carboxylate A solution of tert-butyl 3-(2-(4-(4,4,5,5-tetramethyl-1,3,2-dioxaborolan-2-yl)-2-(trifluoromethyl)phenoxy)ethyl)azetidine-1-carboxylate (413 mg) in dioxane (3 ml) was added to a flask charged with 3-amino-6-chloro-4-(methylamino)picolinonitrile (160 mg), tris(dibenzylideneacetone)dipalladium (0) (40.1 mg), tricyclohexylphosphine (29.5 mg) and potassium phosphate (372 mg). Water (1.2 ml) was added and the reaction was placed under a nitrogen atmosphere and heated to 100° C. for 2 hours. The mixture was allowed to cool to room temperature then diluted with EtOAc (150 ml) filtered through celite and washed with water (2×100 ml) and brine (50 ml). Organics were dried over sodium sulphate and solvent evaporated under reduced pressure to afford crude product as a brown oil. Purification by flash chromatography (50 g silica column, DCM to 5% MeOH in DCM mobile phase) afforded product still containing minor impurities. DCM was added to the residue causing solid to crash out of solution. The solid was collected by filtration and washed with ether to yield desired product tert-butyl 3-(2-(4-(5-amino-6-cyano-4-(methylamino)pyridin-2-yl)-2-(trifluoromethyl)phenoxy)ethyl)azetidine-1-carboxylate.

NMR (DMSO) δ: 8.18 (d, 1H), 8.15 (s, 1H), 7.28 (d, 1H), 6.95 (s, 1H), 6.26 (broad m, 1H), 5.70 (broad s, 2H), 4.15 (t, 2H), 3.92 (broad m, 2H), 3.60 (broad m, 2H), 3.33 (s, 3H) 2.68 (m, 1H), 2.05 (m, 2H), 1.37 (s, 9H).

E: tert-butyl 3-(2-(4-(4-cyano-1-methyl-1H-[1,2,3]triazolo[4,5-c]pyridin-6-yl)-2-(trifluoromethyl)phenoxy)ethyl)azetidine-1-carboxylate tert-Butyl 3-(2-(4-(5-amino-6-cyano-4-(methylamino)pyridin-2-yl)-2-(trifluoro-methyl)phenoxy)ethyl)azetidine-1-carboxylate (100 mg) was dissolved in NMP (1000 µl) and hydrochloric acid (1M, 407 µl) added. A solution of sodium nitrite (20 mg) in water (150 µl) was added at room temperature and the reaction stirred for 1 hour. The reaction mixture was diluted with EtOAc (30 ml) and washed with water (3×20 ml) and brine (20 ml). Organics were dried over sodium sulphate and solvent evaporated under reduced pressure to yield crude product as a brown oil. Purification by flash chromatography (DCM to 2% MeOH in DCM mobile phase, 10 g silica column) afforded product tert-butyl 3-(2-(4-(4-cyano-1-methyl-1H-[1,2,3]triazolo[4,5-c]pyridin-6-yl)-2-(trifluoromethyl)phenoxy)ethyl)azetidine-1-carboxylate (84% yield).

$^1$H NMR (CD3OD) δ: 8.59 (s, 1H), 8.45 (s, 1H), 8.43 (d, 1H), 7.35 (d, 1H), 4.45 (s, 3H), 4.22 (t, 2H), 4.05 (m, 2H), 3.70 (broad m, 2H), 2.80 (m, 1H), 2.15 (m, 2H), 1.44 (s, 9H).

F: 6-(4-(2-(azetidin-3-yl)ethoxy)-3-(trifluoromethyl)phenyl)-1-methyl-1H-[1,2,3]triazolo[4,5-c]pyridine-4-carbonitrile 2,2,2-trifluoroacetate tert-Butyl 3-(2-(4-(4-cyano-1-methyl-1H-[1,2,3]triazolo[4,5-c]pyridin-6-yl)-2-(trifluoromethyl)phenoxy)ethyl)azetidine-1-carboxylate (86 mg) was dissolved in DCM (2000 µl) and acetonitrile (500 µl). Trifluoroacetic acid (400 µl) was added and the reaction stirred for 30 minutes. Solvent was evaporated under reduced pressure and the resulting residue dissolved in a minimum volume of EtOAc. Ether was added dropwise until the solution clouded then the mixture was allowed to stand for 30 minutes and filtered. Solid was washed with ether and dried to afford the desired product 6-(4-(2-(azetidin-3-yl)ethoxy)-3-(trifluoromethyl)phenyl)-1-methyl-1H-[1,2,3]triazolo[4,5-c]pyridine-4-carbonitrile 2,2,2-trifluoroacetate (62% yield).

$^1$H NMR (CD3OD) δ: 8.60 (s, 1H), 8.47 (s, 1H), 8.45 (d, 1H), 7.35 (d, 1H), 4.45 (s, 3H), 4.26 (t, 2H), 4.15 (t, 2H), 3.97 (t, 2H), 3.20 (m, 1H), 2.23 (m, 2H). MS m/z 403.2 (M+H).

EXAMPLE 31

6-(4-(2-(1-(2-dimethylamino-2-oxoethyl)azetidin-3-yl)ethoxy)-3-(trifluoromethyl)phenyl)-1-methyl-1H-[1,2,3]triazolo[4,5-c]pyridine-4-carbonitrile Hydrochloride

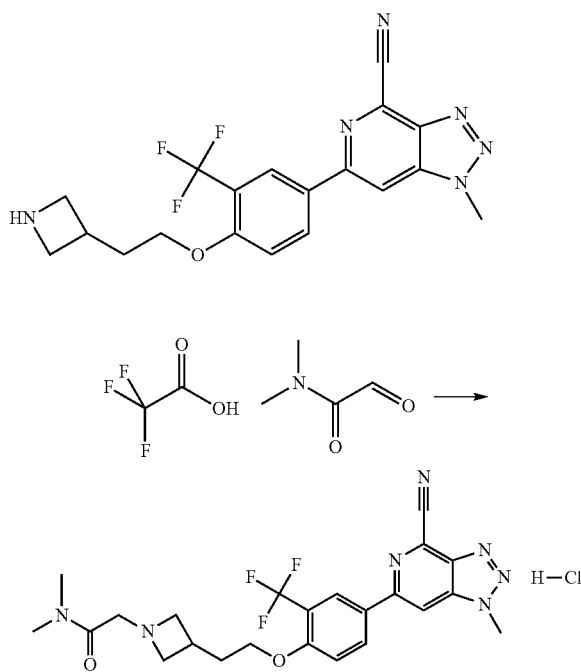

6-(4-(2-(Azetidin-3-yl)ethoxy)-3-(trifluoromethyl)phenyl)-1-methyl-1H-[1,2,3]triazolo[4,5-c]pyridine-4-carbonitrile 2,2,2-trifluoroacetate (0.959 mmol, 495 mg) N,N-dimethyl-2-oxoacetamide (9.59 mmol, 969 mg) and AcOH (9.59 mmol, 549 μL, 576 mg) were dissolved in MeOH (9586 μL) and sodium cyanoborohydride (9.59 mmol, 602 mg) added. The mixture was placed under nitrogen and heated to reflux for 20 hours. Solvent was evaporated under reduced pressure and the resulting residue purified by preparative HPLC (acidic) followed by SCX. Solvent was removed under reduced pressure and the residue lyophilised in a genevac with 0.5M HCl (aq) and then water to afford desired product 2-(3-(2-(4-(4-cyano-1-methyl-1H-[1,2,3]triazolo[4,5-c]pyridin-6-yl)-2-(trifluoromethyl)phenoxy)ethyl)azetidin-1-yl)-N,N-dimethylacetamide hydrochloride as a white solid. $^1$H NMR (CD3OD) δ: 8.60 (s, 1H), 8.46 (s, 1H), 8.44 (d, 1H), 7.36 (d, 1H), 4.45 (m, 1H), 4.44 (s, 3H), 4.42 (s, 1H), 4.35 (s, 1H), 4.27 (m, 4H), 3.97 (t, 1H), 3.25 (m, 1H), 2.97 (m, 6H), 2.23 2.32 (2 m, 2H). MS m/z 488 (M+H).

EXAMPLE 32

6-(4-(3-hydroxypropoxy)-3-(trifluoromethyl)phenyl)-1-methyl-1H-[1,2,3]triazolo[4,5-c]pyridine-4-carbonitrile

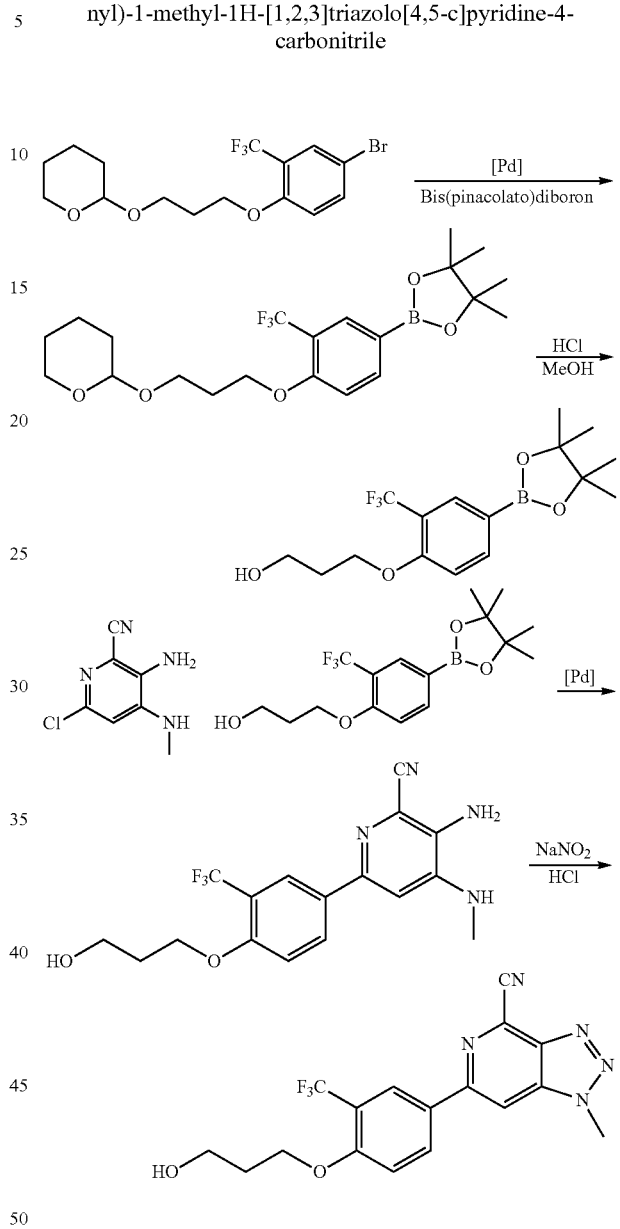

A: 4,4,5,5-tetramethyl-2-(4-(3-(tetrahydro-2H-pyran-2-yloxy)propoxy)-3-(trifluoromethyl)phenyl)-1,3,2-dioxaborolane 1,1'-bis(diphenylphosphino)ferrocenedichloropalladium (II) (5 g) was added to a mixture of 2-(3-(4-Bromo-2-(trifluoromethyl)-phenoxy)-propoxy)-tetrahydro-2H-pyran (53 g), bis(pinacolato)diboron (44.6 g) and potassium acetate (27.1 g) in dry dioxane (400 ml) under N$_2$. The mixture was heated to 100° C. for 3 hours then diluted with ethyl acetate and water and filtered through celite. The organic layer was separated, dried over magnesium sulphate and solvent removed under reduced pressure. The residue which was then columned on silica gel using DCM (100%) as eluant to give expected product (43 g). $^1$H NMR (CDCl3) δ: 8.00 (s, 1H), 7.91 (d, 1H), 6.99 (d, 1H), 4.57 (dd, 1H), 4.20 (t, 2H), 3.79-3.96 (m, 2H), 3.45-3.63 (m, 2H), 2.11 (quin, 2H), 1.46-1.88 (m, 6H), 1.33 (s, 12H).

B: 3-(4-(4,4,5,5-tetramethyl-1,3,2-dioxaborolan-2-yl)-2-(trifluoromethyl)phenoxy)-propan-1-ol Acetyl chloride (14.26 ml) was added to MeOH (150 ml) at 0° C. and stirred for 10 minutes. The above mixture was added to 4,4,5,5-tetramethyl-2-(4-(3-(tetrahydro-2H-pyran-2-yloxy)propoxy)-3-(trifluoromethyl)phenyl)-1,3,2-dioxaborolane (43 g) in MeOH (300 ml) and stirred at 50° C. for 1.5 hours. The solvent was removed under reduced pressure, DCM was added to the residue and it was basified with sodium bicarbonate, washed with water, and the DCM was removed under reduced pressure to give expected compound (35 g). $^1$H NMR (CDCl3) δ: 8.00 (s, 1H), 7.92 (d, 1H), 6.98 (d, 1H), 4.21 (t, 2H), 3.86 (t, 2H), 2.07 (quin, 2H), 1.34 (s, 12H).

C: 3-amino-6-(4-(3-hydroxypropoxy)-3-(trifluoromethyl)phenyl)-4-(methylamino)-picolinonitrile A mixture of 3-(4-(4,4,5,5-tetramethyl-1,3,2-dioxaborolan-2-yl)-2-(trifluoro-methyl)phenoxy)propan-1-ol (34 g), 3-amino-6-chloro-4-(methylamino)picolinonitrile (16.2 g), potassium phosphate (56.5 g), tricyclohexylphosphine (2.98 g), and tris(dibenzylideneacetone)dipalladium(0) (4.06 g) in dioxane (340 ml) and water (170 ml) under N$_2$ was heated to 100° C. for 2 hours then diluted with ethyl acetate and filtered through celite. The organic layer was separated, dried over magnesium sulphate and solvent removed under reduced pressure to give expected product clean enough for use in the next step (49.6 g). $^1$H NMR (CD3OD) δ: 8.06 (s, 1H), 8.01 (d, 1H), 7.23 (d, 1H), 6.86 (s, 1H), 4.23 (t, 2H), 3.78 (t, 2H), 2.98 (s, 3H), 2.04 (quin, 2H). MS m/z 367 (M+H).

D: 6-(4-(3-hydroxypropoxy)-3-(trifluoromethyl)phenyl)-1-methyl-1H-[1,2,3]triazolo[4,5-c]pyridine-4-carbonitrile A solution of sodium nitrite (13.07 g) in water (40 ml) was added to 3-amino-6-(4-(3-hydroxypropoxy)-3-(trifluoromethyl)phenyl)-4-(methylamino)picolinonitrile (49.6 g) in 2M hydrochloric acid (203 ml) and NMP (180 ml). The mixture was stirred at room temperature for 2 hours then diluted with ethyl acetate (50 mml), and the mixture washed with water (300 ml+100 ml×4), the organic layer was dried over magnesium sulphate, solvent removed under reduced pressure. The residue was then columned on silica gel using DCM then DCM-MeOH (199:1) as eluant to give expected product (10.34 g). $^1$H NMR (CD3OD) δ: 8.55 (s, 1H), 8.39-8.45 (m, 2H), 7.35 (d, 1H), 4.45 (s, 3H), 4.30 (t, 2H), 3.80 (t, 2H), 2.06 (quin, 2H). MS m/z 378 (M+H).

EXAMPLE 33

6-(4-(3-aminopropoxy)-3-(trifluoromethyl)phenyl)-1-methyl-1H-[1,2,3]triazolo[4,5-c]pyridine-4-carbonitrile

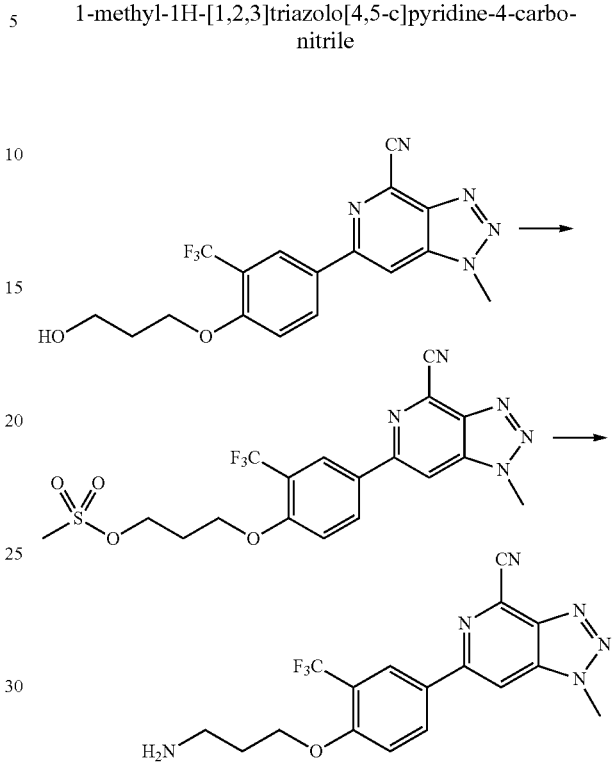

A: 3-(4-(4-cyano-1-methyl-1H-benzo[d][1,2,3]triazol-6-yl)-2-(trifluoromethyl)-phenoxy)propyl methanesulfonate Methanesulphonyl chloride (6.29 g) was added dropwise to a solution of 6-(4-(3-hydroxypropoxy)-3-(trifluoromethyl)phenyl)-1-methyl-1H-[1,2,3]triazolo[4,5-c]-pyridine-4-carbonitrile (10.34 g) and diisopropylethylamine (22.7 ml) in DCM (300 ml) at 0° C. The mixture was stirred at room temperature for 2 hours. The DCM was removed under reduced pressure, MeOH and water were added to the residue and the solid was collected by filtration to give the expected product (11.56 g). $^1$H NMR (DMSO) δ: 8.96 (s, 1H), 8.49 (d, 1H), 8.46 (s, 1H), 7.51 (d, 1H), 4.46 (s, 3H), 4.39 (t, 2H), 4.34 (t, 2H), 3.18 (s, 3H), 2.21 (quin, 2H).

B: 6-(4-(3-aminopropoxy)-3-(trifluoromethyl)phenyl)-1-methyl-1H-[1,2,3]triazolo[4,5-c]pyridine-4-carbonitrile A mixture of 3-(4-(4-cyano-1-methyl-1H-benzo[d][1,2,3]triazol-6-yl)-2-(trifluoromethyl)phenoxy)propyl methanesulfonate (367 mg) and ammonia in methanol (7M, 10 ml) was heated at 100° C. under microwave conditions for 20 minutes. After removal of solvent under vacuum, the expected product 6-(4-(3-aminopropoxy)-3-(trifluoromethyl)phenyl)-1-methyl-1H-[1,2,3]triazolo[4,5-c]pyridine-4-carbonitrile was obtained as methanesulphonic acid salt. $^1$H NMR (CD3OD) δ: 8.60 (s, 1H), 8.41-8.48 (m, 2H), 7.38

(d, 1H), 4.45 (s, 3H), 4.34 (t, 2H), 3.20 (t, 2H), 2.69 (s, 3H), 2.24 (quin, 2H). MS m/z 473 (M+H).

EXAMPLE 34

N-(3-(4-(4-cyano-1-methyl-1H-[1,2,3]triazolo[4,5-c]pyridin-6-yl)-2-(trifluoromethyl)-phenoxy)propyl)acetamide

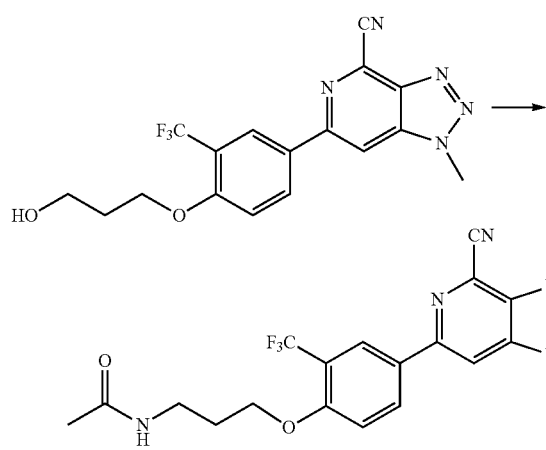

Acetyl chloride (18.3 mg) was added to a mixture of 6-(4-(3-aminopropoxy)-3-(trifluoromethyl)phenyl)-1-methyl-1H-[1,2,3]triazolo[4,5-c]pyridine-4-carbonitrile (100 mg) and triethylamine (294 µl) in DCM (2 ml). The mixture was stirred at room temperature for 2 hours then diluted with water, the organic layer was separated, dried over magnesium sulphate, and solvent was removed under reduced pressure. The residue was purified by HPLC to give the expected product (4.4 mg). $^1$H NMR (CD3OD) δ: 8.56 (s, 1H), 8.38-8.45 (m, 2H), 7.33 (d, 1H), 4.45 (s, 3H), 4.23 (t, 2H), 3.40 (t, 2H), 2.05 (quin, 2H), 1.95 (s, 3H). MS m/z 419 (M+H).

EXAMPLE 35

6-(4-(3-(dimethylamino)propoxy)-3-(trifluoromethyl)phenyl)-1-methyl-1H-[1,2,3]triazolo[4,5-c]pyridine-4-carbonitrile

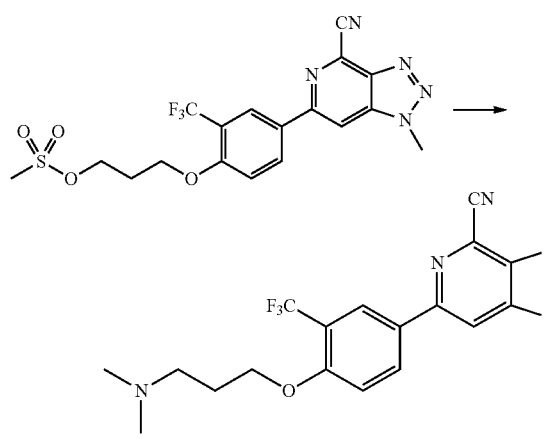

A mixture of 3-(4-(4-cyano-1-methyl-1H-benzo[d][1,2,3]triazol-6-yl)-2-(trifluoro-methyl)phenoxy)propyl methanesulfonate (20 mg), diisopropylethylamine (73 µl) and dimethylamine in THF (2M, 1 ml) was heated at 100° C. under microwave conditions for 20 minutes. The mixture was purified by HPLC to give the expected product (6.3 mg).
$^1$H NMR (CD3OD) δ: 8.57 (s, 1H), 8.38-8.45 (m, 2H), 7.33 (d, 1H), 4.45 (s, 3H), 4.25 (t, 2H), 3.75 (t, 2H), 2.42 (s, 6H), 2.10 (quin, 2H). MS m/z 405 (M+H).

EXAMPLE 36a 6-(4-(3-(4-hydroxy-4-methylpiperidin-1-yl)propoxy)-3-(trifluoromethyl)phenyl)-1-methyl-1H-[1,2,3]triazolo[4,5-d]pyridine-4-carbonitrile

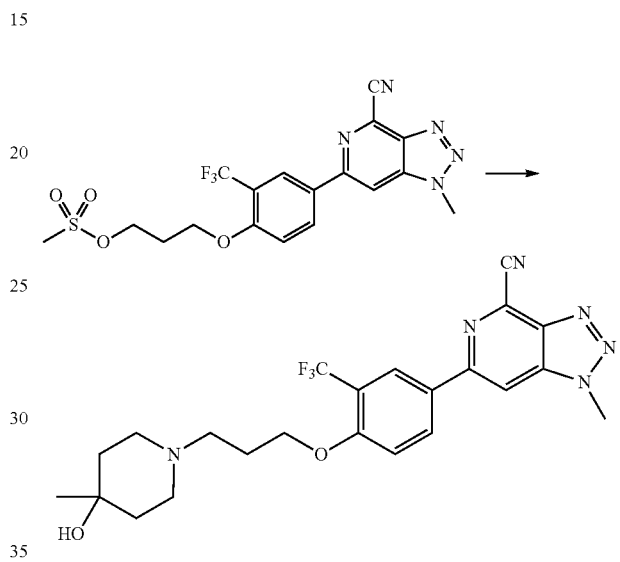

A mixture of 3-(4-(4-cyano-1-methyl-1H-benzo[d][1,2,3]triazol-6-yl)-2-(trifluoromethyl)phenoxy)propyl methanesulfonate (100 mg) and 4-methylpiperidin-4-ol hydrochloride (166 mg) in NMP (2 ml) was heated at 100° C. under microwave conditions for 30 minutes. The mixture was purified by HPLC to give the expected product (9.4 mg). $^1$H NMR (CD3OD) δ: 8.55 (s, 1H), 8.35-8.42 (m, 2H), 7.32 (d, 1H), 4.44 (s, 3H), 4.25 (t, 2H), 2.76-2.89 (m, 4H), 2.63-2.75 (m, 2H), 2.13 (quin, 2H), 1.64-1.80 (m, 4H), 1.24 (s, 3H). MS m/z 475 (M+H).

The procedure described in Example 36a was further applied, using the appropriate amines, to prepare the following compounds:

36b: 1-(3-(4-(4-cyano-1-methyl-1H-[1,2,3]triazolo[4,5-d]pyridin-6-yl)-2-(trifluoro-methyl)phenoxy)propyl)piperidine-4-carboxamide

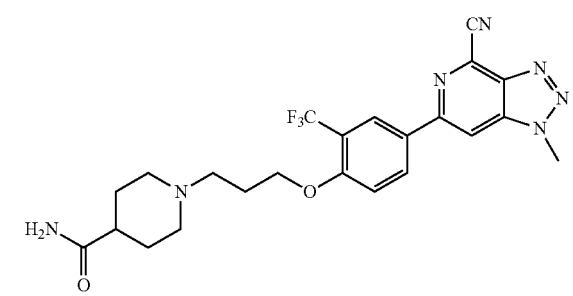 [SMILES: Cn1nnc2c(C#N)nc(-c3ccc(OCCCN4CCC(C(N)=O)CC4)c(C(F)(F)F)c3)cc21]

¹H NMR (CD3OD) δ: 8.59 (s, 1H), 8.41-8.48 (m, 2H), 7.36 (d, 1H), 4.45 (s, 3H), 4.26 (t, 2H), 3.04 (d, 2H), 2.62 (t, 2H), 2.20-2.29 (m, 1H), 2.04-2.13 (m, 4H), 1.70-1.88 (m, 4H). MS m/z 488 (M+H).

36c: 1-methyl-6-(3-(trifluoromethyl)-4-(3-(4-(4-(trifluoromethyl)pyridin-2-yl)piperazin-1-yl)propoxy)phenyl)-1H-[1,2,3]triazolo[4,5-c]pyridine-4-carbonitrile

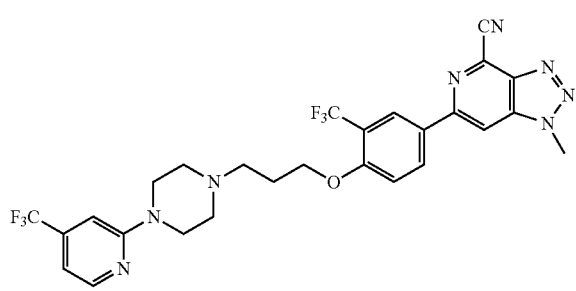 [SMILES: Cn1nnc2c(C#N)nc(-c3ccc(OCCCN4CCN(c5cc(C(F)(F)F)ccn5)CC4)c(C(F)(F)F)c3)cc21]

¹H NMR (CD3OD) δ: 8.59 (s, 1H), 8.41-8.48 (m, 2H), 8.29 (d, 1H), 7.38 (d, 1H), 7.01 (s, 1H), 6.84 (d, 1H), 4.45 (s, 3H), 4.30 (t, 2H), 3.62-3.69 (m, 4H), 2.63-2.71 (m, 6H), 2.12 (quin, 2H). MS m/z 591 (M+H).

36d: 1-methyl-6-(4-(3-(4-(3-methylpyridin-2-yl)piperazin-1-yl)propoxy)-3-(trifluoromethyl)phenyl)-1H-[1,2,3]triazolo[4,5-c]pyridine-4-carbonitrile

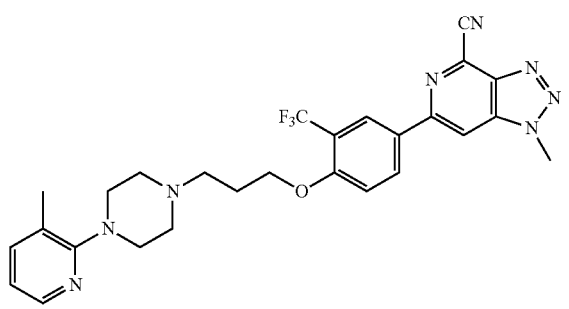 [SMILES: Cc1cccnc1N1CCN(CCCOc2ccc(-c3cc4c(nnn4C)c(C#N)n3)cc2C(F)(F)F)CC1]

¹H NMR (CD3OD) δ: 8.60 (s, 1H), 8.41-8.48 (m, 2H), 8.06 (d, 1H), 7.53 (d, 1H), 7.39 (d, 1H), 6.94 (t, 1H), 4.46 (s, 3H), 4.30 (t, 2H), 3.13-3.21 (m, 4H), 2.63-2.75 (m, 6H), 2.12 (quin, 2H). MS m/z 537 (M+H).

36e: 6-(4-(3-(4-(5-chloropyridin-2-yl)piperazin-1-yl)propoxy)-3-(trifluoromethyl)phenyl)-1-methyl-1H-[1,2,3]triazolo[4,5-c]pyridine-4-carbonitrile

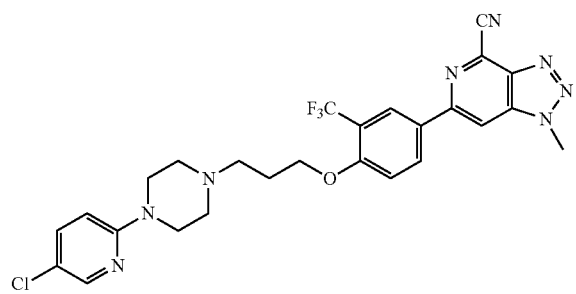 [SMILES: Cn1nnc2c(C#N)nc(-c3ccc(OCCCN4CCN(c5ccc(Cl)cn5)CC4)c(C(F)(F)F)c3)cc21]

¹H NMR (CD3OD) δ: 8.59 (s, 1H), 8.41-8.48 (m, 2H), 8.05 (s, 1H), 7.52 (d, 1H), 7.38 (d, 1H), 6.81 (d, 1H), 4.45 (s, 3H), 4.30 (t, 2H), 3.52-3.59 (m, 4H), 2.61-2.72 (m, 6H), 2.11 (quin, 2H). MS m/z 557 (M+H).

36f: 6-(4-(3-(4-(3-chloropyridin-2-yl)piperazin-1-yl)propoxy)-3-(trifluoromethyl)phenyl)-1-methyl-1H-[1,2,3]triazolo[4,5-c]pyridine-4-carbonitrile

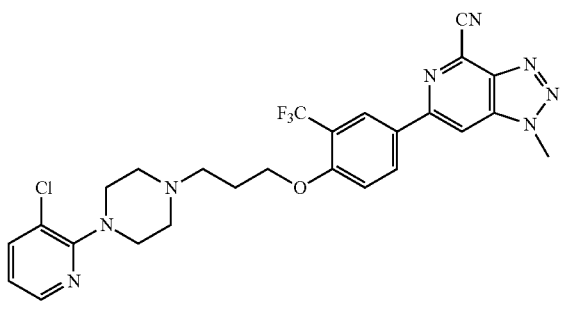 [SMILES: Cn1nnc2c(C#N)nc(-c3ccc(OCCCN4CCN(c5ncccc5Cl)CC4)c(C(F)(F)F)c3)cc21]

¹H NMR (CD3OD) δ: 8.60 (s, 1H), 8.41-8.48 (m, 2H), 8.16 (d, 1H), 7.72 (d, 1H), 7.38 (d, 1H), 6.92-6.97 (m, 1H), 4.46 (s, 3H), 4.30 (t, 2H), 3.38-3.43 (m, 4H), 2.66-2.72 (m, 6H), 2.12 (quin, 2H). MS m/z 557 (M+H).

36g: 2-(4-(3-(4-(4-cyano-1-methyl-1H-[1,2,3]triazolo[4,5-c]pyridin-6-yl)-2-(trifluoromethyl)phenoxy)propyl)piperazin-1-yl)-N,N-dimethylacetamide

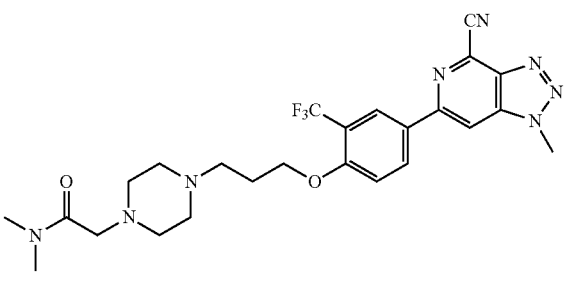 [SMILES: CN(C)C(=O)CN1CCN(CCCOc2ccc(-c3cc4c(nnn4C)c(C#N)n3)cc2C(F)(F)F)CC1]

¹H NMR (CD3OD) δ: 8.58 (s, 1H), 8.40-8.46 (m, 2H), 7.34 (d, 1H), 4.45 (s, 3H), 4.25 (t, 2H), 3.24 (s, 2H), 3.09 (s, 3H), 2.93 (s, 3H), 2.39-2.80 (m, 10H), 2.06 (quin, 2H). MS m/z 531 (M+H).

36h: 1-methyl-6-(4-(3-(4-S,S-dioxothiomorpholin-1-yl)propoxy)-3-(trifluoromethyl)-phenyl)-1H-[1,2,3]triazolo[4,5-c]pyridine-4-carbonitrile

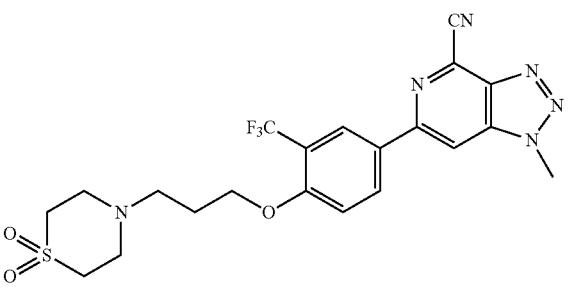 [SMILES: Cn1nnc2c(C#N)nc(-c3ccc(OCCCN4CCS(=O)(=O)CC4)c(C(F)(F)F)c3)cc21]

¹H NMR (DMSO) δ: 8.95 (s, 1H), 8.48 (d, 1H), 8.44 (s, 1H), 7.49 (d, 1H), 4.42 (s, 3H), 4.28 (t, 2H), 3.05-3.16 (m, 4H), 2.89-2.95 (m, 4H), 2.66 (t, 2H), 1.94 (quin, 2H). MS m/z 495 (M+H).

36i: 1-methyl-6-(4-(3-(4-(methylsulfonyl)piperazin-1-yl)propoxy)-3-(trifluoromethyl)-phenyl)-1H-[1,2,3]triazolo[4,5-c]pyridine-4-carbonitrile

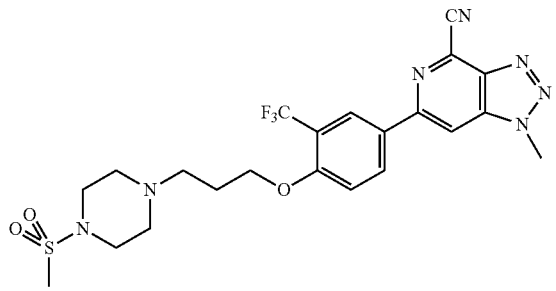 [SMILES: Cn1nnc2c(C#N)nc(-c3ccc(OCCCN4CCN(S(C)(=O)=O)CC4)c(C(F)(F)F)c3)cc21]

¹H NMR (DMSO) δ: 8.97 (s, 1H), 8.49 (d, 1H), 8.45 (s, 1H), 7.49 (d, 1H), 4.46 (s, 3H), 4.27 (t, 2H), 3.27-3.40 (m, 4H), 3.02-3.15 (m, 4H), 2.87 (s, 3H), 2.51-2.59 (m, 2H), 1.95 (quin, 2H). MS m/z 524 (M+H).

36j: 1-methyl-6-(3-(trifluoromethyl)-4-(3-(3-(trifluoromethyl)piperazin-1-yl)propoxy)-phenyl)-1H-[1,2,3]triazolo[4,5-c]pyridine-4-carbonitrile

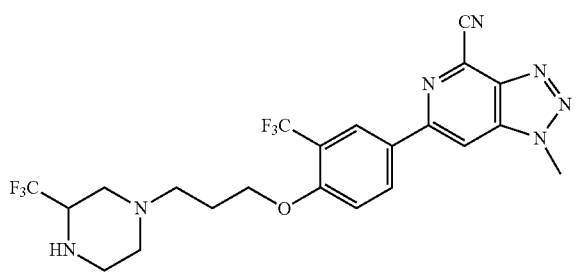 [SMILES: Cn1nnc2c(C#N)nc(-c3ccc(OCCCN4CCNC(C(F)(F)F)C4)c(C(F)(F)F)c3)cc21]

¹H NMR (CD3OD) δ: 8.59 (s, 1H), 8.42-8.48 (m, 2H), 7.37 (d, 1H), 4.47 (s, 3H), 4.28 (t, 2H), 3.38-3.44 (m, 1H), 3.00-3.07 (m, 2H), 2.81-2.92 (m, 2H), 2.68 (t, 2H), 2.02-2.19 (m, 4H). MS m/z 514 (M+H).

36k: 2-((3-(4-(4-cyano-1-methyl-1H-[1,2,3]triazolo[4,5-c]pyridin-6-yl)-2-(trifluoro-methyl)phenoxy)propyl)(methyl)amino)acetamide

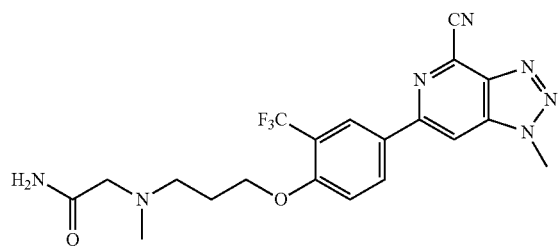 [SMILES: CN(CCCOc1ccc(-c2cc3c(nnn3C)c(C#N)n2)cc1C(F)(F)F)CC(N)=O]

¹H NMR (DMSO) δ: 8.98 (s, 1H), 8.49 (d, 1H), 8.45 (s, 1H), 7.50 (d, 1H), 4.46 (s, 3H), 4.29 (t, 2H), 2.88 (s, 2H), 2.51-2.60 (m, 2H), 2.23 (s, 3H), 1.93 (quin, 2H). MS m/z 448 (M+H).

36l: 2-(3-(4-(4-cyano-1-methyl-1H-[1,2,3]triazolo[4,5-c]pyridin-6-yl)-2-(trifluoro-methyl)phenoxy)propylamino)acetamide

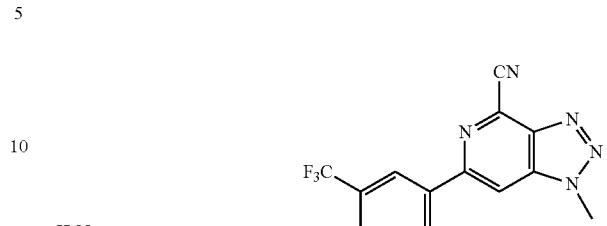

¹H NMR (CD3OD) δ: 8.57 (s, 1H), 8.40-8.48 (m, 2H), 7.37 (d, 1H), 4.45 (s, 3H), 4.29 (t, 2H), 3.27 (s, 2H), 2.84 (t, 2H), 2.06 (quin, 2H). MS m/z 434 (M+H).

36m: 2-(3-(4-(4-cyano-1-methyl-1H-[1,2,3]triazolo[4,5-c]pyridin-6-yl)-2-(trifluoromethyl)phenoxy)propylamino)-N-methylacetamide

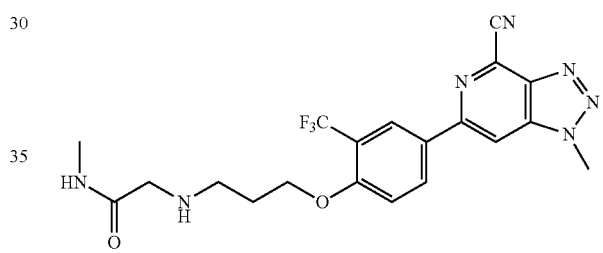

¹H NMR (CD3OD) δ: 8.57 (s, 1H), 8.40-8.48 (m, 2H), 7.37 (d, 1H), 4.45 (s, 3H), 4.29 (t, 2H), 3.25 (s, 2H), 2.81 (t, 2H), 2.74 (s, 3H), 2.05 (quin, 2H). MS m/z 448 (M+H).

36n: 2-((3-(4-(4-cyano-1-methyl-1H-[1,2,3]triazolo[4,5-c]pyridin-6-yl)-2-(trifluoromethyl)phenoxy)propyl)(methyl)amino)-N-methylacetamide

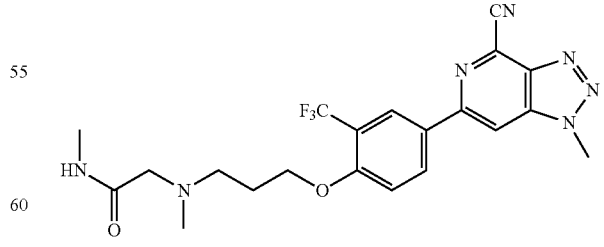

¹H NMR (CD3OD) δ: 8.59 (s, 1H), 8.41-8.49 (m, 2H), 7.38 (d, 1H), 4.45 (s, 3H), 4.29 (t, 2H), 3.04 (s, 3H), 2.62-2.73 (m, 5H), 2.33 (s, 3H), 2.04 (quin, 2H). MS m/z 462 (M+H).

36o: 2-(3-(4-(4-cyano-1-methyl-1H-[1,2,3]triazolo[4,5-c]pyridin-6-yl)-2-(trifluoromethyl)phenoxy)propylamino)-N,N-dimethylacetamide

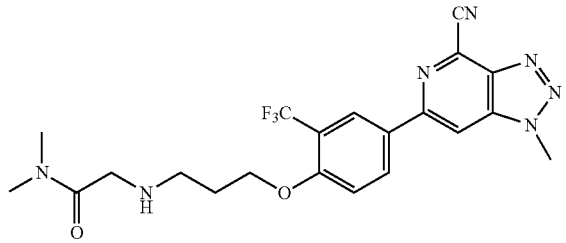 [SMILES: CN(C)C(=O)CNCCCOc1ccc(-c2cc3c(nnn3C)c(C#N)n2)cc1C(F)(F)F]

$^1$H NMR (CD3OD) δ: 8.56 (s, 1H), 8.39-8.46 (m, 2H), 7.37 (d, 1H), 4.45 (s, 3H), 4.29 (t, 2H), 3.52 (s, 2H), 3.01 (s, 3H), 2.96 (s, 3H), 2.88 (t, 2H), 2.09 (quin, 2H). MS m/z 462 (M+H).

36p: 1-methyl-6-(4-(3-(5-oxo-1,4-diazepan-1-yl)propoxy)-3-(trifluoromethyl)phenyl)-1H-[1,2,3]triazolo[4,5-c]pyridine-4-carbonitrile

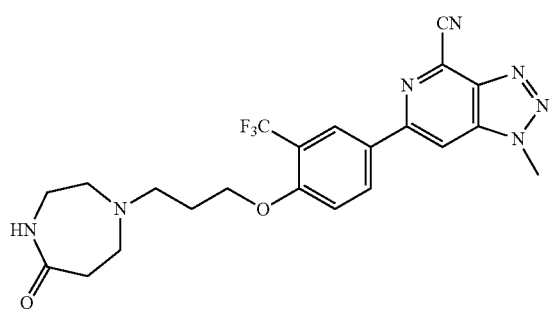 [SMILES: Cn1nnc2c(C#N)nc(-c3ccc(OCCCN4CCNC(=O)CC4)c(C(F)(F)F)c3)cc21]

$^1$H NMR (CD3OD) δ: 8.56 (s, 1H), 8.39-8.47 (m, 2H), 7.37 (d, 1H), 4.45 (s, 3H), 4.27 (t, 2H), 3.32-3.39 (m, 1H), 2.56-2.78 (m, 9H), 2.07 (quin, 2H). MS m/z 474 (M+H).

36q: 6-(4-(3-(diethylamino)propoxy)-3-(trifluoromethyl)phenyl)-1-methyl-1H-[1,2,3]triazolo[4,5-c]pyridine-4-carbonitrile

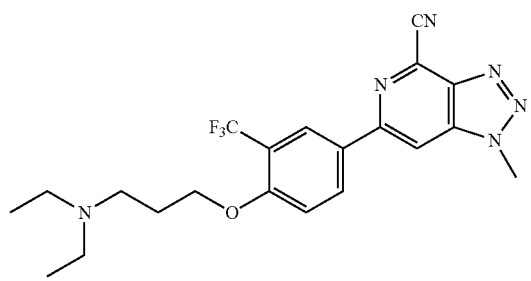 [SMILES: CCN(CC)CCCOc1ccc(-c2cc3c(nnn3C)c(C#N)n2)cc1C(F)(F)F]

$^1$H NMR (CD3OD) δ: 8.58 (s, 1H), 8.40-8.48 (m, 2H), 7.35 (d, 1H), 4.45 (s, 3H), 4.25 (t, 2H), 2.80 (t, 2H), 2.66 (q, 4H), 2.05 (quin, 2H), 1.11 (t, 6H). MS m/z 433 (M+H).

36r: 1-methyl-6-(4-(3-(4-(6-methylpyridin-2-yl)piperazin-1-yl)propoxy)-3-(trifluoromethyl)phenyl)-1H-[1,2,3]triazolo[4,5-c]pyridine-4-carbonitrile hydrochloride

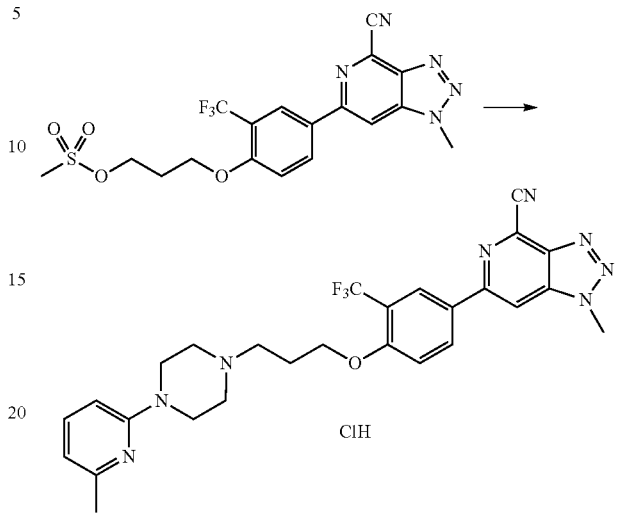

$^1$H NMR (CD3OD) δ: 8.62 (s, 1H), 8.43-8.51 (m, 2H), 8.07 (t, 1H), 7.42 (d, 1H), 7.29 (d, 1H), 7.03 (d, 1H), 4.46 (s, 3H), 4.39 (t, 2H), 3.32-4.05 (m, 10H), 2.64 (s, 3H), 2.45 (quin, 2H). MS m/z 537 (M+H).

36s: 1-methyl-6-(4-(3-(3-oxopiperazin-1-yl)propoxy)-3-(trifluoromethyl)phenyl)-1H-[1,2,3]triazolo[4,5-c]pyridine-4-carbonitrile hydrochloride

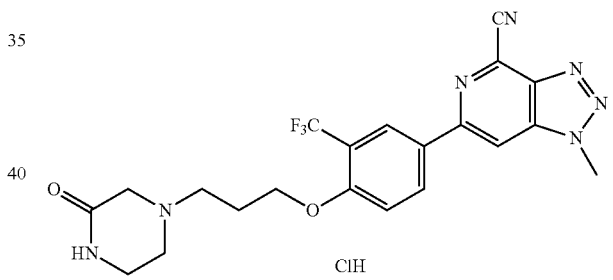

$^1$H NMR (CD3OD) δ: 8.62 (s, 1H), 8.43-8.51 (m, 2H), 7.40 (d, 1H), 4.46 (s, 3H), 4.36 (t, 2H), 4.00 (brs, 2H), 3.43-3.77 (m, 6H), 2.38 (quin, 2H). MS m/z 460 (M+H).

36t: 6-(4-(3-(4-(2-hydroxyethyl)piperazin-1-yl)propoxy)-3-(trifluoromethyl)phenyl)-1-methyl-1H-[1,2,3]triazolo[4,5-c]pyridine-4-carbonitrile dihydrochloride

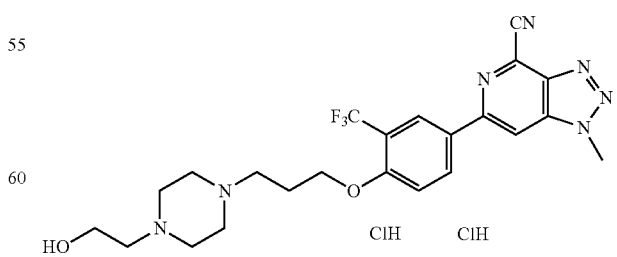

$^1$H NMR (CD3OD) δ: 8.58 (s, 1H), 8.41-8.48 (m, 2H), 7.39 (d, 1H), 4.46 (s, 3H), 4.38 (t, 2H), 3.37-4.00 (m, 14H), 2.39 (quin, 2H). MS m/z 490 (M+H).

36u: 6-(4-(3-(4-(2-hydroxy-2-methylpropyl)piperazin-1-yl)propoxy)-3-(trifluoromethyl)phenyl)-1-methyl-1H-[1,2,3]triazolo[4,5-c]pyridine-4-carbonitrile dihydrochloride

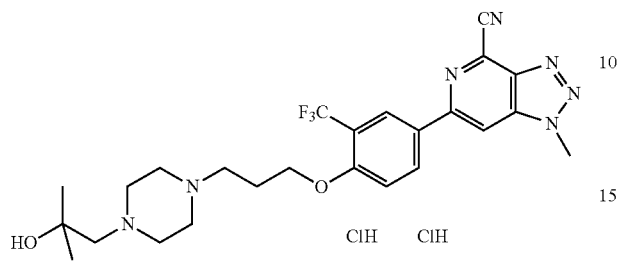

¹H NMR (CD3OD) δ: 8.61 (s, 1H), 8.43-8.49 (m, 2H), 7.40 (d, 1H), 4.46 (s, 3H), 4.38 (t, 2H), 3.45-4.10 (m, 10H), 3.30 (s, 2H), 2.40 (quin, 2H), 1.38 (s, 6H). MS m/z 518 (M+H).

36v: 2-(4-(3-(4-(4-cyano-1-methyl-1H-[1,2,3]triazolo[4,5-c]pyridin-6-yl)-2-(trifluoromethyl)phenoxy)propyl)piperazin-1-yl)-N-methylacetamide dihydrochloride

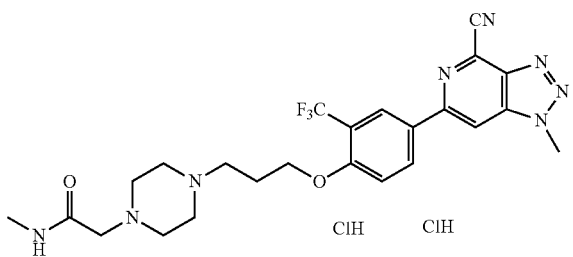 [SMILES: CNC(=O)CN1CCN(CCCOc2ccc(-c3cc4c(nnn4C)c(C#N)n3)cc2C(F)(F)F)CC1 ; Cl ; Cl]

¹H NMR (CD3OD) δ: 8.60 (s, 1H), 8.41-8.48 (m, 2H), 7.39 (d, 1H), 4.46 (s, 3H), 4.38 (t, 2H), 3.41-3.96 (m, 12H), 2.81 (s, 3H), 2.41 (quin, 2H). MS m/z 517 (M+H).

36w: 1-methyl-6-(4-(3-(4-(pyridin-2-yl)piperazin-1-yl)propoxy)-3-(trifluoromethyl)phenyl)-1H-[1,2,3]triazolo[4,5-c]pyridine-4-carbonitrile hydrochloride

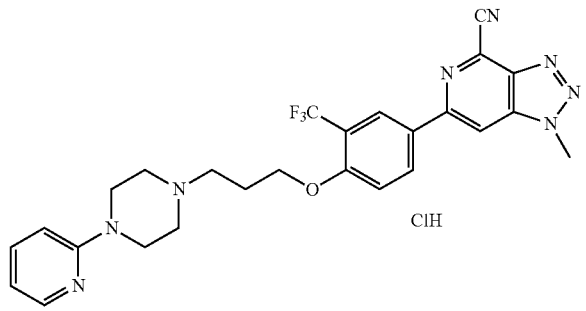 [SMILES: Cn1nnc2c(C#N)nc(-c3ccc(OCCCN4CCN(c5ccccn5)CC4)c(C(F)(F)F)c3)cc21 ; Cl]

¹H NMR (CD3OD) δ: 8.62 (s, 1H), 8.47-8.52 (m, 2H), 8.15 (d, 1H), 7.91 (t, 1H), 7.41 (d, 1H), 7.23 (d, 1H), 6.99 (t, 1H), 3.49-4.67 (m, 15H), 2.41 (quin, 2H). MS m/z 523 (M+H).

36x: 2-((3-(4-(4-cyano-1-methyl-1H-[1,2,3]triazolo[4,5-c]pyridin-6-yl)-2-(trifluoro-methyl)phenoxy)propyl)(methyl)amino)-N,N-dimethylacetamide hydrochloride

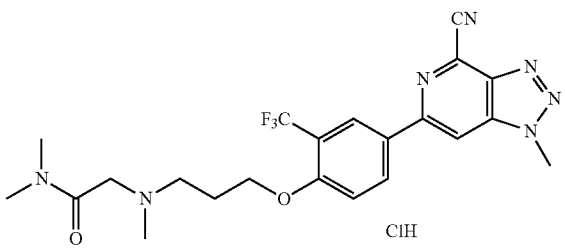 [SMILES: CN(CCCOc1ccc(-c2cc3c(nnn3C)c(C#N)n2)cc1C(F)(F)F)CC(=O)N(C)C ; Cl]

¹H NMR (CD3OD) δ: 8.58 (s, 1H), 8.42-8.48 (m, 2H), 7.39 (d, 1H), 4.45 (s, 3H), 4.26-4.40 (m, 4H), 3.39-3.56 (m, 2H), 2.99-3.08 (m, 9H), 2.39 (quin, 2H). MS m/z 476 (M+H).

EXAMPLE 37a methyl-6-(4-(2-(4-(6-methylpyridin-2-yl)piperazin-1-yl)ethoxy)-3-(trifluoromethyl)phenyl)-1H-[1,2,3]triazolo[4,5-c]pyridine-4-carbonitrile

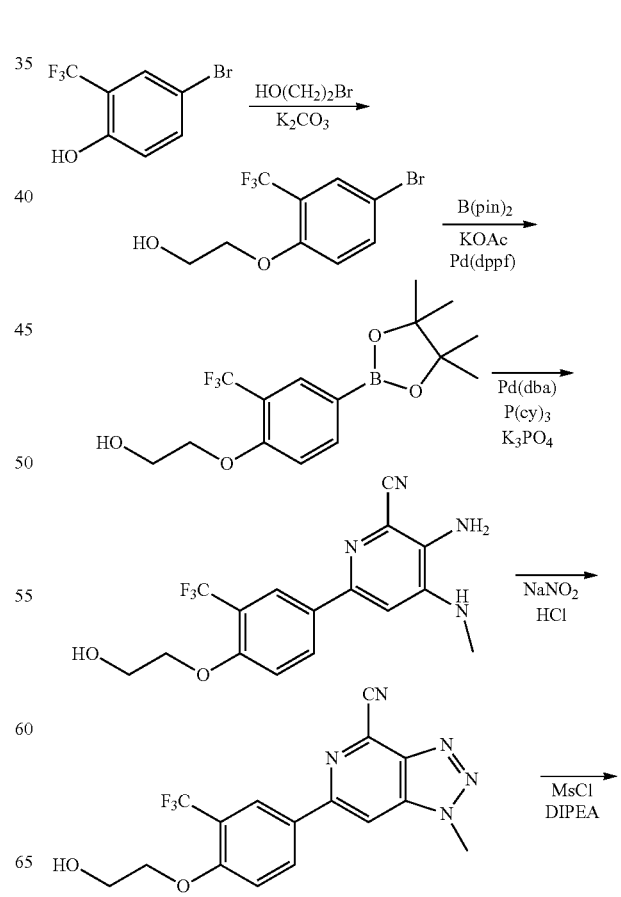

-continued

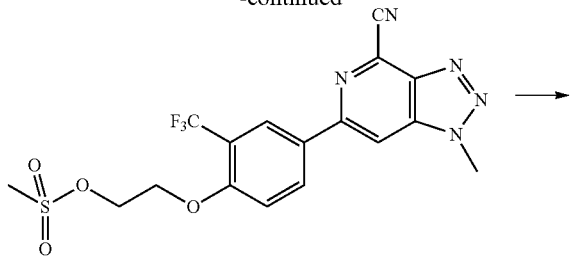

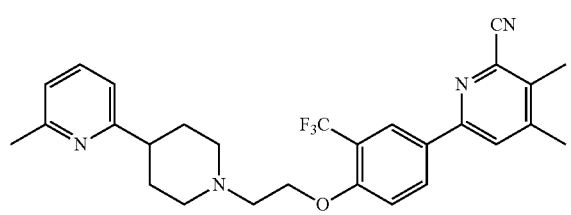

A: 2-(4-bromo-2-(trifluoromethyl)phenoxy)ethanol

2-Bromoethanol (10.37 g) was added to a mixture of 4-bromo-2-(trifluoro-methyl)phenol (20 g) and potassium carbonate (22.94 g) in Acetonitrile (150 ml). The above reaction mixture was refluxed overnight, then diluted with ethyl acetate (500 ml), water (300 ml) the 0.5M sodium hydroxide (300 ml). Organic layer was separated and dried over magnesium sulphate, solvent removed under reduced pressure to give white solid (19 g), NMR consistent with product. $^1$H NMR (CDCl$_3$) δ: 7.69 (d, 1H), 7.58 (dd, 1H), 6.91 (d, 1H), 4.15 (t, 2H), 3.97 (t, 2H).

B: 2-(4-(4,4,5,5-tetramethyl-1,3,2-dioxaborolan-2-yl)-2-(trifluoromethyl)phenoxy)ethanol 2-(4-bromo-2-(trifluoromethyl)phenoxy)ethanol (19 g), 4,4,4',4',5,5,5',5'-octamethyl-2,2'-bi(1,3,2-dioxaborolane) (16.93 g), potassium acetate (13.08 g), and 1,1'-bis(diphenylphosphino)ferrocenedichlropalladium(II) (2.412 g) were dissolved in dry Dioxane (150 ml) and stirred under nitrogen at 100° C. for 3 hrs. Reaction mixture was diluted with ethyl acetate and filtered through dicelite. Filtrate was washed with water, organics extracted and concentrated in vacuo to give crude 2-(4-(4,4,5,5-tetramethyl-1,3,2-dioxaborolan-2-yl)-2-(trifluoromethyl)phenoxy)ethanol (35 g). Residue was purified by flash chromatography (340 g, DCM, 1-2% MeOH: DCM) to give 2-(4-(4,4,5,5-tetramethyl-1,3,2-dioxaborolan-2-yl)-2-(trifluoromethyl)phenoxy)ethanol (14.9 g). $^1$H NMR (CDCl3) δ: 8.01 (s, 1H), 7.94 (d, 1H), 6.99 (d, 1H), 4.18 (t, 2H), 3.98 (t, 3.98), 1.34 (s, 12H).

C: 3-amino-6-(4-(2-hydroxyethoxy)-3-(trifluoromethyl)phenyl)-4-(methylamino)-picolinonitrile 2-(4-(4,4,5,5-Tetramethyl-1,3,2-dioxaborolan-2-yl)-2-(trifluoromethyl)phenoxy)ethanol (7.1 g), 3-amino-6-chloro-4-(methylamino)picolinonitrile (21.38 mmol, 3.90 g), potassium phosphate, tribasic (13.61 g), tricyclohexylphosohine (0.719 g), and tris(dibenzylideneacetone)dipalladium(0) (0.979 g) were dissolved in Dioxane (100 ml) and Water (40.0 ml) and stirred under nitrogen at 100° C. for 3 hrs. The mixture was diluted with ethyl acetate and filtered through celite. Filtrate was washed with water (300 ml), organic layer extracted and concentrated in vacuo to give crude 3-amino-6-(4-(2-hydroxyethoxy)-3-(trifluoromethyl)phenyl)-4-(methylamino)picolinonitrile (11 g). $^1$H NMR (MeOH) δ: 8.07 (s, 1H), 8.00 (d, 1H), 7.70 (m, 1H), 7.42 (m, 1H), 7.25 (m, 1H), 4.20 (t, 2.5), 3.93 (t, 2.5), 3.66 (s, 1.5), 2.98 (s, 3.5). MS m/z 353 (M+H).

D: 6-(4-(2-hydroxyethoxy)-3-(trifluoromethyl)phenyl)-1-methyl-1H-[1,2,3]triazolo[4,5-c]pyridine-4-carbonitrile 3-Amino-6-(4-(2-hydroxyethoxy)-3-(trifluoromethyl)phenyl)-4-(methylamino)-picolinonitrile (11 g) was dissolved in dioxane (20 ml), and water (20 ml). 1M HCl (16.39 ml) was added. Sodium nitrite (2.111 g) in water (2 mL) was added and reaction mixture was stirred at room temperature for 2 hrs. Product crashed out and was filtered, washed with water, ether and dried in oven to give 6-(4-(2-hydroxyethoxy)-3-(trifluoromethyl)phenyl)-1-methyl-1H-[1,2,3]triazolo[4,5-c]pyridine-4-carbonitrile (5.7 g) as a pale brown solid. $^1$H NMR (MeOH) δ: 8.55 (s, 1H), 8.43 (m, 2H), 7.36 (d, 1H), 4.45 (s, 3H), 4.25 (t, 2H), 3.95 (t, 2H). MS m/z 364 (M+H).

E: 2-(4-(4-cyano-1-methyl-1H-[1,2,3]triazolo[4,5-c]pyridin-6-yl)-2-(trifluoromethyl)phenoxy)ethyl methanesulfonate Methanesulfonyl chloride (3.95 ml, 4.53 g) was added dropwise at 0° C. to a solution of 6-(4-(2-hydroxyethoxy)-3-(trifluoromethyl)phenyl)-1-methyl-1H-[1,2,3]triazolo[4,5-c]pyridine-4-carbonitrile (5.7 g) and diisopropylethylamine (17.28 ml, 12.79 g). The mixture was stirred at room temperature for 1 hour. 10 ml methanol added and stirred for 5 minutes, followed by cold water (20 ml). Product precipitated, collected by filtration and washed with diethyl ether. Sample dried in the oven to give 2-(4-(4-cyano-1-methyl-1H-[1,2,3]triazolo[4,5-c]pyridin-6-yl)-2-(trifluoromethyl)-phenoxy)ethyl methanesulfonate (6.3 g). $^1$H NMR (DMSO) δ: 8.99 (s, 8.99), 8.48 (m, 2H), 7.53 (d, 1H), 4.60 (m, 4H), 4.46 (s, 3H), 3.24 (s, 3H). MS m/z 442 (M+H).

F: methyl-6-(4-(2-(4-(6-methylpyridin-2-yl)piperazin-1-yl)ethoxy)-3-(trifluoromethyl)phenyl)-1H-[1,2,3]triazolo[4,5-c]pyridine-4-carbonitrile A mixture of 2-(4-(4-cyano-1-methyl-1H-[1,2,3]triazolo[4,5-c]pyridin-6-yl)-2-(trifluoromethyl)phenoxy)ethyl methanesulfonate (0.15 g) and 1-(6-methylpyridin-2-yl)piperazine (0.361 g) in N-methylpyrollidine (2 ml) was heated at 150° C. under microwave condition for 30 minutes. Solvent removed under vacuum and residue dissolved in methanol (1 ml) and purified by basic prep HPLC to give methyl-6-(4-(2-(4-(6-methylpyridin-2-yl)piperazin-1-yl)ethoxy)-3-(trifluoromethyl)phenyl)-1H-[1,2,3]triazolo[4,5-c]pyridine-4-carbonitrile (0.0132 g). $^1$H NMR (MeOD) δ: 8.45 (m, 3H), 7.43 (m, 2H), 6.57 (m, 2H), 4.46 (s, 3H), 4.41 (m, 2H), 3.35 (m, 3.35), 2.97 (m, 2H), 2.78 (m, 4H), 2.35 (s, 3H). MS m/z 523.2 (M+H).

The procedure described in Example 37a was further applied, using the appropriate reagent, to prepare the following compounds:

37b: 6-(4-(2-(4-(5-chloropyridin-2-yl)piperazin-1-yl)ethoxy)-3-(trifluoromethyl)phenyl)-1-methyl-1H-[1,2,3]triazolo[4,5-c]pyridine-4-carbonitrile

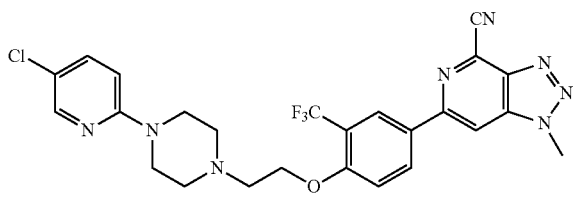 [SMILES: Cn1nnc2c(C#N)nc(-c3ccc(OCCN4CCN(c5ccc(Cl)cn5)CC4)c(C(F)(F)F)c3)cc21]

$^1$H NMR (MeOD) δ: 8.60 (s, 1H), 8.47 (m, 2H), 8.05 (d, 1H), 7.53 (m, 1H), 7.40 (d, 1H), 6.83 (t, 1H), 4.46 (s, 3H), 4.42 (t, 2H), 3.55 (m, 4H), 2.98 (t, 2H), 2.77 (m, 4H). MS m/z 543.2 (M+H).

37c: 6-(4-(2-(4-(3-chloropyridin-2-yl)piperazin-1-yl)ethoxy)-3-(trifluoromethyl)phenyl)-1-methyl-1H-[1,2,3]triazolo[4,5-c]pyridine-4-carbonitrile

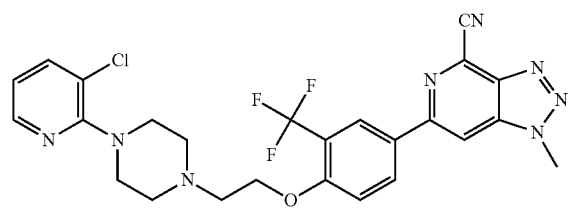 [SMILES: Cn1nnc2c(C#N)nc(-c3ccc(OCCN4CCN(c5ncccc5Cl)CC4)c(C(F)(F)F)c3)cc21]

$^1$H NMR (MeOD) δ: 8.60 (s, 1H), 8.46 (m, 2H), 8.17 (d, 1H), 7.73 (d, 1H), 7.42 (d, 1H), 6.96 (t, 1H), 4.46 (s, 3H), 4.41 (t, 2H), 3.37 (m, 4H), 2.98 (t, 2H), 2.85 (4H, m). MS m/z 543 (M+H).

37d: 1-methyl-6-[3-(trifluoromethyl)-4-(2-(4-(4-(trifluoromethyl)pyridin-2-yl)piperazin-1-yl)ethoxy)phenyl]-1H-1,2,3-triazolo[4,5-c]pyridine-4-carbonitrile

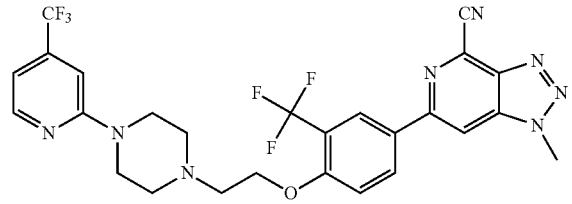 [SMILES: Cn1nnc2c(C#N)nc(-c3ccc(OCCN4CCN(c5cc(C(F)(F)F)ccn5)CC4)c(C(F)(F)F)c3)cc21]

$^1$H NMR (MeOD) δ: 8.60 (s, 1H), 8.46 (m, 2H), 7.41 (d, 1H), 7.01 (s, 1H), 6.85 (d, 1H), 4.46 (s, 3H), 4.41 (t, 2H), 3.65 (m, 4H), 2.98 (t, 2H), 2.78 (m, 4H). MS m/z 577.2 (M+H).

37e: 6-(4-(2-(4-(2-hydroxyethyl)piperazin-1-yl)ethoxy)-3-(trifluoromethyl)phenyl)-1-methyl-1H-[1,2,3]triazolo[4,5-c]pyridine-4-carbonitrile

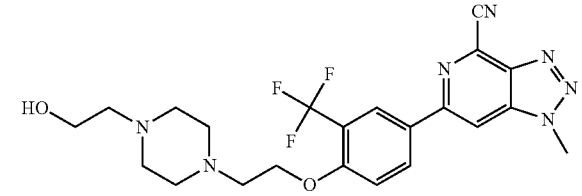 [SMILES: Cn1nnc2c(C#N)nc(-c3ccc(OCCN4CCN(CCO)CC4)c(C(F)(F)F)c3)cc21]

$^1$H NMR (MeOD) δ: 8.59 (s, 1H), 8.45 (m, 2H), 7.37 (d, 1H), 4.45 (s, 3H), 4.36 (t, 2H), 3.69 (m, 4H), 2.92 (t, 2H), 2.54 (m, 4H). MS m/z 476.2 (M+H).

37f: 1-methyl-6-O-(2-O-(pyridin-2-yl)piperazin-1-yl)ethoxy)-3-(trifluoromethyl)phenyl)-1H-[1,2,3]triazolo[4,5-c]pyridine-4-carbonitrile dihydrochloride

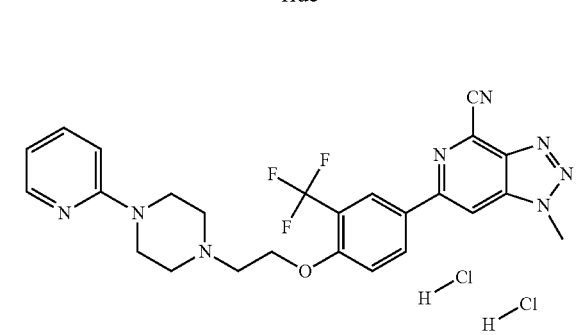

$^1$H NMR (MeOD) δ: 8.63 (s, 1H), 8.13 (d, 1H), 7.91 (t, 1H), 7.49 (d, 1H), 7.25 (d, 1H), 7.00 (t, 1H), 7.70 (m, 2H), 4.29-3.45 (broad m, 10H). MS m/z 545.2 (M+H).

37g: 2-(4-(2-(4-(4-cyano-1-methyl-1H-[1,2,3]triazolo[4,5-c]pyridin-6-yl)-2-(trifluoromethyl)phenoxy)ethyl)piperazin-1-yl)-N,N-dimethylacetamide dihydrochloride

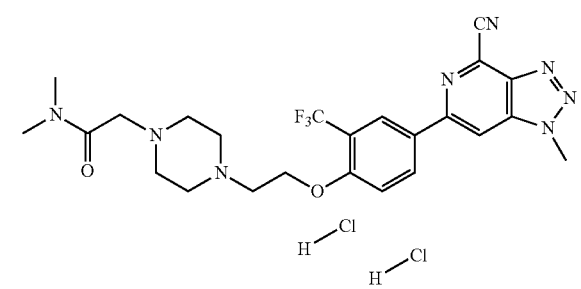

$^1$H NMR (MeOD) δ: 8.62 (s, 1H), 8.50 (m, 2H), 7.43 (d, 1H), 4.70 (m, 2H), 4.46 (s, 3H), 4.37 (s, 2H), 3.75 (broad s, 10H), 2.99 (d, 6H). MS m/z 517.2 (M+H).

37h: 2-(4-(2-(4-(4-cyano-1-methyl-1H-[1,2,3]triazolo[4,5-c]pyridin-6-yl)-2-(trifluoromethyl)phenoxy)ethyl)piperazin-1-yl)acetamide

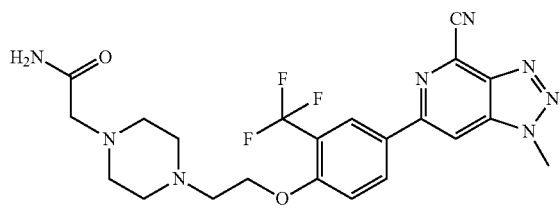 [SMILES: Cn1nnc2c(C#N)nc(-c3ccc(OCCN4CCN(CC(N)=O)CC4)c(C(F)(F)F)c3)cc21]

$^1$H NMR (DMSO) δ: 8.99 (s, 1H), 8.47 (m, 2H), 7.53 (d, 1H), 7.12 (s, 1H), 4.46 (s, 3H), 4.33 (t, 2H), 2.83 (s, 2H), 2.77 (t, 3H), 2.56 (broad s, 4H), 2.44 (broad s, 4H). MS m/z 489.2 (M+H).

37i: 2-(2-(4-(4-cyano-1-methyl-1H-[1,2,3]triazolo[4,5-c]pyridin-6-yl)-2-(trifluoromethyl)phenoxy)ethylamino)acetamide

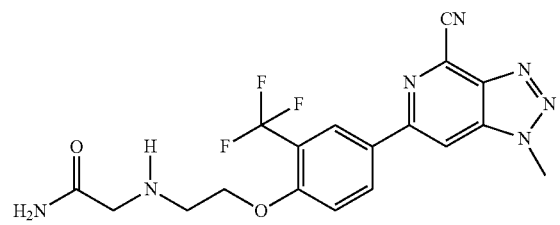 [SMILES: Cn1nnc2c(C#N)nc(-c3ccc(OCCNCC(N)=O)c(C(F)(F)F)c3)cc21]

$^1$H NMR (DMSO) δ: 8.99 (s, 1H), 8.48 (m, 2H), 7.52 (d, 1H), 7.30 (s, 1H), 7.06 (s, 1H), 4.46 (s, 3H), 4.27 (t, 2H), 3.14 (d, 2H), 2.93 (t, 2H). MS m/z 420 (M+H).

37j: 2-(2-(4-(4-cyano-1-methyl-1H-[1,2,3]triazolo[4,5-c]pyridin-6-yl)-2-(trifluoromethyl)phenoxy)ethylamino)-N-methylacetamide

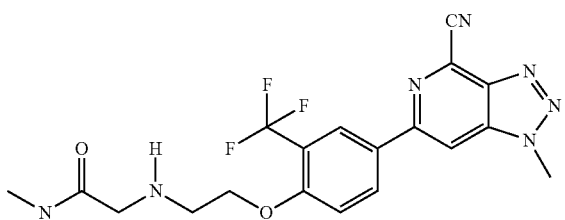

$^1$H NMR (DMSO) δ: 8.99 (s, 1H), 8.48 (m, 2H), 7.75 (broad s, 1H), 7.51 (d, 1H), 4.46 (s, 3H), 4.27 (t, 2H), 4.10 (m, 1H), 3.17 (d, 2H), 2.91 (m, 2H), 2.60 (d, 3H). MS m/z 434 (M+H).

37k: 2-((2-(4-(4-cyano-1-methyl-1H-[1,2,3]triazolo[4,5-c]pyridin-6-yl)-2-(trifluoromethyl)phenoxy)ethyl)(methyl)amino)-N-methylacetamide

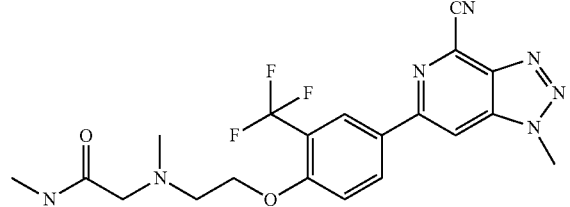

$^1$H NMR (CDCl$_3$) δ: 8.30 (m, 2H), 7.98 (s, 1H), 7.31 (broad s, 1H), 7.26 (s, 1H), 7.14 (d, 1H), 4.44 (s, 3H), 4.21 (t, 2H), 3.15 (s, 2H), 2.95 (t, 2H), 2.80 (d, 3H), 2.44 (s, 3H). MS m/z 488 (M+H).

37l: 2-(2-(4-(4-cyano-1-methyl-1H-[1,2,3]triazolo[4,5-c]pyridin-6-yl)-2-(trifluoromethyl)phenoxy)ethylamino)-N,N-dimethylacetamide

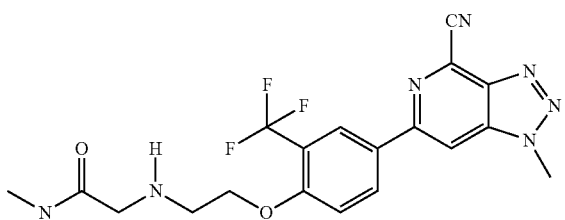

$^1$H NMR (DMSO) δ: 8.96 (s, 1H), 8.45 (m, 2H), 7.49 (d, 1H), 4.46 (s, 3H), 4.29 (t, 2H), 3.45 (s, 2H), 2.97 (t, 2H), 2.92 (s, 3H), 2.94 (s, 3H), 2.18 (s, 1H). MS m/z 448.2 (M+H).

37m: 2-((2-(4-(4-cyano-1-methyl-1H-[1,2,3]triazolo[4,5-c]pyridin-6-yl)-2-(trifluoromethyl)phenoxy)ethyl)(methyl)amino)-N,N-dimethylacetamide

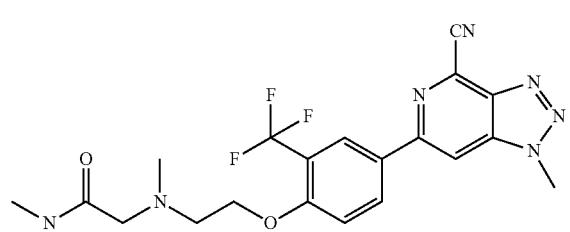

$^1$H NMR (CDCl3) δ: 8.28 (m, 2H), 7.96 (s, 1H), 7.14 (d, 1H), 4.43 (s, 3H), 4.28 (t, 2H), 3.40 (s, 2H), 3.06 (t, 2H), 3.03 (s, 3H), 2.94 (s, 3H), 2.49 (s, 3H). MS m/z 462.2 (M+H).

37n: 2-((2-(4-(4-cyano-1-methyl-1H-[1,2,3]triazolo[4,5-c]pyridin-6-yl)-2-(trifluoromethyl)phenoxy)ethyl)(methyl)amino)acetamide

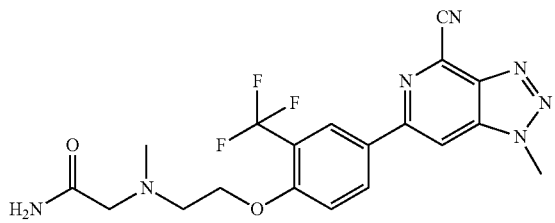 [SMILES: CN(CCOc1ccc(-c2cc3c(nnn3C)c(C#N)n2)cc1C(F)(F)F)CC(N)=O]

MS m/z 334 (M+H).

37o: 1-methyl-6-(4-(2-(4-(methylsulfonyl)piperazin-1-yl)ethoxy)-3-(trifluoromethyl)phenyl)-1H-[1,2,3]triazolo[4,5-c]pyridine-4-carbonitrile

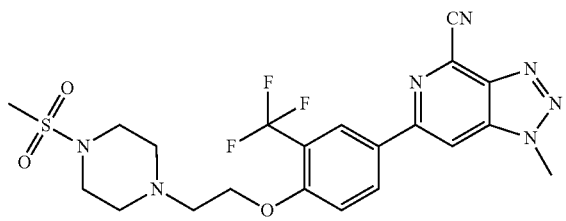 [SMILES: Cn1nnc2c(C#N)nc(-c3ccc(OCCN4CCN(S(C)(=O)=O)CC4)c(C(F)(F)F)c3)cc21]

$^1$H NMR (DMSO) δ: 8.98 (s, 1H), 8.49 (m, 2H), 7.53 (d, 1H), 4.46 (s, 3H), 4.35 (t, 2H), 3.11 (m, 4H), 2.87 (s, 3H), 2.85 (t, 2H), 2.64 (m, 4H). MS m/z 510 (M+H).

37p: 1-methyl-6-(4-(2-(4-S,S-dioxothiomorpholin-1-yl)ethoxy)-3-(trifluoromethyl)phenyl)-1H-[1,2,3]triazolo[4,5-c]pyridine-4-carbonitrile

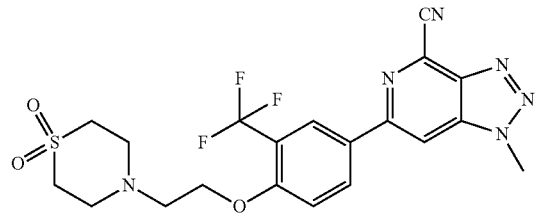 [SMILES: Cn1nnc2c(C#N)nc(-c3ccc(OCCN4CCS(=O)(=O)CC4)c(C(F)(F)F)c3)cc21]

$^1$H NMR (MEOD) δ: 8.57 (s, 1H), 8.45 (m, 2H), 7.37 (d, 1H), 4.45 (s, 3H), 4.34 (t, 2H), 3.21 (m, 4H), 3.12 (m, 6H). MS m/z 481 (M+H).

37q: 1-methyl-6-(3-(trifluoromethyl)-4-(2-(3-(trifluoromethyl)piperazin-1-yl)ethoxy)phenyl)-1H-[1,2,3]triazolo[4,5-c]pyridine-4-carbonitrile

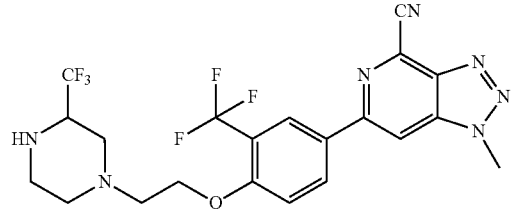 [SMILES: Cn1nnc2c(C#N)nc(-c3ccc(OCCN4CCNC(C(F)(F)F)C4)c(C(F)(F)F)c3)cc21]

$^1$H NMR (DMSO) δ: 8.98 (s, 1H), 8.48 (m, 2H), 7.53 (d, 1H), 4.46 (s, 3H), 4.36 (m, 2H), 3.05 (d, 1H), 2.88-2.65 (broad m, 6H), 2.22-213 (broad m, 2H). MS m/z 500 (M+H).

37r: 1-methyl-6-(4-(2-(3-oxopiperazin-1-yl)ethoxy)-3-(trifluoromethyl)phenyl)-1H-[1,2,3]triazolo[4,5-c]pyridine-4-carbonitrile

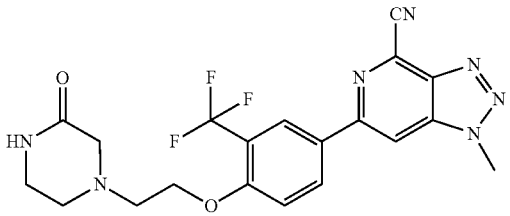 [SMILES: Cn1nnc2c(C#N)nc(-c3ccc(OCCN4CCNC(=O)C4)c(C(F)(F)F)c3)cc21]

$^1$H NMR (DMSO) δ: 8.99 (s, 1H), 8.49 (m, 2H), 7.75 (broad s, 1H), 7.54 (d, 1H), 4.46 (s, 3H), 4.37 (t, 2H), 3.15 (m, 2H), 3.09 (s, 2H), 2.86 (t, 2H), 2.72 (t, 2H). MS m/z 446 (M+H).

37s: 6-(4-(2-(4-(2-hydroxy-2-methylpropyl)piperazin-1-yl)ethoxy)-3-(trifluoromethyl)phenyl)-1-methyl-1H-[1,2,3]triazolo[4,5-c]pyridine-4-carbonitrile dihydrochloride

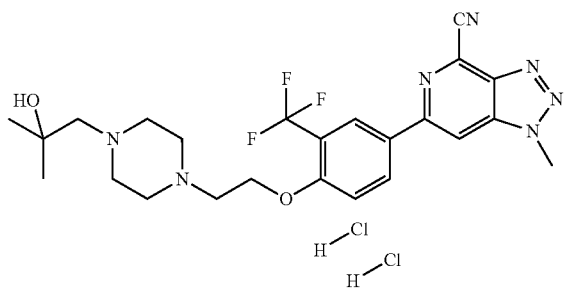

$^1$H NMR (MEOD) δ: 8.64 (s, 1H), 8.52 (m, 2H), 4.62 (t, 2H), 4.46 (s, 3H), 3.78-3.54 (broad m, 10H), 3.21 (broad s, 2H), 1.36 (s, 6H). MS m/z 504.2 (M+H).

37t: 1-methyl-6-(4-(2-(piperazin-1-yl)ethoxy)-3-(trifluoromethyl)phenyl)-1H-[1,2,3]triazolo[4,5-c]pyridine-4-carbonitrile

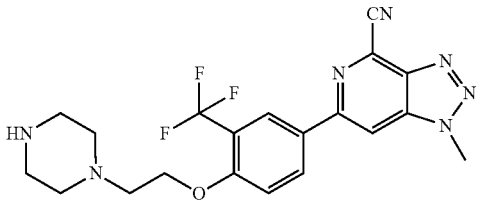 [SMILES: Cn1nnc2c(C#N)nc(-c3ccc(OCCN4CCNCC4)c(C(F)(F)F)c3)cc21]

$^1$H NMR (CDCl3) δ: 8.31 (d, 1H), 8.26 (s, 1H), 7.97 (s, 1H), 7.13 (d, 1H), 4.43 (s, 3H), 4.29 (t, 2H), 2.90 (m, 6H), 2.60 (m, 4H). MS m/z 432 (M+H).

37u: 6-(4-(2-((1S,4S)-2,5-diazabicyclo[2.2.1]heptan-2-yl)ethoxy)-3-(trifluoromethyl)phenyl)-1-methyl-1H-[1,2,3]triazolo[4,5-c]pyridine-4-carbonitrile

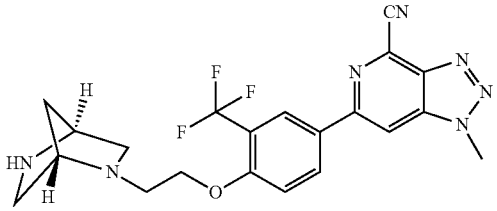 [SMILES: Cn1nnc2c(C#N)nc(-c3ccc(OCCN4C[C@@H]5C[C@H]4CN5)c(C(F)(F)F)c3)cc21]

¹H NMR (CDCl3) δ: 8.29 (m, 2H), 7.95 (s, 1H), 7.15 (d, 1H), 4.43 (s, 3H), 4.38 (m, 1H), 4.24 (m, 2H), 3.52 (d, 2H), 3.18-2.99 (m, 5H), 2.85 (d, 1H), 2.56 (d, 1H), 1.79 (d, 1H), 1.63 (d, 1H). MS m/z 444 (M+H).

EXAMPLE 38a 1-methyl-6-(4-(2-(4-(3,3,3-trifluoro-2-hydroxy-2-methylpropyl)piperazin-1-yl)ethoxy)-3-(trifluoromethyl)phenyl)-1H-[1,2,3]triazolo[4,5-c]pyridine-4-carbonitrile dihydrochloride

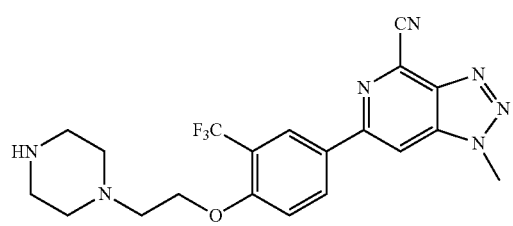

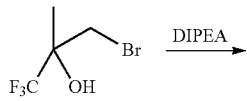

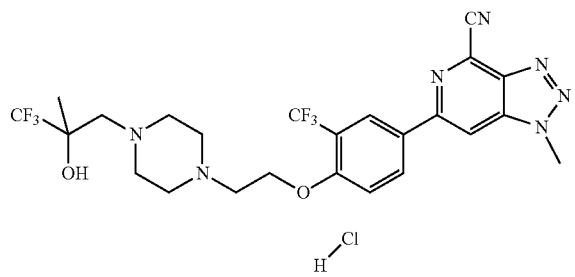

3-Bromo-1,1,1-trifluoro-2-methylpropan-2-ol (47.0 mg) was added to a solution of 1-methyl-6-(4-(2-(piperazin-1-yl)ethoxy)-3-(trifluoromethyl)phenyl)-1H-[1,2,3]triazolo[4,5-c]pyridine-4-carbonitrile (49 mg) and N-ethyl-N-isopropyl-propan-2-amine (0.094 ml, 73.4 mg) Acetonitrile (1 ml). Reaction was heated at 100° C. under microwave condition for 15 minutes. Reaction mixture was filtered and purified by basic prep HPLC to give 1-methyl-6-(4-(2-(4-(3,3,3-trifluoro-2-hydroxy-2-methyl-propyl)piperazin-1-yl)ethoxy)-3-(trifluoromethyl)phenyl)-1H-[1,2,3]triazolo[4,5-c]pyridine-4-carbonitrile. HCl salt formed by adding 0.23 ml 0.5M HCl with another 1 ml of water and lyophilising sample in genevac to afford 1-methyl-6-(4-(2-(4-(3,3,3-trifluoro-2-hydroxy-2-methylpropyl)piperazin-1-yl)ethoxy)-3-(trifluoromethyl)phenyl)-1H-[1,2,3]triazolo[4,5-c]pyridine-4-carbonitrile dihydrochloride (34.7 mg). ¹H NMR (MEOD) δ: 8.62 (s, 1H), 8.15 (m, 2H), 7.43 (d, 1H), 4.64 (t, 2H), 4.46 (s, 3H), 3.72 (t, 2H), 3.52 (broad s, 4H), 2.99 (broad s, 4H), 2.74 (dd, 2H), 1.43 (s, 3H). MS m/z 558.2 (M+H).

The procedure described in Example 38a was further applied, using the appropriate reagents, to prepare the following compound.

38b: 2-((1S,4S)-5-(2-(4-(4-cyano-1-methyl-1H-[1,2,3]triazolo[4,5-c]pyridin-6-yl)-2-(trifluoromethyl)phenoxy)ethyl)-2,5-diazabicyclo[2.2.1]heptan-2-yl)-N,N-dimethylacetamide

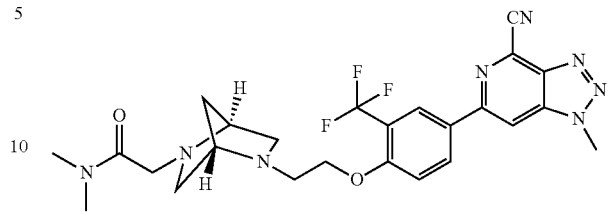

¹H NMR (MEOD) δ: 8.53 (s, 1H), 8.40 (m, 2H), 7.33 (d, 1H), 4.44 (s, 3H), 4.29 (t, 2H), 3.55-3.43 (m, 4H), 3.16-3.00 (broad m, 5H), 2.95-2.57 (broad m, 6H), 2.79 (d, 1H), 1.83 (q, 2H). MS m/z 529.2 (M+H).

EXAMPLE 39

(S)-methyl 3-(4-(2-(4-(4-cyano-1-methyl-1H-[1,2,3]triazolo[4,5-c]pyridin-6-yl)-2-(trifluoromethyl)phenoxy)ethyl)piperidin-1-yl)-2-hydroxypropanoate

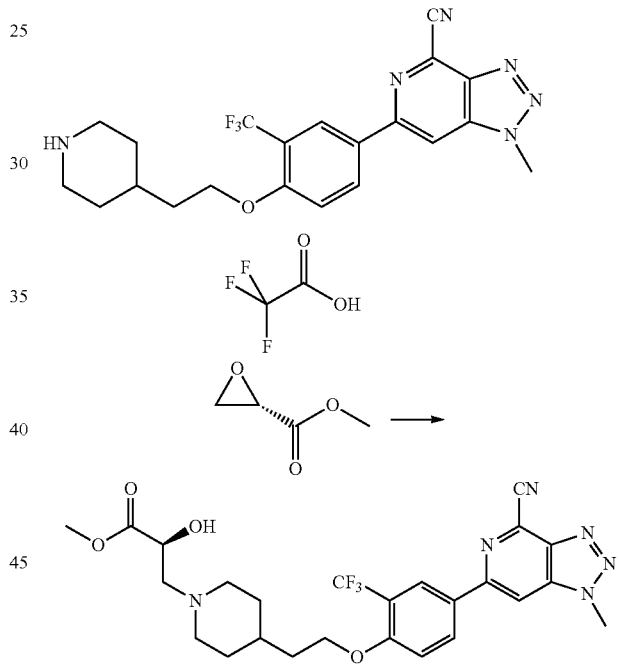

(S)-Methyl oxirane-2-carboxylate (1.837 mmol, 0.188 g), 1-methyl-6-(4-(2-(piperidin-4-yl)ethoxy)-3-(trifluoromethyl)phenyl)-1H-[1,2,3]triazolo[4,5-c]pyridine-4-carbonitrile 2,2,2-trifluoroacetate (0.918 mmol, 0.5 g) and Hunig's base (1.837 mmol, 0.304 ml, 0.237 g) were heated in Methanol (5 ml) to 100° C. for 10 minutes in the microwave. The reaction mixture was concentrated in vacuo. The resulting residue was purified by column chromatography, eluting with DCM—90/10 DCM/MeOH to afford (S)-methyl 3-(4-(2-(4-(4-cyano-1-methyl-1H-[1,2,3]triazolo[4,5-c]pyridin-6-yl)-2-(trifluoro-methyl)phenoxy)ethyl)piperidin-1-yl)-2-hydroxypropanoate. (0.34 g)

¹H NMR (d6-DMSO) δ: 8.94 (s, 1H), 8.46 (m, 2H), 7.48 (d, 1H), 5.31 (m, 1H), 4.45 (s, 3H), 3.62 (s, 3H), 4.23 (t, 2H), 4.18 (m, 1H), 3.63 (s, 3H), 2.85 (br, 2H), 2.54 (1H, m), 2.02 (t, 2H), 1.68 (m, 4H), 1.47 (br, 1H), 1.17 (1H, m). MS m/z 533.0 (M+H).

EXAMPLE 40 tert-Butyl 2-(5-(4-cyano-1-methyl-1H-[1,2,3]triazolo[4,5-c]pyridin-6-yl)-3-(trifluoromethyl)pyridin-2-yloxy)ethyl(methyl)carbamate

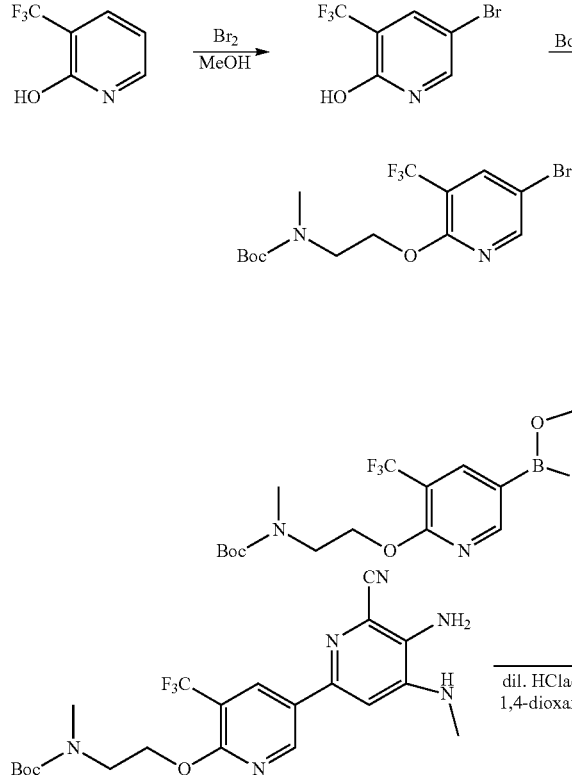
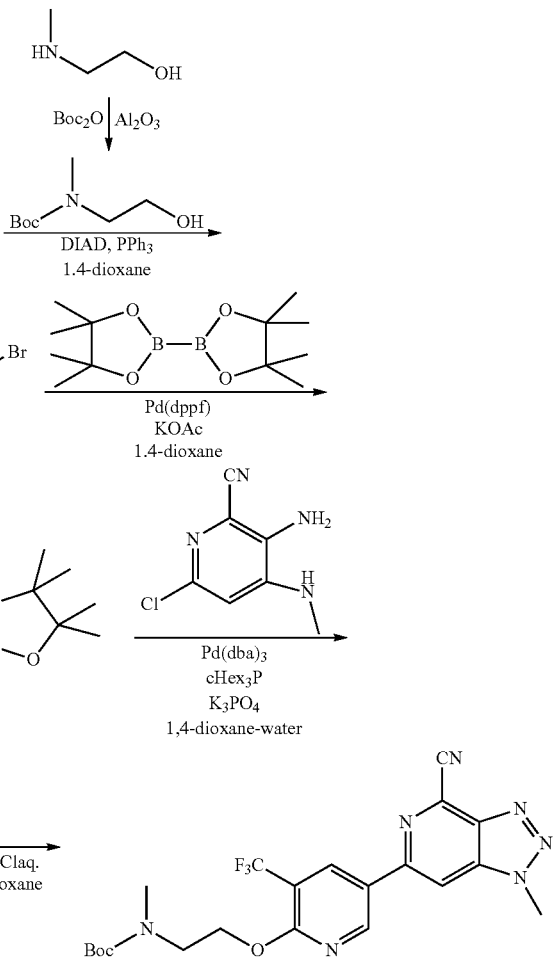

A: tert-Butyl 2-hydroxyethyl(methyl)carbamate 2-(Methylamino)ethanol (1.64 g) was added to aluminum oxide (3.34 g) then di-tert-butyl dicarbonate (5.24 g) was added. The reaction mixture was stirred at 20° C. for 10 min. The residue was diluted in ethyl acetate (2×80 ml), filtered and evaporated to give 4.60 g colourless oil as tert-butyl 2-hydroxyethyl(methyl)carbamate.

$^1$H NMR (CDCl$_3$) δ: 3.7-3.8 (br, 2H), 3.35-3.45 (br, 2H), 2.92 (s, 3H), 1.47 (s, 9H).

B: tert-Butyl 2-(5-bromo-3-(trifluoromethyl)pyridin-2-yloxy)ethyl(methyl)carbamate To a suspension of 5-bromo-3-(trifluoromethyl)pyridin-2-ol (500 mg) in 1,4-dioxane (10 ml), tert-butyl 2-hydroxyethyl(methyl)carbamate (475 mg) and triphenylphosphine (684 mg) were added. Then diisopropyl azodicarboxylate (556 mg) was dropwised and stirred at 20° C. for 1.5 h. The mixture was evaporated off the solvent and purified by Biotage SNAP cartridge KP-Sil column (50 g, heptane:ethyl acetate=1:0, 5:1, 4:1, 3:1 to 2:1) to give 630 mg yellow oil as tert-butyl 2-(5-bromo-3-(trifluoromethyl)pyridin-2-yloxy)ethyl(methyl)carbamate (76%).

$^1$H NMR (CDCl$_3$) δ: 8.33 (d, 1H, J=2.4 Hz), 7.94 (d, 1H, J=1.2 Hz), 4.51 (br, 2H), 3.61 (br, 2H), 2.94 (s, 3H), 1.44 (s, 9H).

C: tert-Butyl methyl(2-(5-(4,4,5,5-tetramethyl-1,3,2-dioxaborolan-2-yl)-3-(trifluoromethyl)pyridin-2-yloxy)ethyl)carbamate A suspension of tert-butyl 2-(5-bromo-3-(trifluoromethyl)pyridin-2-yloxy)ethyl(methyl)carbamate (600 mg), bis(pinacolato)diboron (487 mg), 1,1'-bis-(diphenylphosphino)ferrocenedichloropalladium(II) (54.9 mg) and potassium acetate (447 mg) in dry 1,4-dioxane (15 ml) was stirred at 100° C. for 2 h. The solvent was evaporated and partitioned between water and dichloromethane then separated. The aqueous layer was extracted further with dichloromethane, combined organic layer was dried over sodium sulfate, filtered and concentrated. Purified by Biotage SNAP cartridge KP-Sil column (25 g, heptane:ethyl acetate=1:0 to 5:1) to give 450 mg colourless solid as tert-butyl methyl(2-(5-(4,4,5,5-tetramethyl-1,3,2-dioxaborolan-2-yl)-3-(trifluoromethyl)pyridin-2-yloxy)ethyl)carbamate (67%).

$^1$H NMR (CDCl$_3$) δ: 8.63 (s, 1H), 8.21 (s, 1H), 4.56 (br, 2H), 3.63 (br, 2H), 2.95 (s, 3H), 1.46 (s, 9H), 1.35 (s, 12H).

D: tert-Butyl 2-(5-amino-6-cyano-4-(methylamino)-5'-(trifluoromethyl)-2,3'-bipyridin-6'-yloxy)ethyl (methyl)carbamate A suspension of tert-butyl methyl(2-(5-(4,4,5,5-tetramethyl-1,3,2-dioxaborolan-2-yl)-3-(trifluoromethyl)pyridin-2-yloxy)ethyl)carbamate (440 mg), 3-amino-6-chloro-4-(methylamino)picolinonitrile (135 mg), tris(dibenzylideneacetone)dipalladium (0) (34.9 mg), tricyclohexylphosphine (25.7 mg) and potassium phosphate (327 mg) in 1,4-dioxane (10 ml) and water (5 ml) was stirred at 100° C. for 2 h. The reaction mixture was cooled and partitioned between water and ethyl acetate, washed with water, brine, dried over sodium sulfate, filtered and concentrated. Purified by Biotage SNAP cartridge KP-Sil column (25 g, heptane:ethyl acetate=1:0, 3:1, 2:1, 1:1 to 1:2) to give 170 mg orange amorphous as tert-butyl 2-(5-amino-6-cyano-4-(methylamino)-5'-(trifluoromethyl)-2,3'-bipyridin-6'-yloxy)ethyl(methyl)carbamate (49%).

$^1$H NMR (CDCl$_3$) δ: 8.77 (s, 1H), 8.45 (s, 1H), 6.88 (s, 1H), 4.60 (br, 2H), 4.30 (br, 1H), 3.90 (br, 2H), 3.65 (br, 2H), 3.02 (s, 3H), 2.97 (s, 3H), 1.46 (s, 9H).

E: tert-Butyl 2-(5-(4-cyano-1-methyl-1H-[1,2,3]triazolo[4,5-c]pyridin-6-yl)-3-(trifluoro-methyl)pyridin-2-yloxy)ethyl(methyl)carbamate To a suspension of tert-butyl 2-(5-amino-6-cyano-4-(methylamino)-5'-(trifluoromethyl)-2,3'-bipyridin-6'-yloxy)ethyl(methyl)carbamate (160 mg) in water (3 ml) and 1,4-dioxane (3 ml), 2N hydrochloric acid (192 mg) was added at 0° C. and sodium nitrite (34.2 mg) in water (1 ml) was added then stirred at 0° C. for 10 min then at 20° C. for 20 h. The reaction mixture was filtered, washed with water, dried in vacuum oven to give 140 mg light yellow solid as tert-butyl 2-(5-(4-cyano-1-methyl-1H-[1,2,3]triazolo[4,5-c]pyridin-6-yl)-3-(trifluoromethyl)pyridin-2-yloxy)ethyl(methyl)-carbamate (85%).

$^1$H NMR (CDCl$_3$) δ: 9.02 (s, 1H), 8.62 (s, 1H), 7.99 (s, 1H), 4.65 (br, 2H), 4.46 (s, 3H), 3.68 (br, 2H), 2.99 (s, 3H), 1.46 (s, 9H). MS m/z: 478 (M+H).

EXAMPLE 41

N-(2-(4-(4-cyano-1-methyl-1H-[1,2,3]triazolo[4,5-d]pyridin-6-yl)-2-(trifluoromethyl)phenoxy)ethyl)acetamide

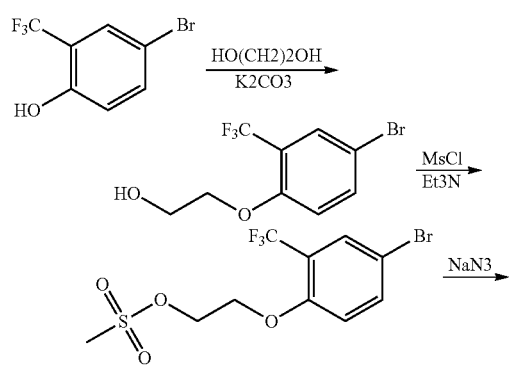

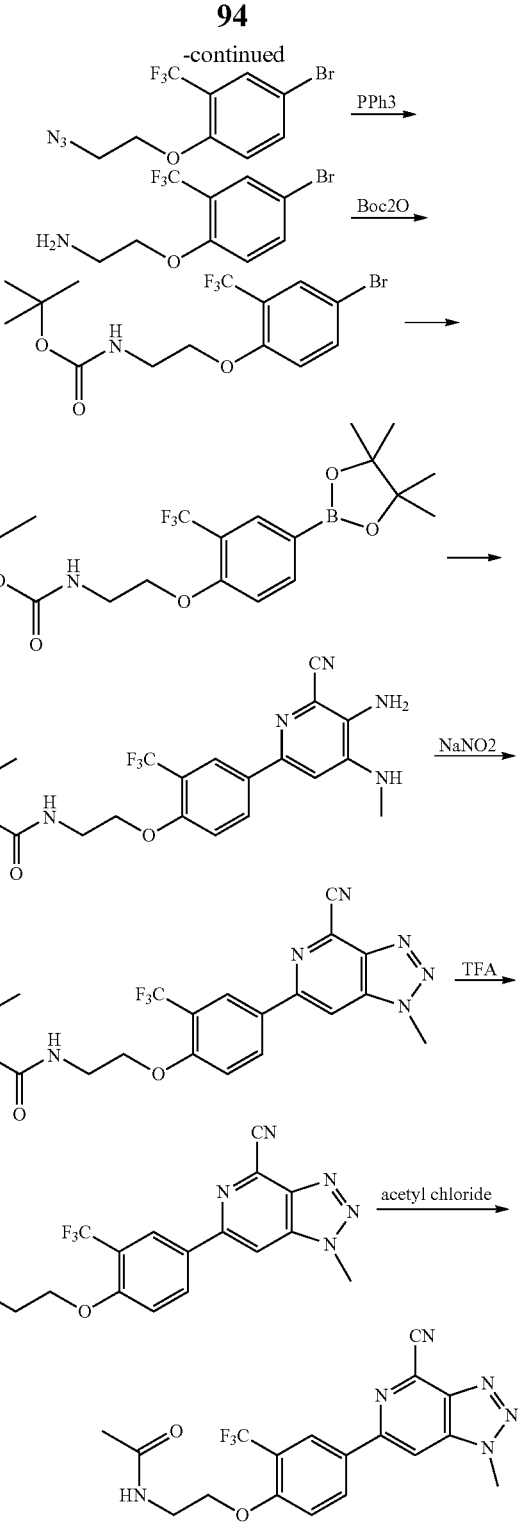

A: 2-(4-bromo-2-(trifluoromethyl)phenoxy)ethanol

4-Bromo-2-(trifluoromethyl)phenol (83 mmol, 20 g), potassium carbonate (166 mmol, 22.94 g) and 2-bromoethanol (124 mmol, 8.79 mL, 15.56 g) were combined and heated to reflux for overnight in Acetonitrile (200 mL). The reaction mixture was washed with water, 0.5M NaOH, dried over sodium sulfate and concentrated in vacuo. The resulting residue was taken up in hot heptane (300 mL) and allowed to crystallise. The solid was filtered off to afford 2-(4-bromo-2-(trifluoromethyl)-phenoxy)ethanol. (20.74 g)

$^1$H NMR (CDCl3) δ: 7.69 (s, 1H), 7.60 (d, 1H), 6.91 (s, 1H), 4.14 (t, 2H), 3.98 (t, 2H)

B: 2-(4-bromo-2-(trifluoromethyl)phenoxy)ethyl methanesulfonate 2-(4-Bromo-2-(trifluoromethyl)phenoxy)ethanol (17.54 mmol, 5 g) and triethylamine (35.1 mmol, 4.88 ml, 3.55 g) were combined and stirred in DCM (100 ml) at 0° C. methanesulfonyl chloride (26.3 mmol, 2.036 ml, 3.01 g) was added and the reaction allowed to warm to room temperature over 1 hour. The reaction mixture was washed with water, dried over sodium sulfate and concentrated in vacuo to afford 2-(4-bromo-2-(trifluoromethyl)phenoxy)ethyl methanesulfonate. (5.64 g)

$^1$H NMR (CDCl3) δ: 7.70 (s, 1H), 7.62 (d, 1H), 6.90 (d, 1H), 4.56 (t, 2H), 4.31 (t, 2H) 3.06 (s, 3H).

C: 1-(2-azidoethoxy)-4-bromo-2-(trifluoromethyl) benzene 2-(4-Bromo-2-(trifluoromethyl)phenoxy)ethyl methanesulfonate (15.54 mmol, 5.643 g) and potassium carbonate (46.6 mmol, 6.44 g) were combined and stirred in DMF (50 ml). Sodium azide (46.6 mmol, 3.03 g) was added and the reaction stirred at room temperature overnight. Starting material remained. Reaction was heated to 60° C. for 5 hours. The reaction mixture was poured into water and diluted with EtOAc. The layers were separated and the organic dried over sodium sulfate and concentrated in vacuo. The resulting residue was purified by silica chromatography, eluting with a gradient of heptane—50/50 heptane/EtOAc to afford 1-(2-azidoethoxy)-4-bromo-2-(trifluoromethyl)benzene. (2.27 g)

$^1$H NMR (CDCl3) δ: 7.70 (s, 1H), 7.60 (d, 1H), 6.88 (d, 1H), 4.17 (t, 2H), 3.64 (t, 2H).

D: 2-(4-bromo-2-(trifluoromethyl)phenoxy)ethanamine 1-(2-Azidoethoxy)-4-bromo-2-(trifluoromethyl)benzene (7.32 mmol, 2.271 g) and triphenylphosphine (10.99 mmol, 2.88 g) were combined and stirred for 1 hour in THF (5 ml). The reaction mixture was concentrated in vacuo. The residue was taken up in EtOAc/water, the layers separated and the organic dried over sodium sulfate and concentrated in vacuo. The resulting residue was passed down an SCX column to afford 2-(4-bromo-2-(trifluoromethyl)phenoxy)ethanamine. (1.30 g)

$^1$H NMR (CDCl3) δ: 7.68 (s, 1H), 7.57 (d, 1H), 6.88 (d, 1H), 4.06 (t, 2H), 3.11 (t, 2H).

E: tert-butyl 2-(4-bromo-2-(trifluoromethyl)phenoxy)ethylcarbamate 2-(4-Bromo-2-(trifluoromethyl)phenoxy)ethanamine (4.56 mmol, 1.296 g) and di-tert-butyl dicarbonate (4.56 mmol, 0.996 g) were combined in DCM (30 ml) for 2 hours. The reaction mixture was washed with water, layers separated and the organic dried over Sodium sulfate and concentrated in vacuo to afford tert-butyl 2-(4-bromo-2-(trifluoromethyl)phenoxy)ethylcarbamate. (1.88 g)

$^1$H NMR (CDCl3) δ: 7.68 (s, 1H), 7.58 (d, 1H), 6.87 (d, 1H), 4.08 (t, 2H), 3.55 (t, 2H), 1.44 (s, 9H).

F: tert-butyl 2-(4-(4,4,5,5-tetramethyl-1,3,2-dioxaborolan-2-yl)-2-(trifluoromethyl)-phenoxy)ethylcarbamate tert-Butyl 2-(4-bromo-2-(trifluoromethyl)phenoxy)ethylcarbamate (4.87 mmol, 1.87 g), bis(pinacolato)diboron (5.84 mmol, 1.483 g) potassium acetate (9.73 mmol, 0.955 g) and 1,1′-bis(diphenylphosphino)ferrocenedichloropalladium(II) (0.243 mmol, 0.176 g) were combined in Dioxane (15 ml) and heated to 80° C., under nitrogen, for 3 hours. The reaction mixture was allowed to cool, diluted with EtOAc (300 ml) and washed with water (3×150 ml) and brine (100 ml). Organics were dried over sodium sulphate and solvent evaporated under reduced pressure to yield crude product as a brown oil. Purification by flash chromatography, eluting with 90/10 heptane/EtOAc to afford tert-butyl 2-(4-(4,4,5,5-tetramethyl-1,3,2-dioxaborolan-2-yl)-2-(trifluoromethyl)-phenoxy)ethylcarbamate. (1.22 g)

$^1$H NMR (CDCl3) δ: 8.01 (s, 1H), 7.91 (d, 1H), 6.95 (d, 1H), 4.13 (t, 2H), 3.57 (t, 2H), 1.44 (s, 12H), 1.34 (s, 9H), 3.07 (t, 1H).

G: tert-butyl 2-(4-(5-amino-6-cyano-4-(methylamino)pyridin-2-yl)-2-(trifluoromethyl)phenoxy) ethylcarbamate tert-Butyl 2-(4-(4,4,5,5-tetramethyl-1,3,2-dioxaborolan-2-yl)-2-(trifluoromethyl)-phenoxy)ethylcarbamate (4.34 mmol, 1.87 g), 3-amino-6-chloro-4-(methylamino)-picolinonitrile (4.34 mmol, 0.792 g), potassium phosphate (13.01 mmol, 2.76 g), tricyclohexylphosphine (0.520 mmol, 0.146 g), and tris(dibenzylacetone)dipalladium (0) (0.217 mmol, 0.199 g) were dissolved in Dioxane (20 ml) and Water (10.00 ml) and stirred under nitrogen at 100° C. for 2 hrs. The mixture was diluted with ethyl acetate and filtered through celite. Organic layer was washed with water and separated from the aqueous layer, the organic layer was concentrated in vacuo. This was purified by silica chromatography, eluting with heptane—50/50 heptane/EtOAc to afford tert-butyl 2-(4-(5-amino-6-cyano-4-(methylamino)pyridin-2-yl)-2-(trifluoro-methyl)phenoxy)ethylcarbamate. (0.51 g)

$^1$H NMR (CH3OD) δ: 8.06 (d, 1H), 8.03 (dd, 1H), 7.23 (d, 1H), 6.87 (s, 1H), 4.17 (t, 2H), 3.48 (t, 2H), 2.98 (s, 3H), 1.45 (s, 9H), 3.07. MS m/z 452.0 (M+H).

H: tert-butyl 2-(4-(4-cyano-1-methyl-1H-[1,2,3]triazolo[4,5-c]pyridin-6-yl)-2-(trifluoromethyl)phenoxy) ethylcarbamate tert-Butyl 2-(4-(5-amino-6-cyano-4-(methylamino)pyridin-2-yl)-2-(trifluoromethyl)phenoxy)ethylcarbamate (1.130 mmol, 0.51 g) was dissolved in 1M Hydrochloric Acid (2.259 mmol, 2.259 ml) and dioxane (5 ml). Sodium nitrite (1.582 mmol, 0.109 g) in water (5.00 ml) was added to the reaction mixture and it was stirred at room temperature for 1 hr. The reaction mixture was filtered and the solid washed with water to afford tert-butyl 2-(4-(4-cyano-1-methyl-1H-[1,2,3]triazolo[4,5-c]pyridin-6-yl)-2-(trifluoromethyl)phenoxy)ethylcarbamate. (0.61 g)

$^1$H NMR (d6-DMSO) δ: 8.96 (s, 1H), 8.47 (m, 2H), 7.59 (d, 1H), 6.88 (s, 1H), 4.46 (s, 3H), 4.42 (t, 2H), 3.30 (t, 2H). MS m/z 485.0 (M+Na).

I: N-(2-(4-(4-cyano-1-methyl-1H-[1,2,3]triazolo[4,5-c]pyridin-6-yl)-2-(trifluoromethyl)phenoxy)ethyl) acetamide 6-(4-(2-Aminoethoxy)-3-(trifluoromethyl)phenyl)-1-methyl-1H-[1,2,3]triazolo-[4,5-c]pyridine-4-carbonitrile (0.276 mmol, 0.1 g) and Hunig's base (0.828 mmol, 0.137 ml, 0.107 g) were stirred in THF (1 ml) at 0° C. acetyl chloride (0.552 mmol, 0.039 ml, 0.043 g) was added and the reaction was allowed to warm to room temperature and stirred for 1 hour. The resulting residue was taken up in DCM and washed with water. The organic was concentrated at reduced pressure. The resulting residue was purified by silica chromatography, eluting with DCM—3% MeOH/DCM to afford N-(2-(4-(4-cyano-1-methyl-1H-[1,2,3]triazolo[4,5-c]pyridin-6-yl)-2-(trifluoromethyl)phenoxy)ethyl)acetamide. (0.024 g)

$^1$H NMR (d6-DMSO) δ: 8.96 (s, 1H), 8.47 (m, 2H), 8.00 (m, 1H), 7.50 (d, 1H), 4.46 (s, 3H), 4.24 (t, 2H), 3.46 (q, 2H), 1.83 (s, 3H). MS m/z 405.0 (M+H).

EXAMPLE 42 tert-butyl 2-(4-(4-cyano-1-methyl-1H-[1,2,3]triazolo[4,5-c]pyridin-6-yl)-2-(trifluoromethyl)phenoxy)ethyl(methyl)carbamate

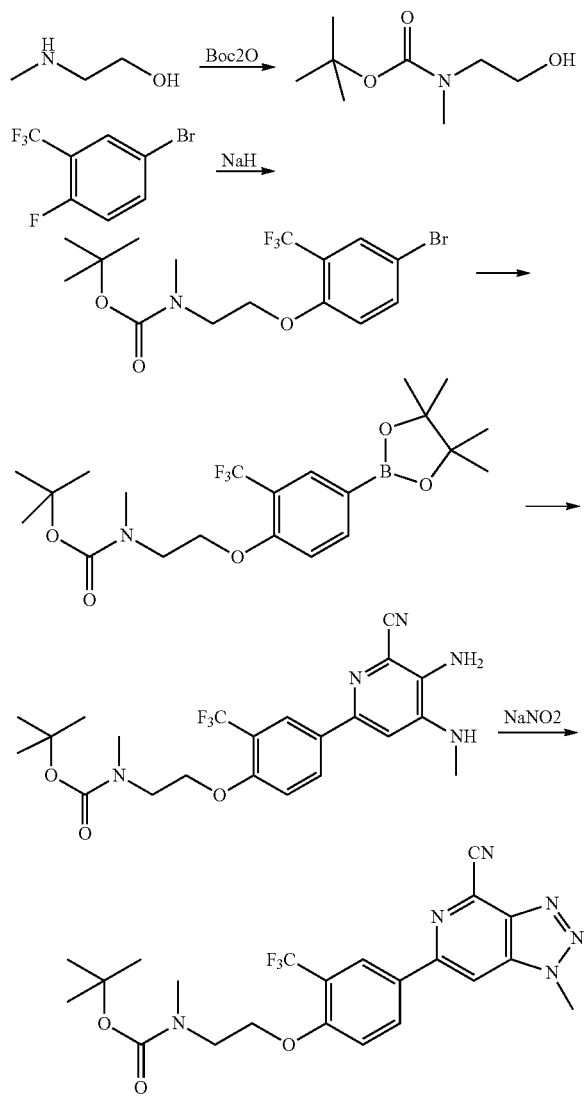

A: tert-butyl 2-(4-bromo-2-(trifluoromethyl)phenoxy)ethyl(methyl)carbamate

Sodium hydride (247 mmol, 9.88 g) was stirred in DMF (100 ml) at room temperature. triethylamine (165 mmol, 22.88 ml, 16.66 g) was added. tert-butyl 2-hydroxyethyl(methyl)carbamate (173 mmol, 30.3 g) was added dropwise in DMF. 4-bromo-1-fluoro-2-(trifluoromethyl)benzene (165 mmol, 40 g) was added in one portion and the reaction was stirred at room temperature overnight. The reaction mixture was diluted with EtOAc and washed with water. The organic was dried over sodium sulfate and concentrated in vacuo. The resulting residue was purified by flash chromatography eluting with heptane—60/40 heptane/EtOAc. Fractions were collected and combined to afford tert-butyl 2-(4-bromo-2-(trifluoromethyl)phenoxy)-ethyl(methyl)carbamate. (18.44 g)

$^1$H NMR (CDCl3) δ: 7.68 (s, 1H), 7.59 (d, 1H), 6.88 (d, 1H), 4.15 (t, 2H), 3.63 (t, 2H), 2.98 (s, 3H), 1.46 (s, 9H).

B: tert-butyl 2-hydroxyethyl(methyl)carbamate 2-(Methylamino)ethanol (399 mmol, 30 g) and di-tert-butyl dicarbonate (379 mmol, 83 g) were combined and stirred at room temperature for 2 hours. The reaction mixture was washed with water and the organic dried over $Na_2SO_4$ and concentrated in vacuo to afford tert-butyl 2-hydroxyethyl(methyl)carbamate. (69 g)

$^1$H NMR (CDCl$_3$) δ: 3.75 (m, 2H), 3.40 (t, 2H), 2.92 (s, 3H), 1.47 (s, 9H).

C: tert-butyl methyl(2-(4-(4,4,5,5-tetramethyl-1,3,2-dioxaborolan-2-yl)-2-(trifluoromethyl)phenoxy)ethyl)carbamate tert-Butyl 2-(4-bromo-2-(trifluoromethyl)phenoxy)ethyl(methyl)carbamate (46.2 mmol, 18.4 g), bis(pinacolato)diboron (55.4 mmol, 14.08 g), potassium acetate (92 mmol, 9.07 g) and 1,1'-bis(diphenylphosphino)ferrocenedichloropalladium(II) (2.310 mmol, 1.672 g) were combined in Dioxane (75 ml) and heated to 80° C., under nitrogen, for 3 hours. The reaction mixture was allowed to cool, diluted with EtOAc (300 ml) and washed with water (3×150 ml) and brine (100 ml). Organics were dried over sodium sulphate and solvent evaporated under reduced pressure to yield crude product as a brown oil. Purification by flash chromatography, eluting with 90/10 heptane/EtOAc to 70/30 heptane/EtOAc to afford tert-butyl methyl(2-(4-(4,4,5,5-tetramethyl-1,3,2-dioxaborolan-2-yl)-2-(trifluoromethyl)phenoxy)ethyl)carbamate. (19.2 g)

$^1$H NMR (CDCl$_3$) δ: 8.00 (s, 1H), 7.91 (d, 1H), 6.96 (d, 1H), 4.19 (br, 2H), 3.64 (br, 2H), 2.98 (s, 3H), 1.48 (s, 12H), 1.26 (s, 9H).

D: tert-butyl 2-(4-(5-amino-6-cyano-4-(methylamino)pyridin-2-yl)-2-(trifluoromethyl)phenoxy)ethyl(methyl)carbamate tert-Butyl methyl(2-(4-(4,4,5,5-tetramethyl-1,3,2-dioxaborolan-2-yl)-2-(trifluoromethyl)phenoxy)ethyl)carbamate (22.46 mmol, 10 g), 3-amino-6-chloro-4-(methylamino)picolinonitrile (22.46 mmol, 4.10 g), potassium phosphate (67.4 mmol, 14.30 g), tricyclohexylphosphine (2.69 mmol, 0.756 g), and tris(dibenzylacetone)-dipalladium (0) (1.123 mmol, 1.028 g) were dissolved in Dioxane (20 ml) and Water (10.00 ml) and stirred under nitrogen at 100° C. for 2 hrs. The mixture was diluted with ethyl acetate and filtered through celite. Organic layer was washed with water and separated from the aqueous layer, the organic layer was concentrated in vacuo. This was purified by silica chromatography, eluting with heptane—50/50 heptane/EtOAc to afford tert-butyl 2-(4-(5-amino-6-cyano-4-(methylamino)pyridin-2-yl)-2-(trifluoro-methyl)phenoxy)ethyl(methyl)carbamate. (2.11 g)

$^1$H NMR(CH3OD) δ: 8.10 (br, 2H), 7.06 (d, 1H), 6.90 (s, 1H), 4.22 (br, 2H), 3.66 (br, 2H), 3.01 (m, 6H), 1.47 (s, 9H). MS m/z 466.0 (M+H).

E: tert-butyl 2-(4-(4-cyano-1-methyl-1H-[1,2,3]triazolo[4,5-c]pyridin-6-yl)-2-(trifluoromethyl)phenoxy)ethyl(methyl)carbamate tert-Butyl 2-(4-(5-amino-6-cyano-4-(methylamino)pyridin-2-yl)-2-(trifluoro-methyl)phenoxy)ethyl(methyl)carbamate (7.43 mmol, 3.46 g) was dissolved in 1M Hydrochloric Acid (14.87 mmol, 14.87 ml) and Dioxane (5 ml). Sodium nitrite (10.41 mmol, 0.718 g) in Water (5.00 ml) was added to the reaction mixture and it was stirred at room temperature for 1 hr. The acetonitrile was removed and the reaction taken up in dioxane/water. The reaction mixture was filtered and the solid washed with water to afford tert-butyl 2-(4-(4-cyano-1-methyl-1H-[1,2,3]triazolo[4,5-c]pyridin-6-yl)-2-(trifluoromethyl)phenoxy)ethyl(methyl)carbamate. (2.82 g)

$^1$H NMR (d6-DMSO) δ: 8.96 (s, 1H), 8.48 (m, 2H), 7.52 (d, 1H), 4.45 (s, 3H), 4.34 (br, 2H), 3.62 (s, 3H), 2.90 (br, 2H), 1.40 (s, 9H). MS m/z 477.0 (M+H).

EXAMPLE 43

6-(4-((3-isopropyl-1,2,4-oxadiazol-5-yl)methoxy)-3-(trifluoromethyl)phenyl)-1-methyl-1H-[1,2,3]triazolo[4,5-c]pyridine-4-carbonitrile

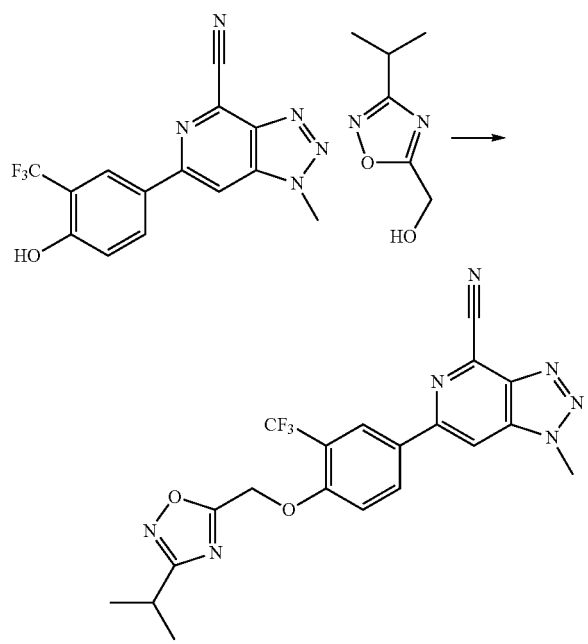

6-(4-Hydroxy-3-(trifluoromethyl)phenyl)-1-methyl-1H-[1,2,3]triazolo[4,5-c]pyridine-4-carbonitrile (0.313 mmol, 100 mg) (3-isopropyl-1,2,4-oxadiazol-5-yl)methanol (0.626 mmol, 89 mg) and triphenylphosphine (0.470 mmol, 123 mg) were suspended in DCM (2 ml) and DIAD (0.470 mmol, 0.093 ml, 95 mg) added. The reaction was stirred at room temperature for 20 hours. The reaction mixture was diluted with DCM (15 ml) and washed with 1M HCl (10 ml) 1M NaOH (10 ml) and brine. Organics were dried over sodium sulphate and solvent evaporated under reduced pressure to yield an orange coloured solid. The solid was suspended in MeOH (4 ml) sonicated and heated to 50 C. for 10 minutes. Filtration of the suspension and washing of the resulting white solid with ether afforded 6-(4-((3-isopropyl-1,2,4-oxadiazol-5-yl)methoxy)-3-(trifluoromethyl)phenyl)-1-methyl-1H-[1,2,3]triazolo[4,5-c]pyridine-4-carbonitrile (60.2% yield) after drying. $^1$H NMR (CDCl3) δ: 8.38 (d, 1H), 8.32 (s, 1H), 7.98 (s, 1H), 7.27 (d, 1H), 5.45 (s, 2H), 4.44 (s, 3H), 3.12 (m, 1H), 1.36 (d, 6H). MS m/z 444 (M+H).

EXAMPLE 44

6-(4-(3-hydroxypropyl)-3-(trifluoromethyl)phenyl)-1-methyl-1H-[1,2,3]triazolo[4,5-c]pyridine-4-carbonitrile

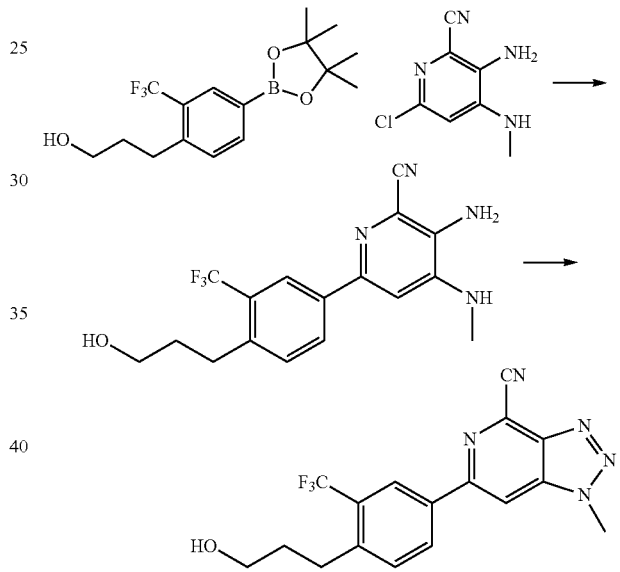

3-(4-(4,4,5,5-Tetramethyl-1,3,2-dioxaborolan-2-yl)-2-(trifluoromethyl)phenyl)-propan-1-ol (3.4 g), 3-amino-6-chloro-4-(methylamino)picolinonitrile (1.9 g), tris(di-benzylideneacetone)dipalladium (0.47 g), tricyclophosphine (0.35 g) and potassium phosphate (6.5 g) were added to the mixed solvent of dioxane (15 ml) and water (8 ml). The mixture was then heated at 100° C. under nitrogen for 2 hours. After diluting with ethyl acetate (100 ml), water layer was removed, organic layer dried over sodium sulphate, solvent removed under vacuum. The residue was then dissolved in NMP (30 ml) and 2M hydrochloric acid (50 ml) was added. Sodium nitrite (0.71 g) in water (5 ml) was then added dropwise during 2 minutes and the resulting mixture was stirred at rt for another 12 hours. After diluting with ethyl acetate (200 ml), the mixture was then washed with water (4×100 ml), brine (100 ml). Dried over sodium sulphate, solvent removed under vacuum. To the residue was then added ethanol (10 ml), the product precipitated and collected by filtration to give 6-(4-(3-hydroxypropyl)-3-(trifluoromethyl)phenyl)-1-methyl-1H-[1,2,3]triazolo[4,5-c]pyridine-4-carbonitrile.

¹H NMR (CDCl3) δ: 8.36 (s, 1H), 8.24 (d, 1H), 8.03 (s, 1H), 7.55 (d, 1H), 4.45 (s, 3H), 3.77 (t, 2H), 2.95 (t, 2H), 1.95 (m, 2H). MS m/z 362 (M+H).

EXAMPLE 45

N-(3-(4-(4-cyano-1-methyl-1H-[1,2,3]triazolo[4,5-c]pyridin-6-yl)-2-(trifluoromethyl)phenyl)propyl)-2-(dimethylamino)-N-methylacetamide

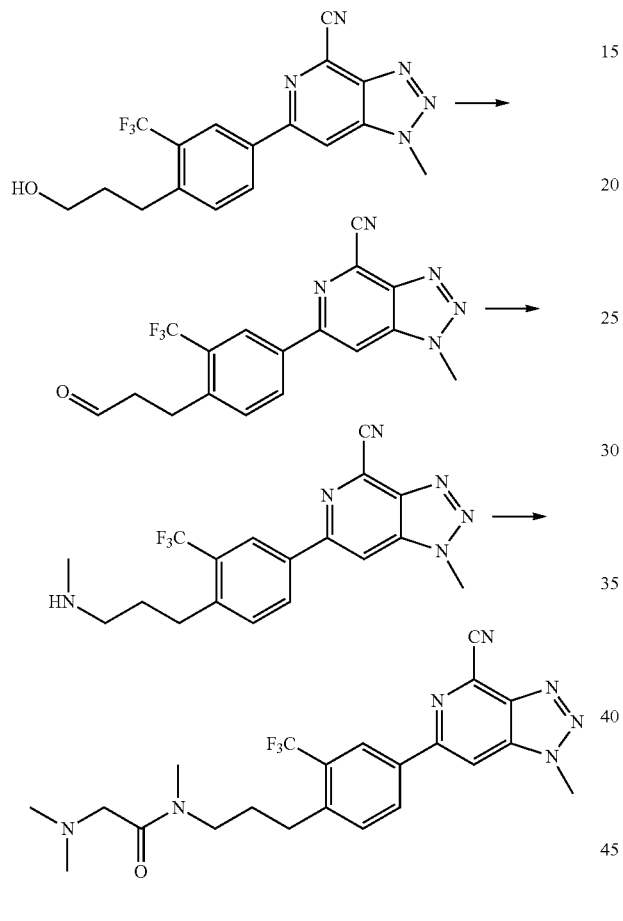

A: methyl-6-(4-(3-oxopropyl)-3-(trifluoromethyl)phenyl)-1H-[1,2,3]triazolo[4,5-c]pyridine-4-carbonitrile To 6-(4-(3-hydroxypropyl)-3-(trifluoromethyl)phenyl)-1-methyl-1H-[1,2,3]triazolo[4,5-c]pyridine-4-carbonitrile (0.65 g) in DMSO (10 ml) was added the DCM solution of Dess-Martin (15%, w/w) (10 ml). The mixture was stirred at rt for 2 hours. After diluting with ethyl acetate (150 ml), the mixture was washed with water (20 ml×4), brine (20 ml), dried over sodium sulphate, solvent removed under reduced pressure. The residue was then dissolved in ethyl acetate (20 ml). After standing overnight, precipitate was then filtered off, filtrate concentrated to give methyl-6-(4-(3-oxopropyl)-3-(trifluoromethyl)phenyl)-1H-[1,2,3]triazolo[4,5-c]pyridine-4-carbonitrile (620 mg). ¹H NMR (CDCl3) δ: 9.88 (s, 1H), 8.36 (s, 1H), 8.26 (d, 1H), 8.05 (d, 1H), 7.55 (d, 1H), 4.46 (s, 3H), 3.22 (t, 2H), 2.86 (t, 2H). MS m/z 360 (M+H).

B: methyl-6-(4-(3-(methylamino)propyl)-3-(trifluoromethyl)phenyl)-1H-[1,2,3]triazolo-[4,5-c]pyridine-4-carbonitrile NaB(OAc)₃H (640 mg) was added in portions to the solution of methyl-6-(4-(3-oxopropyl)-3-(trifluoromethyl)phenyl)-1H-[1,2,3]triazolo[4,5-c]pyridine-4-carbonitrile, methylamine (1.5 ml, 2M in methanol) in THF (5 ml). The mixture was stirred at rt for 3 hours, then diluted with ethyl acetate (100 ml), washed with sodium carbonate (100 ml), brine (100 ml), dried over sodium sulphate, solvent removed. The crude product was used for next step without further purification (260 mg). MS m/z 375 (M+H).

C: N-(3-(4-(4-cyano-1-methyl-1H-[1,2,3]triazolo[4,5-c]pyridin-6-yl)-2-(trifluoromethyl)phenyl)propyl)-2-(dimethylamino)-N-methylacetamide EDCI (290 mg) was added to the mixture of 2-(dimethylamino)acetic acid (155 mg), methyl-6-(4-(3-(methylamino)propyl)-3-(trifluoromethyl)phenyl)-1H-[1,2,3]-triazolo[4,5-c]pyridine-4-carbonitrile, triethylamine (0.5 ml) in THF (5 ml). The mixture was stirred at rt for 5 hours, then diluted with ethyl acetate (100 ml), washed with sodium bicarbonate (50 ml), brine (50 ml), dried over sodium sulphate, solvent removed, residue dissolved in MeOH/NMP (3:1, 6 ml), and purified by basic hplc to give free base which was then converted to HCl salt as usual (70 mg). ¹H NMR (CD3OD) δ: 8.68 (s, 1H), 8.5 (s, 1H), 8.46 (d, 1H), 7.65 (d, 1H), 4.47 (s, 3H), 4.27 (s, 2H), 3.60 (t, 2H), 3.04 (s, 3H), 2.96 (s, 6H), 2.90 (t, 2H), 1.95 (m, 2H). MS m/z 460 (M+H).

EXAMPLE 46

6-(4-(3-((1S,4S)-2,5-diazabicyclo[2.2.1]heptan-2-yl)propyl)-3-(trifluoromethyl)phenyl)-1-methyl-1H-[1,2,3]triazolo[4,5-d]pyridine-4-carbonitrile hydrochloride

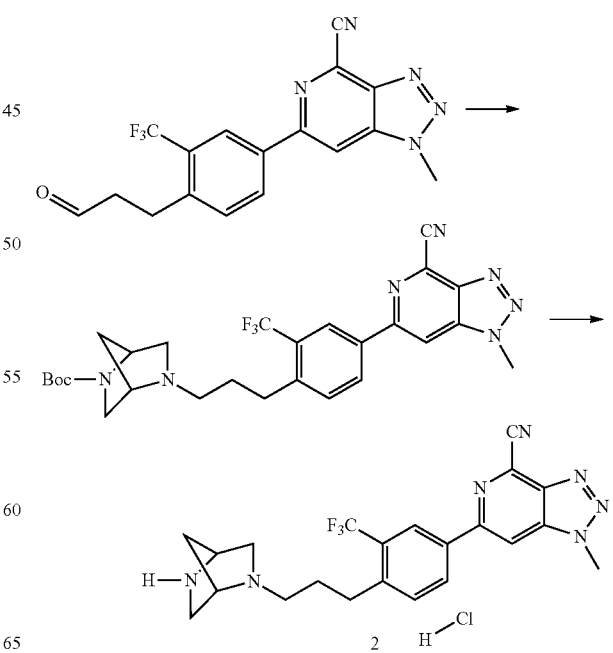

103

A: (1S,4S)-tert-butyl 5-(3-(4-(4-cyano-1-methyl-1H-[1,2,3]triazolo[4,5-d]pyridin-6-yl)-2-(trifluoromethyl)phenyl)propyl)-2,5-diazabicyclo[2.2.1]heptane-2-carboxylate Methyl-6-(4-(3-oxopropyl)-3-(trifluoromethyl)phenyl)-1H-[1,2,3]triazolo[4,5-c]pyridine-4-carbonitrile (200 mg), (1S,4S)-tert-butyl 2,5-diazabicyclo[2.2.1]heptane-2-carboxylate (221 mg) was dissolved in a mixed solvent of DCM (3 ml) and methanol (5 ml) containing acetic acid (0.4 ml). Sodium triacetoxyborohydride (350 mg) was then added in portions and the mixture was stirred at rt for further 3 hours. After diluting with ethyl acetate (100 ml), washed with sodium carbonate (30 ml), brine (20 ml), dried over sodium sulphate, solvent removed under vacuum, residue was then columned on silica gel using DCM:MeOH (20:1) as eluant to give (1S,4S)-tert-butyl 5-(3-(4-(4-cyano-1-methyl-1H-[1,2,3]triazolo[4,5-c]pyridin-6-yl)-2-(trifluoro-methyl)phenyl)propyl)-2,5-diazabicyclo[2.2.1]heptane-2-carboxylate (220 mg). $^1$H NMR (CDCl3) δ: 8.33 (s, 1H), 8.26 (d, 1H), 8.04 (s, 1H), 7.55 (d, 1H), 4.46 (s, 3H), 4.40 (br, 0.4H), 4.25 (br, 0.6H), 3.4-3.6 (m, 2H), 3.18 (m, 1H), 2.8-3.0 (m, 3H), 2.5-2.75 (m, 3H), 1.5-1.9 (m, 4H), 1.46 (s, 9H). MS m/z 542 (M+H).

B: 6-(4-(3-((1S,4S)-2,5-diazabicyclo[2.2.1]heptan-2-yl)propyl)-3-(trifluoromethyl)phenyl)-1-methyl-1H-[1,2,3]triazolo[4,5-d]pyridine-4-carbonitrile hydrochloride TFA (2 ml) was added to the solution of (1S,4S)-tert-butyl 5-(3-(4-(4-cyano-1-methyl-1H-[1,2,3]triazolo[4,5-c]pyridin-6-yl)-2-(trifluoromethyl)phenyl)propyl)-2,5-diazabicyclo[2.2.1]heptane-2-carboxylate in MeCN (2 ml) and DCM (3 ml). The mixture was stirred at rt for 20 minutes, then solvent removed under vacuum, and residue co-evaporated with 20 ml toluene. The residue was taken into EtOAc (2 ml) and product precipitated by adding ether (5 ml) and collected by filtration to give 230 mg product as an off-white solid. 65 mg of this TFA salt was then SCXed and converted to HCl salt (42 mg). $^1$H NMR (CD3OD) δ: 8.70 (s, 1H), 8.60 (s, 1H), 8.45 (d, 1H), 7.72 (d, 1H), 4.66 (s, 1H), 4.60 (s, 1H), 4.48 (s, 3H), 3.4-4.0 (m, 6H), 3.0 (m, 2H), 2.0-2.7 (m, 4H), MS m/z 442 (M+H).

EXAMPLE 47 methyl-6-(4-(3-((1S,4S)-5-methyl-2,5-diazabicyclo[2.2.1]heptan-2-yl)propyl)-3-(trifluoromethyl)phenyl)-1H-[1,2,3]triazolo[4,5-d]pyridine-4-carbonitrile hydrochloride

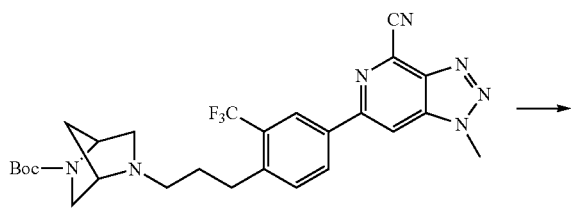

104

-continued

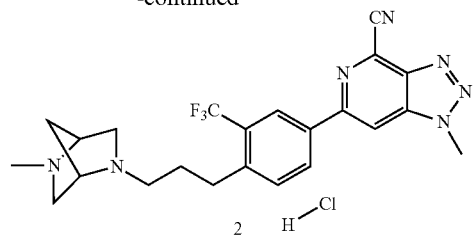

Sodium triacetoxyborohydride (200 mg) was added in portions to the solution of 6-(4-(3-((1S,4S)-2,5-diazabicyclo[2.2.1]heptan-2-yl)propyl)-3-(trifluoromethyl)-phenyl)-1-methyl-1H-[1,2,3]triazolo[4,5-c]pyridine-4-carbonitrile (as TFA salt) in methanol (2 ml) containing 0.3 ml acetic acid and 0.12 ml fomaline (37%). The mixture was stirred at rt for 4 hours, the diluted with ethyl acetate (150 ml), washed with sodium carbonate, brine, dried, solvent removed, the residue columned on silica gel using 20:1 DCM:MeOH then DCM-MeOH (2MNH3) (1:1) as solvent to give 80 mg free base which was then converted to HCl salt (100 mg). $^1$H NMR (CD3OD) δ: 8.60 (s, 1H), 8.43 (s, 1H), 8.36 (d, 1H), 7.66 (d, 1H), 4.60 (br, 1H), 4.50 (br, 1H), 4.38 (s, 3H), 3.2-3.7 (m, 6H), 2.97 (s, 3H), 2.90 (t, 2H), 2.55 (br, 2H), 2.10 (m, 2H). MS m/z 456 (M+H).

EXAMPLE 48

Cathepsin S Assay Procedure

The inhibitory activity of the compounds of the invention was demonstrated in vitro by measuring the inhibition of recombinant human Cathepsin S as follows: To a 384 well microtitre plate is added 10 μl of a 100 μM solution of test compound in assay buffer (100 mM sodium acetate pH5.5, 5 mM EDTA, 5 mM dithiothreitol) with 10% dimethylsulfoxide (DMSO), plus 20 μl of 250 μM solution of the substrate Z-Val-Val-Arg-AMC (7-amido-coumarine derivative of the tripeptide N-benzyloxy-carbonyl-Val-Val-Arg-OH) in assay buffer and 45 μl of assay buffer. 25 μl of a 2 mg/l solution of activated recombinant human cathepsin S, in assay buffer, is then added to the well, yielding a final inhibitor concentration of 10 μM.

Enzyme activity is determined by measuring the fluorescence of the liberated aminomethylcoumarin at 440 nM using 390 nM excitation, at 20 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity). Compounds of the invention typically have a $IC_{50}$ (negative logarithm of the $IC_{50}$ concentration) for inhibition of human cathepsin S of more than 6. Most compounds of the invention have a $pIC_{50}$ of more than 8, such as exemplified by the compounds of examples 1, 2a, 2b, 2c, 2d, 3a, 3c, 3k, 4a, 4b, 8, 9a, 9b, 19, 20, 21, 22, 23, 24, 25, 26, 27a, 29, 30, 31, 32, 35, 36q, 36v, 36u, 36t, 36w, 36x, 37e, 37m, 37p, 37q, 37r, 39, 43.

Table I shows comparative Cathepsin S activity data for a number of 1H-[1,2,3]triazolo[4,5-c]pyridine-4-carbonitrile derivatives of the invention and their corresponding 1H-imidazo[4,5-c]pyridine-4-carbonitrile derivatives. The mere substitution of a carbon atom in the imidazo-moiety of the reference compounds with a nitrogen atom in the compounds of the invention results in a 3-17 fold higher activity as cathepsin S inhibitor.

TABLE I

| Compound | Bioavailability | Cat S activity IC$_{50}$ |
|---|---|---|
| Example 35 | | 3.3 nM |
| Reference imidazopyridine derivative from WO 2009/010491 - Example 2a | | 32 nM |
| Example 2a (HCl) | F: 42% (SD rat) | 1.5 nM |
| Reference imidazopyridine derivative EP 09150709.5 - Example 14d (HCl) | F: 9% (SD rat) | 8.3 nM |
| Example 4b (HCl) | | 9 nM |

TABLE I-continued

| Compound | Bioavailability | Cat S activity IC$_{50}$ |
|---|---|---|
| Reference imidazopyridine derivative EP 09150709.5 - Example 24c | | 26 nM |
| Example 44 | | 13 nM |
| WO 2009/010491, Example 15 | | 234 nM |
| Example 1 | | 0.8 nM |
| WO 2009/010491, Example 14a | | 8 nM |

EXAMPLE 49

Cathepsin K Assay Procedure

The inhibitory activity of the compounds of the invention was demonstrated in vitro by measuring the inhibition of recombinant human Cathepsin K as follows: To a 384 well microtitre plate is added 5 μl of a 100 μM solution of test compound in assay buffer (100 mM sodium acetate pH5.5, 5 mM EDTA, 5 mM dithiothreitol) with 10% dimethylsulfoxide (DMSO), plus 10 μl of 100 μM solution of the substrate Z-Phe-Arg-AMC (7-amido-coumarine derivative of the dipeptide N-benzyloxycarbonyl-Phe-Arg-OH) in assay buffer and 25 μl of assay buffer. 10 μl of a 1 mg/l solution of activated recombinant human cathepsin K, in assay buffer, is then added to the well, yielding a final inhibitor concentration of 10 μM.

Enzyme activity is determined by measuring the fluorescence of the liberated aminomethylcoumarin at 440 nM using 390 nM excitation, at 10 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity). Compounds of the invention have a $pIC_{50}$ (negative logarithm of the $IC_{50}$ concentration) for inhibition of human cathepsin K of less than 7.

EXAMPLE 50

Cell Based Lip10 Assay Procedure

Human B lymphoblastoid cells (Jiyoye) were cultured in RPMI 1640 medium at a density of 500 000 cells/ml in 24-well plates. Cells were treated with a concentration range of compounds (0.001-10 μM) and vehicle alone (DMSO, 0.1% v/v). In order to generate positive control treatments separate wells were treated with 10 μM E64d & 0.1 μM LHVS. The cells were incubated at 37° C. in a humidified incubator containing 5% $CO_2$. After 24 hours the plates were centrifuged at 150×g for five minutes and the media removed. Cells were lysed by adding 65 ul of ice-cold phosphate buffered saline (PBS) containing 1% (v/v) Triton X-100 and protease inhibitors and incubated on ice for 20 minutes. The samples were centrifuged at 18 000×g for 15 minutes at 4° C. and the resulting supernatants collected and stored at −80° C. until required. After measurement of protein concentration using a micro-BCA protein assay all samples were diluted to 10 g protein/ml and 50 l of each sample were coated overnight at 4° C. onto wells of high protein-binding 96-well plates. The wells were washed once with PBS (200 l/well) and then incubated at room temperature for 2 hours with 10 μg/ml mouse anti-CD74 Pin.1 monoclonal antibody (50 l/well) in PBS containing 0.05% (v/v) Tween-20 (PBS-T) and 2% (w/v) BSA (PBS-T/BSA). Unbound antibody was then removed by washing three times with PBS-T and followed by the addition of rabbit anti-mouse IgG antibody conjugated to horseradish peroxidase. After washing five times with PBS-T 100 μl of tetramethylbenzidine substrate was added to each well and incubated for 10 minutes on a plate shaker. The reaction was stopped by the addition of 100 μl of 1M hydrochloric acid. Antibody binding was quantified by measuring the optical density (OD, 450 nm) using a Molecular Devices Spectramax Plus. The OD of vehicle-only treated cells was removed from all values and the data was expressed as a percentage of the OD generated from the mean E64d/LHVS-treated cells. The potency of compounds ($EC_{50}$) was measured by calculating the concentration of inhibitor required to generate 50% inhibition relative to E64d/LHVS-treated cells. Compounds of the invention have a $pEC_{50}$ (negative logarithm of the $EC_{50}$ concentration) value greater than 10 μM. Many compounds have $pEC_{50}$ greater than 7, such as exemplified by the compounds of examples 2a, 2d, 3a, 37 g.

The invention claimed is:

1. A 1H-[1,2,3]triazolo[4,5-c]pyridine-4-carbonitrile derived Cathepsin S inhibitor of Formula I

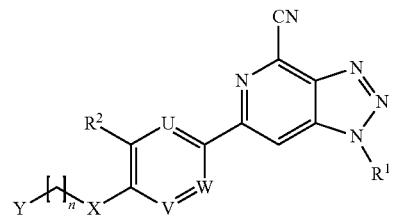

Formula I wherein
$R_1$ is H or $(C_{1-3})$alkyl;
$R_2$ is halogen or $(C_{1-4})$alkyl, optionally substituted with one or more halogens;
n is 1-3;
X is O or $CH_2$;
U, V and W are CH; or one of U, V and W is N;
wherein Y is selected from
  OH;
  $(C_{1-4})$alkyloxy;
  $(C_{1-4})$alkyloxy$(C_{1-4})$alkyloxy;
  $NR_3R_4$;
  $NR_4SO_2R_5$;
  pyridyl or N-oxy-pyridyl;
  Het;

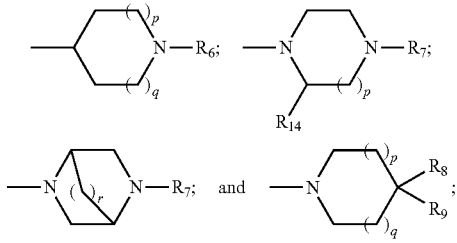

or a pharmaceutically acceptable salt thereof.

2. The 1H-[1,2,3]triazolo[4,5-c]pyridine-4-carbonitrile derived Cathepsin S inhibitor of Formula I of claim 1, wherein
$R_1$ is H or $(C_{1-3})$alkyl;
$R_2$ is halogen or $(C_{1-4})$alkyl, optionally substituted with one or more halogens;
n is 1-3;
X is O or $CH_2$;
U, V and W are CH; or one of U, V and W is N;
and
wherein Y is selected from
  OH;
  $(C_{1-4})$alkyloxy;
  $(C_{1-4})$alkyloxy$(C_{1-4})$alkyloxy;
  $NR_3R_4$;
$NR_4SO_2R_5$;
pyridyl or N-oxy-pyridyl;
Het;

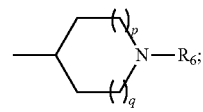

-continued

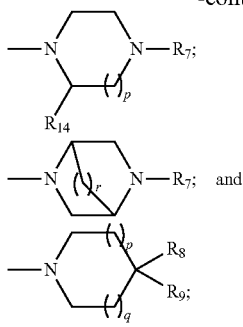

R$_3$ is H, (C$_{1-3}$)alkyl, (C$_{1-6}$)alkylCO, NR$_{10}$R$_{11}$CR$_{12}$R$_{13}$CO or NR$_{10}$R$_{11}$CO(CH$_2$)$_m$;
R$_4$ is H, (C$_{1-3}$)alkyl or (C$_{3-5}$)cycloalkyl; or
R$_3$ and R$_4$ together with the nitrogen to which they are bonded form a saturated 6-membered heterocyclic ring containing a further heteroatom selected from O, S and SO$_2$;
R$_5$ is (C$_{1-6}$)alkyl;
R$_6$ is selected from
H;
(C$_{1-4}$)alkyl, optionally substituted with 1 or 2 substituents selected from OH;
halogen, CF$_3$ or (C$_{1-4}$alkylsulfonyl;
(C$_{1-4}$)alkylsulfonyl;
(C$_{1-6}$)alkylcarbonyl;
Het;
Het-CH$_2$;
pyridyl, optionally fused to a benzo ring and optionally substituted with (C$_{1-4}$)alkyl, halogen or cyano;
NR$_{10}$R$_{11}$CO(CH$_2$)$_m$; and
NR$_{10}$R$_{11}$CR$_{12}$R$_{13}$CO;
R$_7$ is selected from
H;
(C$_{1-4}$)alkyl, optionally substituted with 1 or 2 substituents selected from OH;
halogen, CF$_3$ or (C$_{1-4}$)alkylsulfonyl;
(C$_{1-6}$)alkylcarbonyl;
(C$_{1-4}$)alkylsulfonyl;
pyridyl, optionally substituted with (C$_{1-3}$)alkyl, halogen or CF$_3$; and
NR$_{10}$R$_{11}$CO(CH$_2$)$_m$;
R$_8$ is H, (C$_{1-4}$)alkyl or OH;
R$_9$ is H, (C$_{1-4}$)alkyl or NR$_{10}$R$_{11}$CO(CH$_2$)$_m$;
R$_{10}$ and R$_{11}$ are independently H or (C$_{1-6}$)alkyl; or
R$_{10}$ and R$_{11}$ form together with the N to which they are bonded a 5-7 membered saturated heterocyclic ring, optionally comprising a further heteroatom selected form O and S;
R$_{12}$ and R$_{13}$ are independently H or (C$_{1-4}$) alkyl; or
R$_{12}$ and R$_{13}$ form together with the carbon atom to which they are bonded a (C$_{3-5}$)cycloalkyl ring;
R$_{14}$ is H, CF$_3$ or oxo;
Het is a 5-membered heteroaryl ring comprising 1-3 heteroatoms selected from O, S and N, optionally substituted with (C$_{1-4}$)alkyl, halogen or cyano;
p and q are independently 0, 1 or 2;
r is 1 or 2;
m is 0, 1 or 2;
or a pharmaceutically acceptable salt thereof.

3. The 1H-[1,2,3]triazolo[4,5-c]pyridine-4-carbonitrile derived Cathepsin S inhibitor of claim 2, wherein U, V and W are CH; or V is N.

4. The 1H-[1,2,3]triazolo[4,5-c]pyridine-4-carbonitrile derived Cathepsin S inhibitor of claim 3, wherein X is O and U, V and W are CH.

5. The 1H-[1,2,3]triazolo[4,5-c]pyridine-4-carbonitrile derived Cathepsin S inhibitor of claim 4, wherein R$_1$ is methyl and R$_2$ is CF$_3$.

6. The 1H-[1,2,3]triazolo[4,5-c]pyridine-4-carbonitrile derived Cathepsin S inhibitor of claim 1 which is selected from
1-methyl-6-(4-(2-(piperidin-4-yl)ethoxy)-3-(trifluoromethyl)phenyl)-1H-[1,2,3]triazolo[4,5-c]pyridine-4-carbonitrile;
6-(4-(2-(1-(2-dimethylamino-2-oxoethyl)piperidin-4-yl)ethoxy)-3-(trifluoromethyl)phenyl)-1-methyl-1H-[1,2,3]triazolo[4,5-c]pyridine-4-carbonitrile;
1-methyl-6-(4-(2-(1-(2-methylamino-2-oxoethyl)piperidin-4-yl)ethoxy)-3-(trifluoromethyl)phenyl)-1H-[1,2,3]triazolo[4,5-c]pyridine-4-carbonitrile;
6-(4-(2-(1-(2-amino-2-oxoethyl)piperidin-4-yl)ethoxy)-3-(trifluoromethyl)phenyl)-1-methyl-1H-[1,2,3]triazolo[4,5-c]pyridine-4-carbonitrile;
6-(4-(2-(1-(2-hydroxy-2-methylpropyl)piperidin-4-yl)ethoxy)-3-(trifluoromethyl)phenyl)-1-methyl-1H-[1,2,3]triazolo[4,5-c]pyridine-4-carbonitrile;
1-methyl-6-(4-(2-(1-(pyridin-2-yl)piperidin-4-yl)ethoxy)-3-(trifluoromethyl)phenyl)-1H-[1,2,3]triazolo[4,5-c]pyridine-4-carbonitrile;
1-methyl-6-(4-(2-(1-(6-methylpyridin-2-yl)piperidin-4-yl)ethoxy)-3-(trifluoromethyl)phenyl)-1H-[1,2,3]triazolo[4,5-c]pyridine-4-carbonitrile;
6-(4-(2-(1-(3-cyanopyridin-2-yl)piperidin-4-yl)ethoxy)-3-(trifluoromethyl)phenyl)-1-methyl-1H-[1,2,3]triazolo[4,5-c]pyridine-4-carbonitrile;
1-methyl-6-(4-(2-(1-(methylsulfonyl)piperidin-4-yl)ethoxy)-3-(trifluoromethyl)phenyl)-1H-[1,2,3]triazolo[4,5-c]pyridine-4-carbonitrile;
6-(4-(2-(1-acetylpiperidin-4-yl)ethoxy)-3-(trifluoromethyl)phenyl)-1-methyl-1H-[1,2,3]triazolo[4,5-c]pyridine-4-carbonitrile;
4-(2-(4-(4-cyano-1-methyl-1H-[1,2,3]triazolo[4,5-c]pyridin-6-yl)-2-(trifluoromethyl)phenoxy)ethyl)-N-methylpiperidine-1-carboxamide;
1-methyl-6-(4-(2-(1-(2-(methylsulfonyl)ethyl)piperidin-4-yl)ethoxy)-3-(trifluoromethyl)phenyl)-1H-[1,2,3]triazolo[4,5-c]pyridine-4-carbonitrile;
1-methyl-6-(4-(pyridin-2-ylmethoxy)-3-(trifluoromethyl)phenyl)-1H-[1,2,3]triazolo[4,5-c]pyridine-4-carbonitrile;
1-methyl-6-(4-(1-N-oxy-pyridin-2-ylmethoxy)-3-(trifluoromethyl)phenyl)-1H-[1,2,3]triazolo[4,5-c]pyridine-4-carbonitrile;
1-Methyl-6-(6-(2-(piperidin-4-yl)ethoxy)-5-(trifluoromethyl)pyridin-3-yl)-1H-[1,2,3]triazolo[4,5-c]pyridine-4-carbonitrile;
6-(6-(2-(1-(2-Dimethylamino-2-oxo-ethyl)piperidin-4-yl)ethoxy)-5-(trifluoromethyl)pyridin-3-yl)-1-methyl-1H-[1,2,3]triazolo[4,5-c]pyridine-4-carbonitrile;
1-Methyl-6-(6-(2-(1-(2-methylamino-2-oxo-ethyl)piperidin-4-yl)ethoxy)-5-(trifluoromethyl)pyridin-3-yl)-1H-[1,2,3]triazolo[4,5-c]pyridine-4-carbonitrile;
6-(6-(2-(1-(2-Amino-2-oxo-ethyl)piperidin-4-yl)ethoxy)-5-(trifluoromethyl)pyridin-3-yl)-1-methyl-1H-[1,2,3]triazolo[4,5-c]pyridine-4-carbonitrile;
1-Methyl-6-(6-(2-(1-(2-oxo-2-(pyrrolidin-1-yl)ethyl)piperidin-4-yl)ethoxy)-5-(trifluoromethyl)pyridin-3-yl)-1H-[1,2,3]triazolo[4,5-c]pyridine-4-carbonitrile;

1-Methyl-6-(6-(2-(1-(2-morpholino-2-oxoethyl)piperidin-4-yl)ethoxy)-5-(trifluoromethyl)pyridin-3-yl)-1H-[1,2,3]triazolo[4,5-c]pyridine-4-carbonitrile;
6-(4-(2-(1-(1-aminocyclopropanecarbonyl)piperidin-4-yl)ethoxy)-3-(trifluoromethyl)phenyl)-1-methyl-1H-[1,2,3]triazolo[4,5-c]pyridine-4-carbonitrile;
6-(4-(2-(azetidin-3-yl)ethoxy)-3-(trifluoromethyl)phenyl)-1-methyl-1H-[1,2,3]triazolo[4,5-c]pyridine-4-carbonitrile;
6-(4-(2-(1-(2-dimethylamino-2-oxoethyl)azetidin-3-yl)ethoxy)-3-(trifluoromethyl)phenyl)-1-methyl-1H-[1,2,3]triazolo[4,5-c]pyridine-4-carbonitrile;
6-(4-(2-methoxyethoxyl)methoxy)-3-(trifluoromethyl)phenyl)-1-methyl-1H-[1,2,3]triazolo[4,5-c]pyridine-4-carbonitrile;
6-(4-(3-hydroxypropoxy)-3-(trifluoromethyl)phenyl)-1-methyl-1H-[1,2,3]triazolo[4,5-c]pyridine-4-carbonitrile;
N-(3-(4-(4-cyano-1-methyl-1H-[1,2,3]triazolo[4,5-c]pyridin-6-yl)-2-(trifluoromethyl)phenoxy)propyl)acetamide;
6-(4-(3-(dimethylamino)propoxy)-3-(trifluoromethyl)phenyl)-1-methyl-1H-[1,2,3]triazolo[4,5-c]pyridine-4-carbonitrile;
6-(4-(3-(4-hydroxy-4-methylpiperidin-1-yl)propoxy)-3-(trifluoromethyl)phenyl)-1-methyl-1H-[1,2,3]triazolo[4,5-c]pyridine-4-carbonitrile;
1-(3-(4-(4-cyano-1-methyl-1H-[1,2,3]triazolo[4,5-c]pyridin-6-yl)-2-(trifluoromethyl)phenoxy)propyl)piperidine-4-carboxamide;
1-methyl-6-(3-(trifluoromethyl)-4-(3-(4-(4-(trifluoromethyl)pyridin-2-yl)piperazin-1-yl)propoxy)phenyl)-1H-[1,2,3]triazolo[4,5-c]pyridine-4-carbonitrile;
1-methyl-6-(4-(3-(4-(3-methylpyridin-2-yl)piperazin-1-yl)propoxy)-3-(trifluoromethyl)phenyl)-1H-[1,2,3]triazolo[4,5-c]pyridine-4-carbonitrile;
6-(4-(3-(4-(5-chloropyridin-2-yl)piperazin-1-yl)propoxy)-3-(trifluoromethyl)phenyl)-1-methyl-1H-[1,2,3]triazolo[4,5-c]pyridine-4-carbonitrile;
6-(4-(3-(4-(3-chloropyridin-2-yl)piperazin-1-yl)propoxy)-3-(trifluoromethyl)phenyl)-1-methyl-1H-[1,2,3]triazolo[4,5-c]pyridine-4-carbonitrile;
6-(4-(2-(1-(1,2,4-oxadiazol-5-yl)methyl)piperidin-4-yl)ethoxy)-3-(trifluoromethyl)phenyl)-1-methyl-1H-[1,2,3]triazolo[4,5-c]pyridine-4-carbonitrile;
6-(4-(2-(1-(1,2,4-oxadiazol-3-yl)methyl)piperidin-4-yl)ethoxy)-3-(trifluoromethyl)phenyl)-1-methyl-1H-[1,2,3]triazolo[4,5-c]pyridine-4-carbonitrile;
1-methyl-6-(4-(2-(1-(oxazol-2-ylmethyl)piperidin-4-yl)ethoxy)-3-(trifluoromethyl)phenyl)-1H-[1,2,3]triazolo[4,5-c]pyridine-4-carbonitrile;
1-methyl-6-(4-(pyridin-3-ylmethoxy)-3-(trifluoromethyl)phenyl)-1H-[1,2,3]triazolo[4,5-c]pyridine-4-carbonitrile;
1-methyl-6-(4-(2-(1-(6-methylpyridin-2-yl)azetidin-3-yl)ethoxy)-3-(trifluoromethyl)phenyl)-1H-[1,2,3]triazolo[4,5-c]pyridine-4-carbonitrile;
1-methyl-6-(4-(2-(1-(pyridin-2-yl)azetidin-3-yl)ethoxy)-3-(trifluoromethyl)phenyl)-1H-[1,2,3]triazolo[4,5-c]pyridine-4-carbonitrile hydrochloride;
methyl-6-(4-(1-N-oxy-pyridin-3-ylmethoxy)-3-(trifluoromethyl)phenyl)-1H-[1,2,3]triazolo[4,5-c]pyridine-4-carbonitrile;
1-methyl-6-(4-(pyridin-4-ylmethoxy)-3-(trifluoromethyl)phenyl)-1H-[1,2,3]triazolo[4,5-c]pyridine-4-carbonitrile;
methyl-6-(4-(1-N-oxy-pyridin-4-ylmethoxy)-3-(trifluoromethyl)phenyl)-1H-[1,2,3]triazolo[4,5-c]pyridine-4-carbonitrile;
6-(6-(2-(1-(2-Hydroxy-2-methylpropyl)piperidin-4-yl)ethoxy)-5-(trifluoromethyl)pyridin-3-yl)-1-methyl-1H-[1,2,3]triazolo[4,5-c]pyridine-4-carbonitrile;
6-(6-(2-(1-(2-Hydroxyethyl)piperidin-4-yl)ethoxy)-5-(trifluoromethyl)pyridin-3-yl)-1-methyl-1H-[1,2,3]triazolo[4,5-c]pyridine-4-carbonitrile;
6-(4-(2-(1-(2-dimethylamino-2-oxoethyl)azetidin-3-yl)ethoxy)-3-(trifluoromethyl)phenyl)-1-methyl-1H-[1,2,3]triazolo[4,5-c]pyridine-4-carbonitrile hydrochloride;
6-(4-(3-(dimethylamino)propoxy)-3-(trifluoromethyl)phenyl)-1-methyl-1H-[1,2,3]triazolo[4,5-c]pyridine-4-carbonitrile;
2-(4-(3-(4-(4-cyano-1-methyl-1H-[1,2,3]triazolo[4,5-c]pyridin-6-yl)-2-(trifluoromethyl)phenoxy)propyl)piperazin-1-yl)-N,N-dimethylacetamide;
6-(4-(3-(4-(2-hydroxyethyl)piperazin-1-yl)propoxy)-3-(trifluoromethyl)phenyl)-1-methyl-1H-[1,2,3]triazolo[4,5-c]pyridine-4-carbonitrile dihydrochloride;
2-(4-(2-(4-(4-cyano-1-methyl-1H-[1,2,3]triazolo[4,5-c]pyridin-6-yl)-2-(trifluoromethyl)phenoxy)ethyl)piperazin-1-yl)-N,N-dimethylacetamide; dihydrochloride;
6-(4-(2-(4-(2-hydroxy-2-methylpropyl)piperazin-1-yl)ethoxy)-3-(trifluoromethyl)phenyl)-1-methyl-1H-[1,2,3]triazolo[4,5-c]pyridine-4-carbonitrile dihydrochloride;
2-((1S,4S)-5-(2-(4-(4-cyano-1-methyl-1H-[1,2,3]triazolo[4,5-c]pyridin-6-yl)-2-(trifluoromethyl)phenoxy)ethyl)-2,5-diazabicyclo[2.2.1]heptan-2-yl)-N,N-dimethylacetamide;
N-(3-(4-(4-cyano-1-methyl-1H-[1,2,3]triazolo[4,5-c]pyridin-6-yl)-2-(trifluoromethyl)phenyl)propyl)-2-(dimethylamino)-N-methylacetamide;
methyl-6-(4-(3-((1S,4S)-5-methyl-2,5-diazabicyclo[2.2.1]heptan-2-yl)propyl)-3-(trifluoromethyl)phenyl)-1H-[1,2,3]triazolo[4,5-c]pyridine-4-carbonitrile hydrochloride;
or a pharmaceutically acceptable salt thereof.

7. A pharmaceutical composition comprising a 1H-[1,2,3]triazolo[4,5-c]pyridine-4-carbonitrile derived Cathepsin S inhibitor of claim 1, or a pharmaceutically acceptable salt thereof, in admixture with pharmaceutically acceptable auxiliaries.

* * * * *